(12) United States Patent
Mahan et al.

(10) Patent No.: US 7,026,155 B2
(45) Date of Patent: Apr. 11, 2006

(54) METHOD OF REDUCING BACTERIAL PROLIFERATION

(75) Inventors: Michael J. Mahan, Santa Barbara, CA (US); Douglas M. Heithoff, Goleta, CA (US); David A. Low, Goleta, CA (US); Robert L Sinsheimer, Santa Barbara, CA (US)

(73) Assignee: Regents of the University of California, Oakland, CA (US)

( * ) Notice: Subject to any disclaimer, the term of this patent is extended or adjusted under 35 U.S.C. 154(b) by 194 days.

(21) Appl. No.: 09/928,227

(22) Filed: Aug. 9, 2001

(65) Prior Publication Data

US 2002/0086332 A1 Jul. 4, 2002

Related U.S. Application Data

(63) Continuation-in-part of application No. 09/612,116, filed on Jul. 7, 2000, now abandoned, which is a continuation-in-part of application No. 09/495,614, filed on Feb. 1, 2000, now abandoned.

(60) Provisional application No. 60/183,043, filed on Feb. 2, 1999, provisional application No. 60/198,250, filed on May 5, 1999.

(51) Int. Cl.
*G01N 33/53* (2006.01)

(52) U.S. Cl. ............... 435/252.1; 435/320.1; 424/200.1

(58) Field of Classification Search ............ 514/29, 514/30, 35, 46, 44, 54; 435/172.3, 183, 193, 435/325, 366, 371, 375, 6, 455, 7.1, 252.3, 435/320.1, 252.33, 252.35, 15, 18, 69.1, 435/235.1; 536/231, 24.5, 23.7, 23.1; 424/130.1, 424/200.1, 261.1, 234.1, 184.1, 257.1, 258.1

See application file for complete search history.

(56) References Cited

U.S. PATENT DOCUMENTS

| | | | |
|---|---|---|---|
| 4,016,253 | A | 4/1977 | Switzer et al. |
| 4,167,560 | A | 9/1979 | Wohler, Jr. |
| 4,171,353 | A | 10/1979 | Ryan |
| 4,436,728 | A | 3/1984 | Ribi et al. |
| 4,726,947 | A | 2/1988 | Shimada et al. |
| 5,057,540 | A | 10/1991 | Kensil et al. |
| 5,077,284 | A | 12/1991 | Loria et al. |
| 5,171,568 | A | 12/1992 | Burke et al. |

(Continued)

FOREIGN PATENT DOCUMENTS

WO WO 91/16924 11/1991

(Continued)

OTHER PUBLICATIONS

Blyn, LB et al, EMBO, Dec. 1990, vol. 9(12), pp. 4045-4054, Regulation of pap pilin phase variation by a mechanism involving differential dam methylation states.*

(Continued)

*Primary Examiner*—Lynette R. F. Smith
*Assistant Examiner*—Ginny Allen Portner
(74) *Attorney, Agent, or Firm*—David J. Aston; Peters Verny Jones Schmitt & Aston, LLP

(57) ABSTRACT

Bacteria and in particular pathogenic bacteria are treated in a manner which alters the bacteria's native level or activity of DNA methyltransferase (Dam). The alteration results in a change in the bacteria's native level of methylation of adenine in a GATC tetranucleotide which inhibits virulence of the bacteria. Thus, compounds which inhibit proliferation of bacteria are useful in treating bacterial infections.

12 Claims, 8 Drawing Sheets

U.S. PATENT DOCUMENTS

| | | | |
|---|---|---|---|
| 5,210,035 A | | 5/1993 | Stocker |
| 5,273,744 A | | 12/1993 | Musoke et al. |
| 5,294,441 A | | 3/1994 | Curtiss, III |
| 5,407,684 A | | 4/1995 | Loria et al. |
| 5,434,065 A | | 7/1995 | Mahan et al. |
| 5,587,305 A | | 12/1996 | Briggs et al. |
| 5,672,345 A | | 9/1997 | Curtiss, III |
| 5,840,483 A | | 11/1998 | Curtiss, III |
| 5,855,880 A | * | 1/1999 | Curtiss et al. ............. 424/93.2 |
| 5,872,104 A | * | 2/1999 | Vermeulen et al. ........... 514/29 |
| 5,912,119 A | | 6/1999 | Radman et al. |
| 5,914,113 A | | 6/1999 | Schrier |
| 5,961,985 A | | 10/1999 | Sprouse et al. |
| 5,965,415 A | * | 10/1999 | Radman et al. ............ 435/69.1 |
| 6,010,705 A | * | 1/2000 | Thune et al. ............ 424/234.1 |
| 6,033,673 A | | 3/2000 | Clements |
| 6,066,625 A | * | 5/2000 | MacLeod ...................... 514/44 |
| 6,072,102 A | * | 6/2000 | Cigan et al. ................. 800/274 |
| 6,184,211 B1 | * | 2/2001 | Szyf ............................. 514/44 |
| 6,190,669 B1 | * | 2/2001 | Noriega et al. .......... 424/258.1 |
| 6,238,901 B1 | | 5/2001 | Morgan et al. |
| 6,261,561 B1 | | 7/2001 | Stewart, Jr. et al. |
| 6,268,137 B1 | * | 7/2001 | Szyf et al. ...................... 435/6 |
| 6,300,084 B1 | * | 10/2001 | Drubin et al. ................ 435/7.1 |
| 6,399,074 B1 | * | 6/2002 | Roland .................... 424/200.1 |
| 6,410,273 B1 | * | 6/2002 | Crouzet et al. ............ 435/91.1 |
| 6,413,751 B1 | * | 7/2002 | Benkovic et al. ........... 435/193 |
| 6,506,735 B1 | * | 1/2003 | MacLeod ...................... 514/44 |
| 6,585,975 B1 | * | 7/2003 | Kleanthous et al. ..... 424/200.1 |
| 6,632,430 B1 | * | 10/2003 | Xu et al. ................... 424/94.5 |
| 6,680,182 B1 | * | 1/2004 | Khan et al. ................ 435/69.7 |
| 2002/0068068 A1 | * | 6/2002 | Mahan et al. ............ 424/200.1 |
| 2002/0076417 A1 | * | 6/2002 | Mahan et al. ............ 424/200.1 |
| 2002/0077272 A1 | * | 6/2002 | Mahan et al. .................. 514/1 |
| 2002/0086032 A1 | * | 7/2002 | Mahan et al. ............ 424/200.1 |
| 2002/0086332 A1 | * | 7/2002 | Mahan et al. ................ 435/7.1 |
| 2003/0124725 A1 | * | 7/2003 | Tanabe et al. ............... 435/455 |

FOREIGN PATENT DOCUMENTS

| | | | |
|---|---|---|---|
| WO | 92/11361 | * | 7/1992 |
| WO | WO 92/16231 | | 10/1992 |
| WO | WO 97/44487 | | 11/1997 |
| WO | WO 98/02552 | | 1/1998 |
| WO | 9812206 | * | 3/1998 |
| WO | WO 98/12206 | | 3/1998 |
| WO | WO 99/43809 | | 9/1999 |
| WO | WO 00/45840 | | 8/2000 |
| WO | WO 01/46428 | | 6/2001 |

OTHER PUBLICATIONS

Bandyopadhyay, R et al, Gene, vol. 140, pp. 67-71, 1994, The DNA adenine methyltransferase encoding gene (dam) of Vibrio cholerae.*
Boslego, JW et al, Chapter 17, Gonorrhea vaccines, pp.211-223, in Vaccines and Immunotherapy, 1991, Pergamon press, Edited by Stanley J. Cryz, Jr.*
Brawer, R et al, Arch. Microbiol. vol. 169, pp. 530-533, 1998, A temperature sensitive DNA adenine methyltransferase mutant of Salmonella typhimurium.*
Braaten, Bruce A et al, Journal of Bacteriology, vol. 173(5), Mar. 1991, pp. 1789-1800.*
Brawer, R et al, Abstracts of the General Meeting of the American Society for Microbiology, vol. 96(0), p. 500, abstract H-100, 1996.*
Rene, Brigitte, et al, Mutation Research, vol. 193(3), pp. 269-273, May 1988.*
Brooks, Joan E. et al, Nucleic Acids research, vol. 11, No. 3, pp. 837-851, 1993.*
Ellis, Ronald W. Chapter 29, New Technologies for Making Vaccines, pp. 568-574, In Vaccines, Plotkin & Mortimer.*
Gunn, JS et al, Nucleic Acids Research, vol. 25(20), pp. 4147-4152, 1997.*
Guyot, JB et al, Nucleic Acids Research, Voo. 21, pp. 3183-3190, 1993.*
Hale, WB et al, Molecular Genetics and Metabolism, vol. 65, pp. 191-196, 1998.*
Kupchella, E et al, 23rd Annual Scientific Meeting of the Environmental Mutagen Society, Reno/Sparks, Nevada, USA, Mar. 15-19, 1992, Suppl. 0(20, p. 33.*
Lu, AL et al, Journal of Bacteriology, Mar. 1990, vol. 172(3), pp. 1232-1240.*
Mankovich, JA et al, Journal of bacteriology, vol. 171(10), Oct. 1989, pp. 5325-5331.*
Marinus et al, Mol. Gen. Genet., vol. 192, pp. 288-289, 1983, Insertion Mutations in the dam gene of *Escherichia coli* K-12.*
Martin, C, Molecular Microbiology, Jul. 1996, vol. 21(2), pp. 281-292, The clp (CS31A) operon is negatively controlled by Lrp, ClpB and L-alanine at the transcriptional level.*
Meury, J et al, Biochemie, 1995, vol. 77(11), pp. 875-879.*
Nou, X et al, The EMBO Journal, vol. 14(23), pp. 5785-5797.*
Ritchie, L et al, Mutation Research, vol. 194, pp. 131-141, 1988.*
Ritchie, Lyndal J et al, Journal of Bacteriology, Jul. 1986, vol. 167(1), pp. 420-422.*
Stambuk, S et al, Genetics, vol. 150, pp. 533-542, Oct. 1998.*
Stamm, LV et al, FEMS Microbiol. Lett., vol. 155, pp. 115-119, 1997.*
Torreblanca, J et al, Genetics, vol. 144, pp. 15-26, Sep. 1996.*
van der Woude, MW et al, Molecular microbiology, Feb. 1994, vol. 11(4), pp. 605-618, Leucine-responsive protein and deoxyadenosine methylase control the phase variation and expression of the sfa and daa pili operons in *Escherichia coli*.*
Blyn, LB et al, The EMBO journal, vol. 9(12), pp. 4045-4054, 1990.*
Torreblanca, J et al, Genetics, vol. 144, pp. 15-26, Sep. 1996, DNA Adenine Methylase Mutants of Salmonella typhimurium and a Novel Dam Regulated locus.*
Bandyopadhyay, R et al, Gene, vol. 140, pp. 67-71, 1994, The DNA adnenine methyltransferase encoding gene (dam) of Vibrio cholerae.*
Arraj, JA et al, Journal of Bacteriology, vol. 153(1), pp. 562-565, Jan. 1983.*
Guha, S et al, Nucleic Acid Research, vol. 20(4), pp. 3607-3615, 1993.*
Bassing, CH et al Gene, Erratum 1992, Nov. 2, vol. 121(1), p. 183 and Gene 1992, Apr. 1, vol. 113, pp. 83-88.*
Ritchie, LJ et al, Journal of Bacteriology, vol. 167(1), pp. 420-422, Jul. 1986, Mutant Salmonella typhimurium LT2 deficient in DNA Adenine Methylation.*
Klemm, P et al, Bacterial adhesins: function and structure, Int. J. Med. Microbiol., Mar. 2000 vol. 290(1), pp. 27-35.*
Alsahli, M et al, Dig. Dis. 2001, vol. 19(2), pp. 148-157, Vaccines: an ongoing promise?.*
Niemann, H.H. et al, Adhesins and invasins of pathogenic bacteria: a structural view, Microbes and Infection, vol. 6, 2004, pp. 101-112.*

De Berardinis, P et al, Future Drugs Ltd. pp. 673-679, New recombinant vaccines based on the use of prokaryotic antigen-display systems, 2004, Expert. Rev. Vaccines, vol. 3(6).*

Posfai, G et al, Nucleic Acids REs. Dec. 11, 1984, vol. 12(23), pp. 9039-9049,Structue of the gene coding for the sequence-specific DNA methyltransferase of the B. subtilis phage SPR (abstact only).*

Labbe, D et al, Mol. Gen. Genet. Oct. 1990, Voo. 224(1), pp. 101-110, (abstract only).*

Demidova, GV et al, Biokhimiia, Oct. 1984, vol. 49(10), pp. 1594-1597, Comparison of specific recognition sites of adenine and cytosine DNA-methylase of Yersinia Pestis EV 76 C dam and dcm bby *Escherichia coli* methylases (abstract only).*

Lyngstadaas, A et al, Biochim Biophys ACTA, Oct. 18, 1999, vol. 1472 (1-2) pp. 376-384, (abstract only).*

Anderson, P. and Smith, D. H. (1977). "Immunogenicity in Weanling Rabbits of a Polyribophosphate Complex from *Haemophilus influenzae* Type B," *J. Infect. Dis.* 136:s63-s70.

Ash, C. (1999). "Dam Virulence," *Trends in Microbiology*, 7(6): 231.

Baker, R. C. et al. (1983). "Survival of Salmonella typhimurium and Staphylococcus aureus in Eggs Cooked by Different Methods," *Poult. Sci.* 62(7):1211-1216.

Bandyopadhyay and Das. (1994). "The DNA adenine methyltransferase-encoding gene (*dam*) of *Vibrio cholerae*,"*Gene* 140: 67-71.

Blattner et al. (1997). "The Complete Genome Sequence of *Escherichia coli* K-12," *Science* 277: 1453-1474.

Blyn, L.B. et al. (1990). "Regulation of *Pap* Pilin Phase Variation by a Mechanism Involving Differential Dam Methylation States," *The EMBO Journal* 9(12):4045-4054.

Boslego et al. (1991) Chapter 17 *In Vaccines and Immunotherapy* Pergamon Press, pp. 211-223.

Boyd, E.F. et al. (1993). "*Salmonella* Reference Collection B (SARB): Strains of 37 Serovars of Subspecies I," *Journal of General Microbiology* 139:1125-1132.

Braaten et al. (1994). "Methylation Patterns in Pap Regulatory DNa Control Pyelonephritis-Associated Pili Phase Variation in *E. coli,* " *Cell* 76: 577-588.

Brawer, R et al. (1996), Abstracts of the General Meeting of the American Society of Microbiology, vol. 96, p. 500.

Brawer, R. et al. (1998). "A Temperature-Sensitive DNA Adenine Methyltransferase Mutant of Salmonella typhimurium," *Arch. Microbiology* 169(6):530-533.

Brown, H. M. and Wilson, R. N. (1959). "Chronic Bronchitis in Industry an Account of a Trial of H. Influenzae Vaccine," *British Med. J.* 263-267.

Cardenas, L. et al. (1992). "Oral Immunization Using Live Attenuated Salmonella SPP. as Carriers of Foreign Antigens," *Clinical Microbiology Reviews* 5(3): 328-342.

Carroll, C. D. (1998). "Evaluation of a Structure-based Statine Cyclic Diamino Amide Encoded Combinatorial Library Against Plasmepsin II and Cathepsin D," *Bioorg. Med. Chem. Lett*. 8: 3203-3206.

Cerquetti, M.C. et al. (May 4-8, 1996) 97th General Meeting of the American Society for Microbiology, vol. 97.

Cerquetti, M.C. et al., Abstracts of the General Meeting of the American Society for Microbiology, vol. 96, Abstract H-48, p. 491.

Cerquetti, MC et al., (1997). Abstracts of the General Meeting of the American Society for Microbiology, vol. 97, p. 318.

Charlier, D. et al. (1995). "Pyrimidine Regulation of the *Escherichia coli* and Salmonella typhimurium carAB operons: CarP and Integration Host factor (IHF) Modulate the Methylation Status of a GATC Site Present in the Control Region," *Journal of Mol. Biol.* 250(4):383-391.

Chikami, G.K. et al. (1985). "Plasmid-Mediated Virulence in *Salmonella dublin* Demonstrated by Use of a Tn*5-oriT* Construct," *Infection and Immunity* 50(2):420-424.

Conner, C. P. et al. (1998). "Differential Patterns of Acquired Virulence Genes Distinguish *Salmonella* strains," *Proc. Natl. Acad. Sci. USA* 14: 4641-4645.

Conner, C. P. et al. (1998). "In Vivo Gene expression: Contributions to Infection, Virulence, and Pathogenesis," *Current Top Microbiol Immunol.* 225: 1-12.

Correa, N. E. et al. (2000). "Phosphorylation of the Flagellar Regulatory Protein FlrC is Necessary for *Vibrio Cholerae* Motility and Enhanced Colonization," *Molecular Microbiology* 35(4):743-755.

Curtiss, R. and Kelly, S.M. (1987). "Salmonella typhimurium Deletion Mutants Lacking Adenylate Cyclase and Cyclic AMP Receptor Protein are Avirulent and Immunogenic," *Infect. Immun.* 55(12): 3035-3043.

Donnenberg, M. S. et al. (1991). "Construction of an EAE Deletion Mutant of Enteropathogenic *Escherichia coli* by Using a Positive-Selection Suicide Vector," *Infect. Immun.* 59(12): 4310-4317.

Earhart, C.F. ed. (1996). "Uptake and Metabolism of Iron and Molybdenum," Chapter 71 *In Escherichia coli and Salmonella Cellular and Molecular Biology, 2nd ed, vol. 1*, ASM Press, Washington, D.C., pp. 1075-1090.

Eisenstein, T.K. (1999). "Mucosal Immune Defense: The Salmonella typhimurium Model," Chapter 3 *In Intracellular Bacterial Vaccine Vectors*. Paterson, y., ed., Wiley-Liss, Inc., York, NY, pp. 51-109.

Ellis, RW. ed. (1988). Chapter 29 *In Vaccines* WB Sunders Co., pp. 568-574.

Fleischmann et al. (1995). "Whole-Genome Random Sequencing and Assembly of *Haemophilus influenzae* Rd.," *Science* 269: 496-512.

Fraser et al. (1998). "Complete Genome Sequence of *Treponema pallidum*, the Syphilis Spirochete," *Science* 281: 375-388.

Garcia-Del Portillo, F. et al. (1999). "DNA Adenine Methylase Mutants of Salmonella typhimurium Show Defects in Protein Secretion, Cell Invasion, and M Cell Cytotoxicity," *Proc. Natl. Acad. Sci. USA* 96: 11578-11583.

Gast, R. K. and Beard, C. W. (1990). "Isolation of Salmonella enteritidis from Internal Organs of Experimentally Infected Hens," *Avian Dis.* 34:991-993.

Groisman, E.A. and Heffron, F. (1995). "Regulation of Salmonella Virulence by Two-Component Regulatory Systems," Chapter 20 *In Two-component signal transduction*. Hoch, J.A., ed., ASM Press, Washington, D.C. pp. 319-332.

Gulig, P.A. et al. (1993). "Molecular Analysis of SPV Virulence Genes of the Salmonella Virulence Plasmids," *Mol. Microbiol.* 7(6): 825-830.

Hafner, L.M. et al. (1991). "Precise Excision of Tn10 in Salmonella typhimurium: Effects of Mutations in the po1A, dam, mutH, and mutB Genes and of Methionine or Ethionine in the Plating Medium," *Mutation Research* 263 (3):179-184.

Hale, W. B. et al. (Jun. 1994). "Analysis of Nonmethylated GATC Sites in the *Escherichia coli* Chromosome and Identification of Sites that are Differentially Methylated in Response to Environmental Stimuli," *J Bacteriol.* 176(11): 3438-3441.

Hassan, J.O. and Curtiss, R. (1997). "Efficacy of a Live Avirulent Salmonella typhimurium Vaccine in Preventing Colonization and Invasion of Laying Hens by Salmonella typhimurium and Salmonella enteritidis," *Avian Dis.* 41: 781-791.

Heithoff, D.M. et al. (1997) "Bacteriol Infection as Assessed by In Vivo Gene Expression," *Proc. Natl. Acad. Sci. USA* 94: 934-939.

Heithoff, D.M. et al. (1997). "Dissecting the Biology of a Pathogen During Infection," *Trends Microbiol.* 5(12):509-513.

Heithoff, D.M. et al. (1999). "An Essential Role for DNA Adenine Methylation in Bacterial Virulence," *Science* 284 (5416):967-970.

Heithoff, D. M. et al. (1999). "Coordinate Intracellular Expression of *Salmonella* Genes Induced During Infection," *J. Bacteriol.* 181: 799-807.

Heithoff, D.M. et al. (Jun. 2000). Dissertion Abstracts International, vol. 60, 12-B, pages 5906-B, col. 2(abstracts only).

Hinton, M. et al. (1989). "Experimental *Salmonella enteritidis* Infection in Chicks, " *Ver. Rec.* (124):223.

Hone, D. et al. (1987). "Construction of Defined *galE* Mutants of *Salmonella* for Use as Vaccines," *J. Infect. Dis.* 156(1):167-174.

Hone, D.m. et al. (1999). "Mucosal Vaccination with *Salmonella* Vaccine Vectors," Chapter 6 *In Intracellular Bacterial Vaccine Vectors*. Paterson, Y. ed., Wiley-Liss, Inc., New York, pp. 171-222.

Hormaeche, C.E. et al. (1996). "Protection Against Oral Challenge Three Months After I.V. Immunization of BALB/c Mice With Live Aro *Salmonella typhimurium* and *Salmonella enteritidis* Vaccines is Serotype (Species)-Dependent and Only Partially Determined by the main LPS O Antigen," *Vaccine* 14(4):251-259.

Humphrey, T. J. et al. (1989). "The Survival of *Salmonella* in Shell Eggs Cooked Under Stimulated Domestic Conditions," *Epidem. Inf.* 103:35-45.

Humphrey, T.J. (1990). "Heat Resistance in *Salmonella enteritidis* Phage Type 4: the Influence of Storage Temperatures Before Heating," *J. App. Bacter.* 69:493-497.

Humprey, T. J. et al. (1990). "A Comparative Study of the Heat Resistance of *Salmonellas* in Homogenized Whole Egg, Egg Yolk or Albumen," *Epidemiol. Infect.* 104:237-241.

Jones, Bradley D. and Stanley Falkow. (1996). "Salmonelllosis: Host Immune Responses and Bacterial Virulence Determinants," *Annual Review Immunology* 14: 533-561.

Julio, S. M. et al. (1998). "Directed Formation of Chromosomal Deletions in *Salmonella typhimurium*: Targeting of Specific Genes Induced During Infection," *Molec. Gen. Genet.* 258: 178-181.

Kupchella, E et al., 23rd Annual Scientific Meeting of the Environmental mutagen society, Mar. 150-19, 1992, 0(20), pp. 33, 1992 (abstract only).

Lam, K.S. (1997). "Application of Combinatorial Library Methods in Cancer Research and Drug Discovery," *Anticancer Drug. Des.* 12: 145-167.

Lavelle, J.M. (1986). "Potassium Chromate Potentiates Frameshift Mutagenesis in *E. coli* and *S. typhimurium*, " *Mutant. Res.* 171:1-10; especially p. 7, col. 1.

LeClerc et al. (1996). "High mutation frequencies among *Escherichia coli* and *Salmonella* pathogens," *Science* 274: 1208-1211.

MacLeod, A. R. and Szyf, M. (1995). "Expression of Antisense to DNA Methyltransferase mRNA Induces DNA Demethylation and Inhibits Tumorigenesis," *J. Biol. Chem.* 7(14):8037-8043.

Mahan, M. J. (Apr. 9, 1994). "Revealing Bacterial Infection Strategies," *Lancet.* 343(8902): 869-70.

Mahan, M. J. et al. (1993). "Selection of Bacterial Virulence Genes that are Specifically Induced in Host Tissues," *Science* 259: 686-688.

Mahan, M. J. et al. (1995). "Antibiotic-based Selection for Bacterial Genes that are Specifically Induced During Infection During Infection of a Host," *Proc. natl. Acad. Sci. USA* 92: 669-673.

Mahan, M.J. et al. (2000). "Assessment of Bacterial Pathogenesis by Analysis of Gene Expression in the Host," *Annual Reviews* 34:139-164.

Mäkelä, P. H. et al. (1977). "Polysaccharide Vaccines of Group A. *Neisseria meningitidis* and *Haemophilus influenzae* Type b: A Field Trial in Finland," *J. Infec. Dis.* 136:s43-s50.

Mankovich, JA et al. (1989). "Nucleotide Sequence of the *Salmonella typhimurium* mutL Gene Required for Mismatch Repair: Homology of MutL to HexB of *Streptococcus pneumoniae* and to PMS1 of the Yeast *Saccharomyces cerevisiae*," *Journal of Bacteriology* 171(10):5325-5331. (Abstract only).

Marinus, M.G. (1984). "Correlation of DNA Adenine Methylase Activity with Spontaneous Mutability in *Escherichia coli* K-12," *Gene.* 28: 123-125.

Marinus, M.G. (1996). "Methylation of DNA," Chapter 53 *In E. coli and Salmonella: Cellular and Molecular Biology*, 2nd ed. vol. 1, ASM Press, Washington, D.C., pp. 782-791.

Mekalanos, J.J. (1992). "Environmental Signals Controlling Expression of Virulence Determinants in Bacteria," *J. Bacteriol.* 174(1):1-7.

Miller, J.H. (1972). *Experiments in Molecular Genetics*, Cold Spring Harbor Laboratory, Table of Contents.

Miller, S.I. et al. (1990). "*Salmonella* Vaccines with Mutations in the phoP Virulence Regulon," *Res. Microbiol.* 141:817-821.

Monack, D.M. et al. (1998). "*Yersinia*-induced Apoptosis In Vivo Aids in the Establishemtn of a Systemic Infection of Mice," *J. Exp. Med.* 188(11):2127-2137.

Neustadt, B.R. et al. (1998). "Construction of a Family of Biphenyl Combinatorial Libraries: Structure-activity Studies Utlilizing Libraries of Mixtures," *Bioorg. Med. Chem. Lett.* 8:2395-2398.

O'Farrell, P.H. (1975). "High Resolution Two-Dimensional Electrophoresis of Proteins," *The J. of Biol. Chemistry* 250(10):4007-4021.

O'Hanley, P. et al. (1985). "Molecular Basis of *Escherichia coli* Colonization of the Upper Urinary Tract in BALB/c Mice," *J. Clin. Invest.* 75(2):347-360.

O'Hanley, P. M. et al. (1985). "Gal-Gal Binding and Hemolysin Phenotypes and Genotypes Associated With Uropathogenic *Escherichia Coli,"* N . Engl. J. Med. 313(7): 414-420.

Pappenheimer, A. M. (1984). "Diptheria," *In Bacterial Vaccines* R. Germaier ed., Academic Press: Orlando, FL., pp. 1-36.

Parke, J. C. (1977). "Interim Report of a Controlled Field Trial Immunization with Capsular Polysaccharides of

*Haemophilus influenzae* Type b and Group C Neisseria meningitidis in Mecklenberg Country, North Carolina (Mar. 1974-Mar. 1976)," *J. Infec. Dis.* 136:s51-s56.

Parkman, P.D. et al. (1966). "Attenuated Rubella Virus," *N. Engl. J. Med.* 275(11):569-574.

Popoiel, I. and Turnbull, P. C. B. (1985). "Passage of *Salmonella enteritidis* and *Salmonella* thompson through Chick Ileocecal Mucosa," *Infect. and Immun.* 47(3):786-792.

Price, C. et al. (1988). "Evolution of DNA Sequence Specificity in Type I Restriction enzymes," *Biochem. Soc. Trans.* 16(6):942-943.

Reissenauer, A. et al. (1999). "Bacterial DNA Methylation: A Cell Cycle Regulator?" *Journal of Bacteriology* 181(17): 5135-5139.

Riggs, A.D. et al. (1996). *Epigenetic Mechanisms of Gene Regulation*, Russo, V.E.A., et al. eds., Cold Spring Harbor Laboratory Press, pp. 1-4.

Ringquist, S. and Cassandra L. Smith. (1992). "The *Escherichia coli* Chromosome Contains Specific, Unmethylated *dam* and *dcm* Sites," *Proc. Natl. Acad. Sci. USA* 89:4539-4543.

Ritchie, L. et al. (1988). "A Mutation in the DNA Adenine Methylase Gene (dam) of *Salmonella typhimurium* Decreases Susceptibility to 9-Aminoacridine-Induced Frameshift Mutagenesis," *Mutation Research*194:131-141.

Ritchie, L.J. et al. (1986). "Mutant of *Salmonella typhimurium* LT2 deficient in DNa adenine methylation," *J.l of Bacteriol.* 167(1):420-422.

Roberts et al. (1985). "Experimental Pyelonephritis in the Monkey," *J. Urol.* 133: 1068-1075.

Robertson G.T. et al. (2000). "The *Brucella abortus* CcrM DNA Methyltransferase Is Essential for Viability, and Its Overexpression Attenuates Intracellular Replication in Murine Macrophages," *J. of Bacteriol.* 182(12):3482-3489.

Roland et al. (993). "Spontaneous *mprA* mutants of *Salmonella typhimurium* Lt2 Define a New Two Component Regulatory System with a Possible Role in Virulence," *J. Bacteriol.* 75:4154-4164.

Sanderson, K.E. et al. "Strains of *Salmonella typhimurium* and Other *Salmonella* Species Used in Genetic Analysis," *In Escherichia coli* and *Salmonella*. 2nd Ed., vol. 2, Neifhardt, F.C. et al. eds., ASM Press: Washington, D.C., pp. 2496-2503.

Shivaprasad, H. L. (1990). "Pathogenesis of *Salmonella enteriditis* Infection in Laying Chickens. I. Studies on Egg Transmission, Clinical Signs, Fecal Shedding, and Serologic Responses," *Avian Diseases* 34:548-557.

Sirard, J. et al. (1999). "Live Attenuated *Salmonella*: A Paradigm of Mucosal Vaccines," *Immun. Rev.* 171:5-26.

Slauch, J. M. et al. (1991). "Cis-acting *ompF* Mutations that Result in OmpR-Dependent Constitutive Expressions," *J. Bacteriol.* 173: 4039-4048.

Smith C. L. et al. (1987). "Purification, Specific Framentation, and Separation of Large DNA Molecules," *Methods Enzymol.* 155: 449.

Satmbuk, S et al. (1998). "Mechanism and Control of Interspecies Recombination in *Escherichia coli*. I. Mismatch Repair, Methylation, Recombination and Replication Functions," *Genetics* 150:533-542.

Tacket, C.O. et al. (1992). "Comparison of the Safety and Immunogenicity of ΔaroC ΔaroD and Δcya Δcrp *Salmonella* typhi Strains in Adult Volunteers," *Infect. Immun.* 6(2):536-541.

Takashi, H. et al. (1990). "Induction of CD8 Cytotoxic T Cells by Immunization with Purified HIV-1 Envelope Protein In ISCOMs," *Nature* 344:873-875.

Tavazoie, S. et al. (1998). "Quantitative Whole-Genome Analysis of DNA-Protein Interactions by in vivo Methylases Protection in *E. coli*," *Nature Biotechnol.* 16:566-571.

Torreblanca, J. et al. (1996). "DNA Adenine Methylase Mutants of *Salmonella typhimurium* and a Novel Dam-Regulated Locus," *Genetics* 144(1): 15-26.

Van der Woude et al. (1998). "Formation of DNA Methylation Patterns: Non-Methylated GATC Sequences in *gut* and *pap* Operons," *J. Bacteriol.* 180: 5913-5920.

Van der Woude, M. W. et al. (1992). "Evidence for Global Regulatory Control of Pilus Expression in *Escherichia coli* by Lrp and DNA Methylation: Model Building Based on Analysis of PAP," *Mol Microbiol.* 6(17): 2429-2435.

Van der Woude, M.W. et al. (1996). "Epigenetic Phase Variation of the PAP Operon in *Escherichia coli*," *Trends Microbiol.* 4(1):5-9.

Vescovi, G. et al. (1996). "$Mg^{2+}$as an Extracellular Signal: Environmental Regulation of *Salmonella* Virulence," *Cell* 84: 165-174.

Vinella, D et al. (1996). "Mecillinam Resistance in *Escherichia coli* is Conferred by Loss of a Second Activity of the AroK protein," *J. of Bacteriol.* 178(13): 3818-3828.

Wang, R.F. and Sidney R. Kishner. (1991). "Construction of Versatile Low-Copy-Number Vecotrs for Cloning, Sequencing and Gene Expression in *Escherichia coli*," *Gene* 100: 195-199.

Bizzini, B. (1984). "Tetanus," Chapter 2 *In Bacterial Vaccines* R. Germanier ed., Academic Press Inc.: Orlando, Fl.. pp. 37-68.

Manclark, C.R. and Cowell, J.L. (1984). "Pertussis," Chapter 3 *In Bacterial Vaccines* R. Germanier Ed., Academic Press Inc.: Orlando, Fl.. pp. 69-106.

* cited by examiner

METHOD OF REDUCING BACTERIAL PROLIFERATION

CROSS-REFERENCE

This patent application is a continuation-in-part of U.S. patent application Ser. No. 09/612,116, filed Jul. 7, 2000 (now abandoned) which is a continuation-in-part of U.S. patent application Ser. No. 09/495,614, filed Feb. 1, 2000 (now abandoned), which claims the priority benefit of U.S. patent application Ser. No. 09/241,951, filed Feb. 2, 1999, converted to U.S. Provisional Ser. Nos. 60/183,043, and 09/305,603, filed May 5, 1999, converted to U.S. Provisional Ser. No. 60/198,250, all of which are incorporated by reference in their entirety and to which applications is claimed priority.

STATEMENT REGARDING FEDERALLY SPONSORED RESEARCH

This invention was made with Government support under Grant Nos. AI36373 (to M. Mahan) and AI23348 (to D. Low), awarded by the National Institutes of Health. The Government may have certain rights in this invention.

FIELD OF THE INVENTION

The present invention relates generally to methods of creating antibodies and to compositions including vaccines used in the methods. In particular, this invention relates to methods of creating antibodies using immunogenic compositions generally comprising bacteria which are normally pathogenic bacteria (e.g.,*Salmonella*) which have been modified to contain a mutation affecting DNA adenine methylase (Dam) which renders the bacteria non-pathogenic.

BACKGROUND OF THE INVENTION

Food-borne disease presents a serious threat to our health, the safety of the nation's food supply, and to the agricultural industry. Each year over 80 million Americans suffer from food poisoning, at a cost estimated between $5 and $23 billion annually in medical treatment and lost wages (Snydman, D. R., Food poisoning. In: *Infectious Diseases*, second edition, Gorbach, S. L., et al., eds., 768–781 (1998)). Our defenses against food-borne disease are failing as new pathogens have emerged that can cause more debilitating forms of disease and/or can no longer be controlled by available antibiotics; examples include *Escherichia coli* (*E. coli*) 0157:H7, *Salmonella enteritidis* (*S. enteritidis*), and *S. typhimurium* DT104 (Alterkruse, S. F., et al., *Emerging food borne diseases*, 3:July–September (1997)).

Salmonellosis is one of the major food-borne diseases in the United States, estimated at between 1 and 4 million cases/year (Shere, K. D., et al., *Salmonella infections. In: Infectious Diseases*, second edition, Gorbach, S. L., et al., eds., 699–712 (1998)). This disease is caused by exposure to products contaminated with Salmonella, e.g., animal products such as eggs, milk, poultry or the ingestion of food products that have been exposed to animal feces, including fruits and vegetables. Due to large scale manufacturing and distribution practices, salmonellosis outbreaks have affected large populations (Tauxe, R. V., et al., *Emerging food borne diseases: an evolving public health challenge. Emerging infectious diseases*, 3:October–December (1997)).

*Salmonella* is a prime example of a pathogenic microorganism whose various species are the cause of a spectrum of clinical diseases that include acute gastroenteritis and enteric fevers. *Salmonella* infections are acquired by oral ingestion. The microorganisms after traversing the stomach, invade and replicate in the intestinal mucosal cells. See, Hornik, et al., *N. Eng. J. Med.*, 283:686 (1970). Some species, such as *S. typhi*, can pass through this mucosal barrier and spread via the Peyer's patches to the lamina propria and regional lymph nodes. *Salmonella typhi*, which only infects man, is the cause of typhoid fever and continues to be an important public health problem for residents in the less developed world.

Urinary tract infections (UTI) are among the most common bacterial infections. It is estimated that about 20% of women will experience at least one UTI during their lifetime. Although women are the major target of UTI, men and children can also contract this disease. About 70% of all UTI are caused by uropathogenic *Escherichia coli*. The disease may be limited to the lower urinary tract (cystitis) or can involve the renal pelvis (pyelonephritis). Over 90% of *E. coli* isolated from women with pyelonephritis contain the pyelonephritis-associated pili (pap) gene cluster (O'Hanley, P. M., et al., *N. Engl. J. Med.*, 313:414–447 (1985)). Most patients with pyelonephritis caused by *E. coli* mount a strong immune response to Pap pili. The Pap pili contain adhesions at their tips that enable these bacteria to colonize the urinary tract, id. Most Pap pili-adhesin complexes bind to the P blood group receptor, which is expressed on epithelial cells lining the gut, the bladder, and ureters. Despite our understanding of the role of adhesion in the pathogenesis of UTI, no vaccine is available against UTI. This is also true for many other important microbial pathogens that cause significant morbidity and mortality.

Microbial pathogens, or disease-producing microorganisms, can infect a host by one of several mechanisms. They may enter through a break in the skin, they may be introduced by vector transmission, or they may interact with a mucosal surface. Disease ensues following infection of the host, when the potential of the pathogen to disrupt normal bodily functions is fully expressed.

Each disease-producing microorganism possesses a collection of virulence factors that enhance their pathogenicity and allow them to invade host or human tissues and disrupt normal bodily functions. Infectious diseases have been major killers over the last several thousand years, and while vaccines and antimicrobial agents have played an important role in the dramatic decrease in the incidence of infectious diseases, infectious diseases are still the number one cause of death world-wide.

Environmental conditions within the host are responsible for regulating the expression of most known virulence factors (Mekalanos, J. J., *J. Bacteriol.*, 174:1 (1992)). In the past, scientists would attempt to mimic, in vitro, the environmental conditions within the host in an attempt to identify those genes that encode and are responsible for producing virulence factors. As a result, the identification of many virulence factors was dependent on, and limited by, the ability of researchers to mimic host environmental factors in the laboratory. However, with the advent of in vivo expression technology (IVET) discovered by Mahan, M. J., et al., and disclosed in U.S. Pat. No. 5,434,065 it is now possible to determine which genes are expressed within a host and within which tissues of the host the genes are expressed. Consequently, the molecular mechanisms of the specific pathogenic microorganisms that allow them to circumvent the host's (e.g., human body) immune system and initiate the physiological changes inherent in the disease process can be elucidated, thus allowing for the development of better therapeutic and diagnostic approaches against pathogenic microbes.

Along with water sanitation, prevention of infectious diseases by vaccination is the most efficient, cost-effective, and practical method of disease prevention. No other modality, not even antibiotics, has had such a major effect on mortality reduction and population growth. The impact of vaccination on the health of the world's people is hard to exaggerate. Vaccination, at least in parts of the world, has controlled the following nine major diseases: smallpox, diphtheria, tetanus, yellow fever, pertussis, poliomyelitis, measles, mumps and rubella. In the case of smallpox, the disease has been totally eradicated from the world. The effectiveness of a vaccine depends upon its ability to elicit a protective immune response, which will be generally described below.

The means by which vertebrates, particularly birds and mammals, overcome microbial pathogenesis is complex. Pathogens that invade a host provoke a number of highly versatile and protective systems. If the microbial pathogen or its toxins successfully penetrate the body's outer defenses and reach the bloodstream, then the lymphoid tissue of the spleen, liver, and bone marrow will remove and destroy the foreign material as the blood circulates through these organs. Lymphoid tissue is composed primarily of a meshwork of interlocking reticular cells and fibers. Clinging to the interstices of the tissues are large numbers of leukocytes, more specifically, lymphocyte cells, and other cells in various stages of differentiation, such as plasma cells, lymphoblasts, monocyte-macrophages, eosinophils and mast cells. The two main lymphocytes, T cells and B cells, have different and complementary roles in the mediation of the antigen-specific immune response.

The immune response is an exceedingly complex and valuable homeostatic mechanism that has the ability to recognize foreign pathogens. The initial response to foreign pathogen is called "innate immunity" and is characterized by the rapid migration of natural killer cells, macrophages, neutrophils, and other leukocytes to the site of the foreign pathogen. These cells can either phagocytose, digest, lyse, or secrete cytokines that lyse the pathogen in a short period of time. The innate immune response is not antigen-specific and is generally regarded as a first line of defense against foreign pathogens until the "adaptive immune response" can be generated. Both T cells and B cells participate in the adaptive immune response. A variety of mechanisms are involved in generating the adaptive immune response. A discussion of all the possible mechanisms of generating the adaptive immune response is beyond the scope of this section, however, some mechanisms which have been well-characterized include B cell recognition of antigen and subsequent activation to secrete antigen-specific antibodies and T cell activation by binding to antigen presenting cells.

Microbial organisms can have cell membranes that are recognized as foreign by the immune system. In addition, microbial organisms may also produce toxins or proteins that are also considered foreign by the host's immune system. The first mechanism mentioned above involves the binding of antigen, such as bacterial cell wall or bacterial toxin, to the surface immunoglobulin receptors on B cells. The receptor binding transmits a signal to the interior of the B cell. This is what is commonly referred in the art as "first signal". In some cases, only one signal is needed to activate the B cells. These antigens that can activate B cell without having to rely on T cell help are commonly referred to as T-independent antigens (or thymus-independent antigens). In other cases, a "second signal" is required and this is usually provided by T helper cells binding to the B cell. When T cell help is required for the activation of the B cell to a particular antigen, the antigen is then referred to as T-dependent antigen (or thymus-dependent antigen). In addition to binding to the surface receptors on the B cells, the antigen can also be internalized by the B cell and then digested into smaller fragment within the B cell and presented on the surface of B cells in the context of antigenic peptide-MHC class II molecules. These peptide-MHC class II molecules are recognized by T helper cells that bind to the B cell to provide the "second signal" needed for some antigens. Once the B cell has been activated, the B cells begin to secrete antibodies to the antigen that will eventually lead to the inactivation of the antigen. Another way for B cells to be activated is by contact with follicular dendritic cells (FDCs) within germinal centers of lymph nodes and spleen. The follicular dendritic cells trap antigen-antibody (Ag-Ab) complexes that circulate through the lymph node and spleen and the FDCs present these to B cells to activate them.

Another well-characterized mechanism of adaptive immune response to antigens is the activation of T cells by binding to antigen presenting cells such as macrophages and dendritic cells. Macrophages and dendritic cells are potent antigen presenting cells. Macrophages have a variety of receptors that recognize microbial constituents such as macrophage mannose receptor and the scavenger receptor. These receptors bind microorganisms and the macrophage engulfs them and degrades the microorganisms in the endosomes and lysosomes. Some microorganisms are destroyed directly this way. Other microorganisms are digested into small peptides that are then presented to T cells on the surface of the macrophages in the context of MHC class II-peptide complexes. T cells that bind to these complexes become activated. Dendritic cells are also potent antigen presenting cells and present peptide-MHC class I molecules and peptide-MHC class II molecules to activate T cells.

When a B cell binds to an antigen which has never been encountered, the cell undergoes a developmental pathway called "isotype switching". During the developmental changes, the plasma cells switch from producing general IgM type antibodies to producing highly specific IgG type antibodies. Within this population of cells, some undergo repeated divisions in a process called "clonal expansion". These cells mature to become antibody factories that release immunoglobulins into the blood. When they are fully mature, they become identified as plasma cells, cells that are capable of releasing about 2,000 identical antibody molecules per second until they die, generally within 2 or 3 days after reaching maturity. Other cells within this group of clones never produce antibodies but function as memory cells that will recognize and bind that particular antigen upon encountering the antigen.

As a consequence of the initial challenge by an antigen there are now many more cells identical to the original B cell or parent cell, each of which is able to respond in the same way to the antigen as the original B cell. Consequently, if the antigen appears a second time, it will encounter one of the correct B cells sooner, and since these B cells are programmed for the specific IgG antibody, the immune response will begin sooner, accelerate faster, be more specific and produce greater numbers of antibodies. This event is considered a secondary or anamnestic response. FIG. 1 shows a comparison of the antibody titer present as a result of the primary and secondary responses. Immunity can persist for years because memory cells survive for months or years and also because the foreign material is sometimes reintroduced in minute doses that are sufficient to constantly trigger low-level immune responses. In this way the memory cells are periodically replenished.

Following the first exposure to an antigen the response is often slow to yield antibody and the amount of antibody produced is small, i.e., the primary response. On secondary challenge with the same antigen, the response, i.e., the secondary response, is more rapid and of greater magnitude thereby achieving an immune state equal to the accelerated secondary response following reinfection with a pathogenic microorganism, which is the goal that is sought to be induced by vaccines.

In general, active vaccines can be divided into two general classes: subunit vaccines and whole organism vaccines. Subunit vaccines are prepared from components of the whole organism and are usually developed in order to avoid the use of live organisms that may cause disease or to avoid the toxic components present in whole organism vaccines, as discussed in further detail below. The use of purified capsular polysaccharide material of *H. influenza* type b as a vaccine against the meningitis caused by this organism in humans is an example of a vaccine based upon an antigenic component. See Parks, et al., *J. Inf. Dis.,* 136 (Suppl.):551 (1977); Anderson, et al., *J. Inf. Dis.,* 136 (Suppl.):563 (1977); and Mäkela, et al., *J. Inf. Dis.,* 136 (Suppl.):543 (1977).

Classically, subunit vaccines have been prepared by chemical inactivation of partially purified toxins, and hence have been called toxoids. Formaldehyde or glutaraldehyde have been the chemicals of choice to detoxify bacterial toxins. Both diphtheria and tetanus toxins have been successfully inactivated with formaldehyde resulting in a safe and effective toxoid vaccine which has been used for over 40 years to control diphtheria and tetanus. See, Pappenheimer, A. M., Diphtheria. In: *Bacterial Vaccines* (R. Germanier, ed.), Academic Press, Orlando, Fla., pp. 1–36 (1984); Bizzini, B., Tetanus. Id. at 37–68. Chemical toxoids, however, are not without undesirable properties. In fact, this type of vaccine can be more difficult to develop since protective antigens must first be identified and then procedures must be developed to efficiently isolate the antigens. Furthermore, in some cases, subunit vaccines do not elicit as strong an immune response as do whole organism vaccines due to the lack of extraneous materials such as membranes or endotoxins that may be more immunogenic due to the removal of materials that would otherwise mask the protective antigens or that are immunodominant.

Whole organism vaccines, on the other hand, make use of the entire organism for vaccination. The organism may be killed or alive (usually attenuated) depending upon the requirements to elicit protective immunity. The pertussis vaccine, for example, is a killed whole cell vaccine prepared by treatment of *Bordetella pertussis* cells with formaldehyde. The bacterium *B. pertussis* colonizes the epithelial lining of the respiratory tract resulting in a highly contagious respiratory disease in humans, pertussis or whooping cough, with morbidity and mortality rates highest for infants and young children. The colonization further results in local tissue Damage and systemic effects caused in large part by toxins produced by *B. pertussis*. See, Manclarck, et al., *Pertussis.*, Id. at 64–106. These toxins include endotoxin or lipopolysaccharide, a peptidoglycan fragment called tracheal cytotoxin, a heat-labile dermonecrotizing protein toxin, an adenylated cyclase toxin, and the protein exotoxin pertussis toxin. Vaccination is the most effective method for controlling pertussis, and killed whole-cell vaccines administered with diphtheria and tetanus toxoids (DPT vaccine) have been effective in controlling disease in many countries. See, Fine, et al., Reflections on the Efficacy of *Pertussis* Vaccines, *Rev. Infect. Dis.,* 9:866–883 (1987). Unfortunately, due to the large amounts of endogenous products, discussed above, contained in the pertussis vaccine, many children experience adverse reactions upon injection. Endotoxin, which is an integral component of the outer membrane of the gram-negative organism (as well as all other gram-negative organisms), can induce a wide range of mild to severe side effects including fever, shock, leukocytosis, and abortion. While the side effects associated with pertussis vaccine usually are mild, they may be quite severe. The toxic components present in influenza virus vaccines, however, can induce a strong pyrogenic response and have been responsible for the production of Guillain-Barré syndrome. Since influenza vaccines are prepared by growth of the virus in chick embryos, it is likely that components of the embryo or egg contributes to this toxicity.

The use of killed vaccines has also been described by Switzer et al., U.S. Pat. No. 4,016,253, who applied such a method in preparing a vaccine against *Bordetella bronchiseptica* infection in swine. In a technical paper by Brown, et al., *Br. Med. J.,* 1:263 (1959), the use of killed whole cells is disclosed for preparing a vaccine against chronic bronchitis caused by *Haemophilus influenzae*. The use of killed cells, however, is usually accompanied by an attendant loss of immunogenic potential, since the process of killing usually destroys or alters many of the surface antigenic determinants necessary for induction of specific antibodies in the host. Killed vaccines are ineffective or marginally effected for a number of pathogenic bacteria including *Salmonella* spp. and *V. cholerae*. The parenteral killed whole cell vaccine now in use for *Salmonella typhi* is only moderately effective, and causes marked systemic and local adverse reactions at an unacceptably high frequency.

In the case of intracellular pathogens, such as *Salmonella*, it is generally agreed that vaccines based on live but attenuated microorganisms (live vaccines) induce a highly effective type of immune response. Live attenuated vaccines are comprised of living organisms that are benign but typically can replicate in a host tissues and presumably express many natural target immunogens that are processed and presented to the immune system similar to a natural infection. This interaction elicits a protective response as if the immunized individual had been previously exposed to the disease. Most of the work defining attenuating mutations for the construction of live bacterial vaccines has been performed in *S.* spp. since they establish an infection by direct interaction with the gut associated lymphoid tissue (GALT), resulting in a strong humoral immune response. They also invade host cells and thus are capable of eliciting a strong cell mediated response. Eisenstein (1999) *Intracellular Bacterial Vaccine Vectors* (Paterson, ed., Wiley-Liss, Inc.) pp. 51–109; Hone et al. *Intracellular Bacterial Vaccine Vectors* (Paterson, ed., Wiley-Liss, Inc.) pp. 171–221 (1999); Sirard et al. *Immun. Rev.* 171:5–26 (1999). Ideally, these attenuated microorganisms maintain the full integrity of cell-surface constituents necessary for specific antibody induction yet are unable to cause disease, because, for example, they fail to produce virulence factors, grow too slowly, or do not grow at all in the host. Additionally, these attenuated strains should have substantially no probability of reverting to a virulent wild-type strain. Traditionally, live vaccines have been obtained by either isolating an antigenically related virus from another species, by selecting attenuation through passage and adaptation in a nontargeted species or in tissue cultures, or by selection of temperature-sensitive variants. The first approach was that used by Edward Jenner who used a bovine poxvirus to vaccinate humans against smallpox.

Selecting attenuation through serial passages in a nontargeted species is the second approach that has been widely successful in obtaining live vaccines. For example, Parkman, et al., *N. Engl. J. Med.*, 275:569–574 (1966), developed an attenuated rubella vaccine after serial multiplication in green monkey kidney cells. A measles vaccine has been prepared by passaging the virus in chick embryo fibroblasts. Vaccines against, polio, hepatitis A, Japanese B encephalitis, dengue, and cytomegalovirus have all been prepared following similar procedures.

While animal models, and especially monkeys, are useful in developing live vaccines by serial passages and selection, a large uncertainty as to whether a vaccine is truly non-pathogenic remains until humans have been inoculated. For example, the Daker strain of yellow fever produced from infected suckling mouse brains induced encephalitis in 1% of vaccines. Another crucial problem is the possible contamination of the vaccine by exogenous viruses during passages in cell culture or in animals, especially in monkeys. In light of the more recent knowledge of the potential danger of viruses that can be transmitted from animals to humans, this choice of developing live vaccines is highly questionable.

In contrast to the somewhat haphazard approaches of selecting for live vaccines, discussed above, modem developmental approaches introduce specific mutations into the genome of the pathogen which affects the ability of that pathogen to induce disease. Defined genetic manipulation is the current approach being taken in an attempt to develop live vaccines for various diseases caused by pathogenic microorganisms.

In an effort to develop live vaccines which are safer and elicit a higher immunological response, researchers have focused their efforts to developing live vaccines having specific genetic mutations. Curtiss, in U.S. Pat. No. 5,294,441, discloses that *S. typhi* can be attenuated by constructing deletions in either or both the cya (adenylate cyclase) and crp (cyclic 3',5/-AMP [cAMP] receptor protein) genes. cAMP and the cAMP receptor protein, the products of pleiotropic genes cya and crp, respectively, function in combination with one another to form a regulatory complex that affects transcription of a large number of genes and operons. Consequently, mutating either of these genes results in an attenuated microorganism. Furthermore, microorganisms having single mutations in either the cya or crp genes can not supplement their deficiency by scavenging these gene products from a host to be vaccinated. The crp gene product is not available in mammalian tissues, and while the metabolite produced by the cya gene product, cAMP, is present in mammalian cells, the concentrations present in the cells which *S. typhi* invades are below the concentrations necessary to allow cya mutants to exhibit a wild-type phenotype. See, Curtiss, et al., *Infect. Immun.*, 55:3035–3043 (1987).

Since cAMP is present in host tissues at some level, Curtiss et al. stabilized the Zcya microorganisms by introducing a mutation into the crp gene. Tacket, et al., *Infect. Immun.*, 60(2):563–541 (1992), conducted a study with healthy adult in-patient volunteers which revealed that attenuated *S. typhi* having deletions in the cya and crp genes have the propensity to produce fever and bacteremia (bacteria in the blood).

A similar approach in the attempt to develop live vaccines has been taken by Dr. B. A. D. Stocker. The genes mutated by Stocker produce products which are also not available in host tissues. Stocker, in U.S. Pat. No. 5,210,035, describes the construction of vaccine strains from pathogenic microorganisms made non-virulent by the introduction of complete and non-reverting mutational blocks in the biosynthesis pathways, causing a requirement for metabolites not available in host tissues. Specifically, Stocker teaches that *S. typhi* may be attenuated by interrupting the pathway for biosynthesis of aromatic (aro) metabolites which renders Salmonella auxotrophic (i.e., nutritionally dependent) for p-aminobenzoic acid (PABA) and 2,3-dihydroxybenzoate, substances not available to bacteria in mammalian tissue. These aro-mutants are unable to synthesize chorismic acid (a precursor of the aromatic compounds PABA and 2,3-dihydroxybenzoate), and no other pathways in *Salmonella* exist that can overcome this deficiency. As a consequence of this auxotrophy, the aro-deleted bacteria are not capable of proliferation within the host; however they reside and grow intracellularly long enough to stimulate protective immune responses. In the technical paper authored by Tacket, et al., discussed above, attenuated strains of *S. typhi* were also constructed for use as vaccines by introducing deletions in the aroC and aroD genes, according to Stocker. However, these attenuated strains administered to healthy in-patient volunteers have the propensity to produce fever and bacteremia. (Hone et al. (1987), Hormaeche et al. (1996) *Vaccine* 14:251–259; Hassan and Curtiss (1997) *Avian Dis.* 41:783–791; and Miller et al. (1990) *Res. Microbiol.* 141: 817–821).

Comparative studies between these vaccines have not been rigorously tested and thus the efficacy of these current strains with respect to each other remains unclear. Moreover, toxicity (e.g., symptoms such as diarrhea) of current live bacterial vaccine candidates and the reality that many individuals within the human population are immunocompromised clearly warrants the search for additional vaccines that offer better protection, are longer lasting, and have less toxicity.

Another significant problem with vaccine development is the fact that many pathogenic species are comprised of multiple serotypes that can cause disease in animal hosts vaccinated against a similar pathogenic strain. Previous attempts at developing a long-term cross-protective Salmonella vaccine have often been problematic. For example, live attenuated aroA Salmonella strains have been shown to elicit a cross-protective response against heterologous serotypes (e.g., group B (*typhimurium*) and Group D (*enteritidis* and *dublin*)) strains, but the cross-protective capacity is virtually eliminated after the vaccine is cleared from the immunized animals. Hormaeche et al. (1996).

Like many cellular macromolecules, DNA is subject to postsynthetic "modification" by addition of small chemical moieties to the intact polymer. In a variety of organisms this involves enzymatic addition of methyl ($-CH_3$) groups to DNA, either at position C5 of cytosine or at position N6 of adenosine, shown in FIG. 2. The enzymes responsible for the addition of methyl groups to DNA are known as DNA methyltransferases or DNA methylases. DNA methylases can be divided into two classes: (1) those that methylate cytosine (DNA cytosine methylases); and (2) those that methylate adenine (DNA adenine methylases).

Methylation at adenine residues by DNA adenine methylase (Dam) controls the timing and targeting of important biological processes such as DNA replication, methyl-directed mismatch repair, and transposition (Marinus, *E. coli* and *Salmonella: Cellular and Molecular biology*, 2nd ed., 782–791 (1996)). In addition, in *E. coli*, Dam regulates the expression of operons such as pyelonephritis-associated pili (pap) which are an important virulence determinant in upper urinary tract infections (Roberts, et al., *J. Urol.*, 133:1068–1075 (1985)); van der Woude, et al., *Trends Microbiol.*, 4:5–9 (1996). The latter regulatory mechanism involves formation of heritable DNA methylation patterns, which control gene expression by modulating the binding of regulatory proteins.

There remains a serious need for vaccines that are prepared from live, pathogenic microorganisms which are safe and when administered to a host and will induce an effective type of immune response in the host. It is also very desirable to develop a single vaccine strain that is capable of stimulating an immune response against a different strain (i.e., heterologous serotypes or species). There is also a further need for safe and effective antimicrobial drugs that may be used to treat patients afflicted by disease caused by pathogenic microorganisms.

All references and patent applications cited within this application are herein incorporated by reference in their entirety.

SUMMARY OF THE INVENTION

This invention is based on the discoveries that DNA adenine methylase (Dam) is essential for pathogenesis of bacteria such as *Salmonella*, *Yersinia* and *Vibrio* and that *Salmonella* which have had their Dam expression changed from a normal native level are effective in illiciting an immune response in a subject which generates antibodies which can be isolated. Further these genetically altered bacteria are effective as live attenuated vaccines against murine typhoid fever and elicit an immune response against a second species of *Salmonella*. Further, Dam overproducing *Yersinia* also elicit a protective immune response. Since DNA adenine methylases are highly conserved in many pathogenic bacteria that cause significant morbidity and mortality, Dam derivatives of these pathogens may be effective as live attenuated vaccines. Moreover, since methylation of DNA adenine residues is essential for bacterial virulence, drugs that alter the expression of or inhibit the activity of DNA adenine methylases are likely to have broad antimicrobial action and thus genes that encode DNA adenine methylases and their products are promising targets for antimicrobial drug development.

An aspect of the invention is a pathogenic bacteria which has been altered to up-regulate or down-regulate Dam expression as compared to normal native expression levels of Dam.

Another aspect of the invention is using a Dam altered bacteria to produce antibodies in a subject which is preferably a human.

Yet another aspect of the invention is using a Dam altered bacteria to produce IgG type antibodies which are highly specific to certain infectious pathogens.

Still another aspect of the invention is using Dam altered bacteria to illicit the production of a higher concentration of B cell which produce the specific IgG type antibodies as compared to the concentration of B cells illicited by an infection with unaltered, naturally occurring, pathogenic bacteria.

Another aspect of the invention is using the Dam altered bacteria live vaccines for vaccinating a host against a pathogenic microorganism or a spectrum of similar pathogenic microorganisms.

It is a further object of this invention to provide live vaccines which serve as carriers for antigens, preferably immunogens of other pathogens, particularly microorganisms, including viruses, prokaryotes, and eukaryotes.

It is yet another object of this invention to provide antimicrobial drugs that specifically inhibit DNA adenine methylases and the genes responsible for the production of DNA adenine methylases. Furthermore, the compositions of the present invention comprise natural and synthetic molecules having inhibitory effects on (i) DNA adenine methylase enzymatic activities, (ii) expression of DNA adenine methylases, (iii) DNA adenine methylase activators, (iv) activating compounds for DNA adenine methylase repressors, and/or (v) virulence factors that are regulated by DNA adenine methylases.

Accordingly, in one aspect the invention provides immunogenic compositions comprising live attenuated pathogenic bacteria in a pharmaceutically acceptable excipient, said pathogenic bacteria containing a mutation which alters DNA adenine methylase (Dam) activity such that the pathogenic bacteria are attenuated.

In another aspect, the invention provides immunogenic compositions comprising killed pathogenic bacteria in a pharmaceutically acceptable excipient, said pathogenic bacteria containing a mutation which alters DNA adenine methylase (Dam) activity.

In another aspect, the invention provides attenuated strains of pathogenic bacteria, said bacteria containing a mutation which alters Dam activity such that the bacteria are attenuated.

In another aspect, the invention provides methods of eliciting an immune response in an individual comprising administering any of the compositions described herein (including any of the strains described herein) to the individual in an amount sufficient to elicit an immune response.

In another aspect, the invention provides methods of preventing infection by pathogenic bacteria in an individual, comprising administering any of the immunogenic compositions described herein to the individual in an amount sufficient to reduce (or ameliorate) a symptom associated with infection by the pathogenic bacteria upon infection by the pathogenic bacteria.

In another aspect, the invention provides methods of treating a pathogenic bacterial infection in an individual, comprising administering any of the immunogenic compositions described herein to the individual in an amount sufficient to reduce (or ameliorate) a symptom associated with infection by the pathogenic bacteria in the individual.

In another aspect, the invention provides methods of treating an individual infected with a pathogenic bacteria, comprising administering to the individual a composition comprising an agent which alters Dam activity.

In another aspect, the invention provides methods of eliciting an immune response against a second species of *Salmonella* in an individual, comprising administering to the individual an immunogenic composition comprising an attenuated first species of *Salmonella*, said first species containing a mutation which alters Dam activity such that the *Salmonella* is attenuated. In other embodiments, cross protection is effected by a first species (or strain) of *Yersinia* with respect to a second species (or strain) of *Yersinia*. In some embodiments, cross protection is effected by a first species (or strain) of *Vibrio* with respect to a second species (or strain) of *Vibrio*.

In another aspect, the invention also provides screening methods. The invention includes methods of identifying an agent which may have anti-bacterial activity comprising using an in vitro transcription system to detect an agent which alters the level of transcription from a Dam gene when the agent is added to the in vitro transcription system, wherein an agent is identified by its ability to alter the level of transcription from the Dam gene as compared to the level of transcription when no agent is added.

In another aspect, the invention provides methods of identifying an agent which may have anti-bacterial activity comprising using an in vitro translation system to detect an agent which alters the level of translation from an RNA transcript encoding Dam when the agent is added to the in vitro transcription system, wherein an agent is identified by its ability to alter the level of translation from the RNA transcript encoding Dam as compared to the level of translation when no agent is added.

In another aspect, the invention provides methods of identifying an agent which may have anti-bacterial activity comprising determining whether the agent binds to Dam, wherein an agent is identified by its ability to bind to Dam.

In another aspect, the invention provides methods of identifying an agent which may have anti-bacterial activity comprising the steps of: (a) incubating non-methylated oligonucleotides comprising a Dam binding site with Dam, S-adenosylamethionine, and an agent, wherein said nonmethylated oligonucleotide further comprises a signal; (b) digesting all nonmethylated target sites, thereby releasing said nonmethylated oligonucleotides; and (c) detecting inhibition of DNA adenine methylase as an increase in said signal due to digestion of said nonmethylated target sites, wherein an agent is identified by its ability to cause an increase in signal compared to conducting steps (a), (b), and (c) in absence of agent.

In another aspect, the invention provides methods of identifying an agent which may have anti-bacterial activity comprising the steps of: (a) contacting an agent to be tested with a suitable host cell that has Dam function; and (b) analyzing at least one characteristic which is associated with alteration of Dam function, wherein an agent is identified by its ability to elicit at least one said characteristic.

The invention also provides methods of preparing the vaccines and strains described herein. In one aspect, the invention provides methods of preparing the immunogenic compositions described herein, comprising combining a pharmaceutically excipient with pathogenic bacteria containing a mutation which alters DNA adenine methylase (Dam) activity such that the pathogenic bacteria are attenuated. In some embodiments, the pathogenic bacteria are killed.

In another aspect, the invention provides methods for preparing attenuated bacteria capable of eliciting an immunological response by a host susceptible to disease caused by the corresponding or similar pathogenic microorganism comprising constructing at least one mutation in said pathogenic bacteria wherein a first mutation results in altered Dam function.

Another object of this invention is to provide a method whereby a vaccine may be produced by altering the expression of a global regulator of virulence genes and, more specifically, by altering the expression of DNA adenine methylases.

Another object of this invention is to provide a method whereby a vaccine may be produced by altering the expression of genes regulated by DNA adenine methylases.

In another aspect, the invention provides methods for preparing a live vaccine from a virulent pathogenic bacteria, such as Salmonella, comprising altering the expression of DNA adenine methylases and/or the expression of genes that are regulated by DNA adenine methylases in a virulent strain of a pathogenic bacteria that is, or is similar to, the microorganism desired to be vaccinated against.

It is yet a further object of this invention to provide a method of treating a host, such as a vertebrate infected with a pathogen by administering to the vertebrate a compound or compounds that alter the expression of or inhibit the activity of one or more DNA adenine methylases.

Additional objects, advantages and novel features of this invention shall be set forth in part in the description that follows, and in part will become apparent to those skilled in the art upon examination of the following specification or may be learned by the practice of the invention. The objects and advantages of the invention may be realized and attained by means of the instrumentalities, combinations, compositions, and methods particularly pointed out in the appended claims.

These and other objects, advantages, and features of the invention will become apparent to those persons skilled in the art upon reading the details of the invention as more fully described below.

BRIEF DESCRIPTIONS OF THE DRAWINGS

Figure 4:
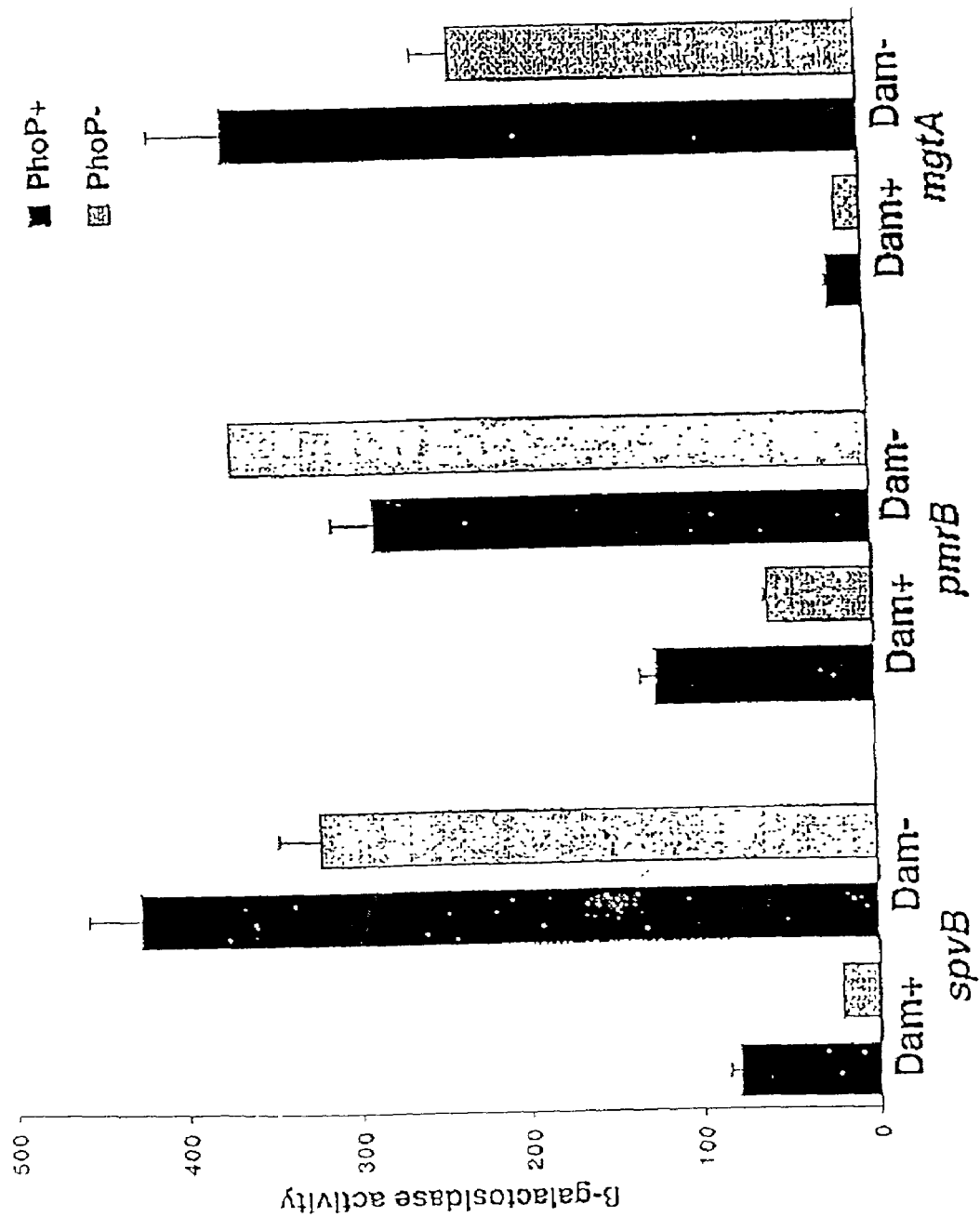

FIG. 4 is a graphic representation illustrating that Dam represses PhoP activated genes. β-galactosidase from S. typhimurium ivi fusions grown in minimal medium. The vertical axis shows β-galactosidase activities (μ-moles of o-nitrophenol (ONP) formed per minute per $A_{600}$ unit per milliliter of cell suspension×$10^3$). The Dam genotype is shown below the horizontal axis, and the phoP genotypes is shown as black (PhoP$^+$) and gray (PhoP$^-$) boxes.

Figure 5:
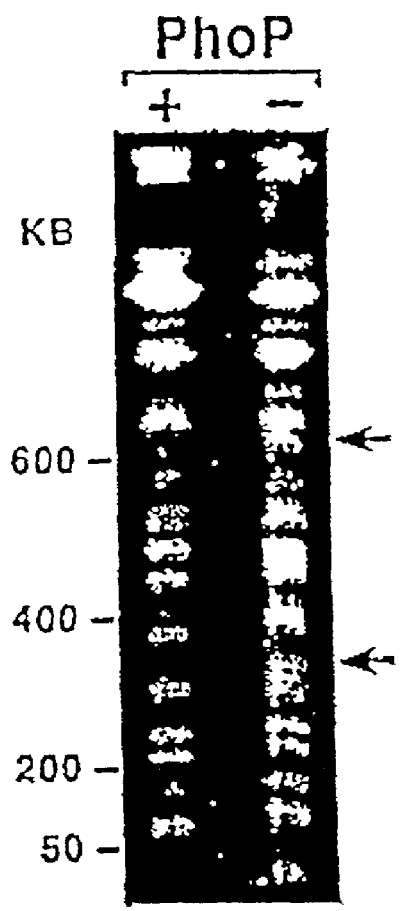

FIG. 5 shows that PhoP affects the formation of Salmonella DNA methylation patterns. DNA methylation patterns formed in PhoP$^+$ and PhoP$^-$ strains grown in minimal medium. The arrows depict DNA fragments that are present in PhoP$^-$ Salmonella but are absent in PhoP$^+$ Salmonella.

Figure 6:
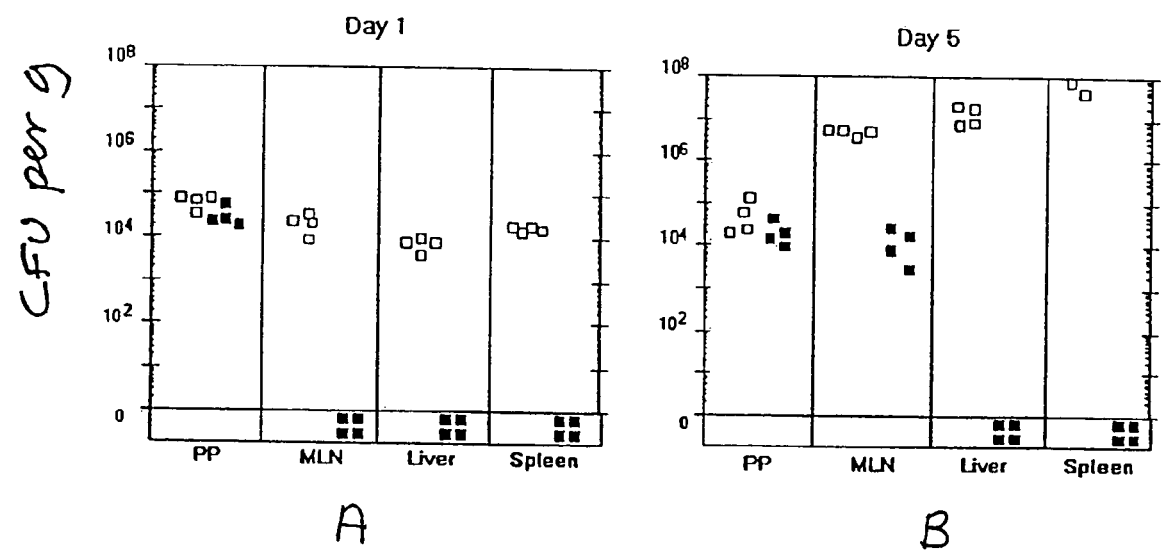

FIG. 6 FIGS. 6A and 6B are graphs depicting the amount and tissue distribution of Salmonella in mice immunized with Dam $^-$ mutants (solid boxes) or not immunized (open boxes) on day 1 and day 5 respectively. PP, Peyer's patches; MLN, mesenteric lymph nodes; CFU, colony forming units.

FIG. 7 FIGS. 7A–7D are graphs depicting amount and tissue distribution of Salmonella in mice immunized with Dam $^-$ mutants (solid boxes) or not immunized (open boxes) on days 1, 5, 14 and 28 respectively. PP, Peyer's patches; MLN, mesenteric lymph nodes; CFU, colony forming units.

Figures 8A, 8B, 8C:
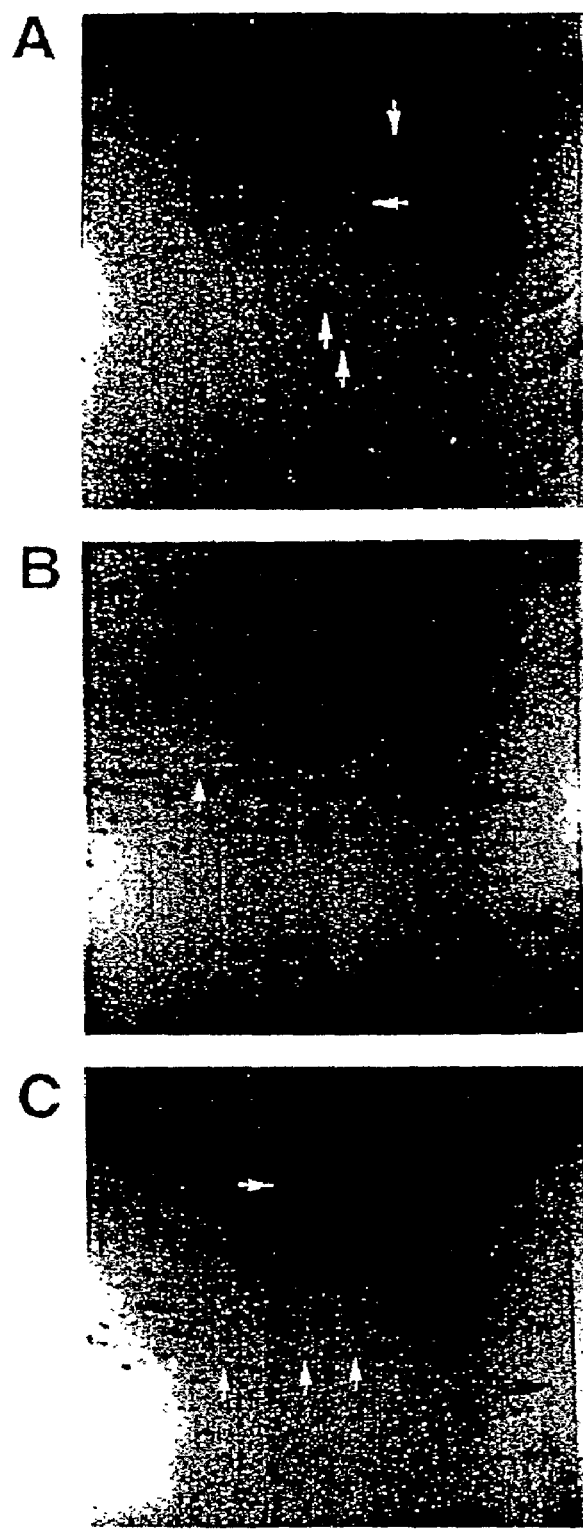

FIGS. 8(A)–(C) are half-tone reproductions of 2D gel electrophoresis of whole-cell protein abstracts of S. typhimurium showing proteins produced in Dam$^-$ strain (Dam non-polar deletion, MT2188; (A)); Dam$^+$ strain (wild type, ATCC 14028 (B)); and Dam$^{+++}$ strain (overproducer, MT2128(C)). Arrows indicate representative examples of proteins that are preferentially expressed in the strains indicated.

Figure 9:
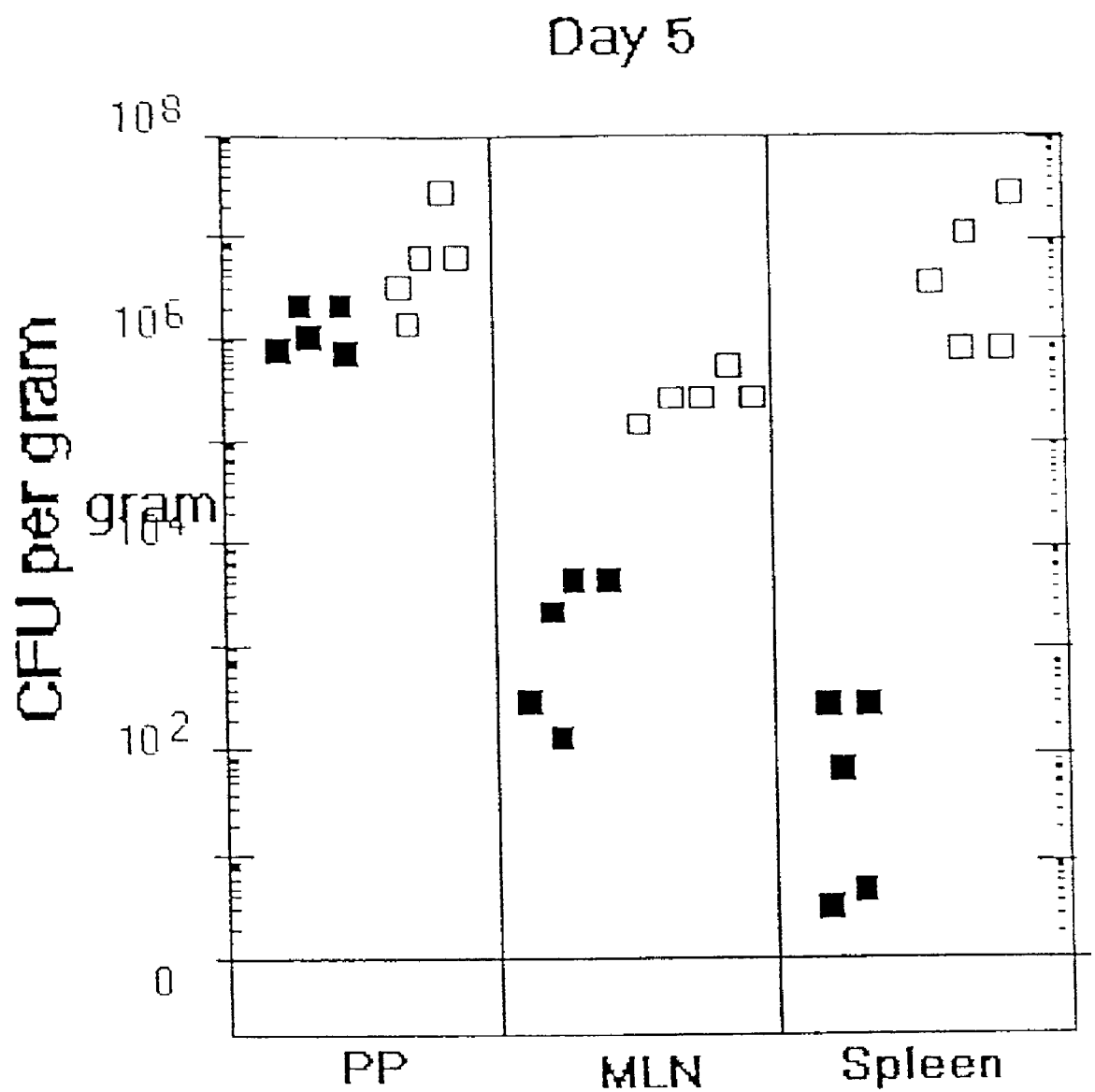

FIG. 9 is a graph depicting the amount and tissue distribution of *Yersinia pseudotuberculosis* in mice immunized with Dam overproducing *Y. pseudotuberculosis* (closed boxes) or not immunized (open boxes) on day 5. PP, Peyer's patches; MLN, mesenteric lymph nodes; CFU, colony forming units.

DETAILED DESCRIPTION OF THE INVENTION

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a bacteria" includes a plurality of such bacteria and reference to "the mutation" includes reference to one or more mutations and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

INVENTION IN GENERAL

We have discovered that the Dam gene and its product enzyme DNA adenine methylase (Dam) are required for bacterial virulence. Despite previous research efforts directed to Dam functions, the critical role of Dam in bacterial virulence, the inventive implications of this role, as well as the ability of a Dam⁻ mutant vaccine to elicit a protective immune response, have not been reported. Previously, all reported Dam mutations from other laboratories used *Salmonella* strain LT2 which is at least 1000-fold less virulent that than the wild type when delivered intraperitoneally. Equipped with the knowledge of this discovery, the present invention is directed towards (a) vaccines having non-reverting genetic mutations in either (i) genes that would alter a function, such as expression, of DNA adenine methylases and/or (ii) genes that are regulated by DNA adenine methylases; (b) a class of inhibitors that are natural and/or synthetic molecules having binding specificity for (i) DNA adenine methylases and/or genes that encode DNA adenine methylases, (ii) activators of DNA adenine methylases and/or activating compounds for repressors of DNA adenine methylases, and (iii) virulence factors that are regulated by Dam; (c) methods for preparing vaccines and inhibitors based on the knowledge that DNA adenine methylase is essential for bacterial pathogenesis; (d) methods of eliciting an immune response using the immunogenic compositions described herein; (e) methods for treating vertebrates with (i) the vaccines of the present invention prior to their becoming infected or (ii) the inhibitors of the present invention after their becoming infected with a pathogenic microorganism; (f) methods of preventing infection using the immunogenic compositions described herein; and (g) screening methods to identify compounds which may be useful therapeutic agents.

The invention relates to the discovery that by altering the level (i.e, the amount) and/or the activity (i.e., resulting effect on the rate and/or total amount of methylation) of Dam in a cell the balance of the cell is upset. Dam plays a pivotal role in bacteria of various strains which strains are described here. This enzyme acts as a global regulator of gene expression and affects a wide range of critical cellular functions, including DNA replication, DNA repair, transposition and segregation of chromosomal DNA. The extraordinary versatility stems from Dam's inherent biochemical activity, which results in adding methyl groups to various sites along the cellular DNA. Dam alters interactions of various regulatory proteins with their designated gene targets and, in the process, effectively controls expression of those genes.

The level and/or activity can be decreased or increased and either will render the cell substantially less virulent as compared to an equivalent, unmodified, wild-type cells. For example, the Dam modified cell is rendered non-pathogenic as compared to a pathogenic wild-type cell large due to the reduced ability of the Dam modified cell to proliferate. This discovery provides an invention which has many aspects and embodiments. For organizational purposes the aspects of the invention are provided in three groups as allows: (1) compositions which comprised Dam altered bacteria; (2) composition which comprises bacteria which are not only Dam altered but which further comprise a sequence which includes a heterologous antigen; and (3) antibacterials or methods of inhibiting bacterial virulence by administering an agent which alters the bacteria's native level of DNA methyltransferase (Dam) activity thereby altering the bacteria's native level of methylation of adenine in a GATC tetranucleotide of the bacterial. The three groups are further described in the following three sections:

Dam Altered Bacteria

An important aspect of this invention is a composition, comprising: a pharmaceutically acceptable excipient; and bacteria with altered DNA adenine methylase activity, which altered DNA adenine methylase activity renders the bacteria non-pathogenic.

In one embodiment of this invention the bacteria are altered by an artificially engineered change in the bacteria's genome which change may be selected from the groups consisting of a deletion, an insertion and a mutation of a native sequence.

In another embodiment of the invention the bacteria are altered by a heterologous nucleotide, which may be operatively inserted into a plasmid and expresses DNA adenine methylase. The composition of the invention may be produced using any bacteria or any organism which comprises genetic material encoding Dam and is particular applicable to organism such as pathogenic bacteria which are less virulent when Dam activity is altered (reduced or increased activity) relative to the normal wild-type level. The reduced virulence can be measured in any desired manner and may be determined by measuring the ability of the altered organism to proliferate. Preferably the ability to proliferate is substantially reduced (e.g. 25%, 50% or 75% or less the rate of proliferation of the unaltered wild-type pathogenic bacteria) in the host organism e.g. in a human.

In one embodiment the bacteria are altered bacteria which are pathogenic in these unaltered state wherein the pathogenic bacteria are selected from the group consisting of *Escherichia, Vibrio, Yersinia* and *Salmonella*. In another specific embodiment the pathogenic bacteria are a salmonella bacteria selected from the group consisting of *S. typhimurium, S. enteritidis, S. typhi, S. abortus-ovi, S. abortus-equi, S. dublin, S. gallinarum*, and *S. pullorum*.

The unmodified pathogenic bacteria used in a composition of the invention may be *E. ccli, V. cholerae, Y. pseudotubercolosis, Shigella, Haemophilus, Bordetella, Neisseria, Pasteurella, Treponema, Streptococcus pneumoniae, Neisseria meningitidis, Haemophilus somnus, Actinobacillus pleuropneumoniae, Pasteurella multocida*, and/or *Mannheimia haemolytica*, and the composition may further comprise an adjuvant.

Another important aspect of the invention is an immunogenic composition, comprising: a pharmaceutically acceptable excipient; and live bacteria, said bacteria comprising altered DNA adenine methylase (Dam) activity wherein the altered activity reduces virulence relative to the bacteria with wild-type Dam activity. The composition may comprise bacteria wherein the Dam activity is altered by a heterologous nucleotide or wherein the Dam activity is altered by a mutation in the bacteria's genome which mutation alters a gene involved in expressing Dam in a manner selected from the group consisting of reduced expression, no expression, over expression, expression of a form of Dam altered from Dam native to the bacteria.

Still another important aspect of this invention is an attenuated strain of a pathogenic bacteria, said bacteria containing a mutation, which alters Dam activity such that the bacteria are attenuated. The mutation may reduce Dam activity, or eliminate Dam activity and the mutation may be a deletion in a dam gene which mutation causes an increase in expression of Dam.

The attenuated strain may be any strain where the native wild-type bacteria comprise Dam and comprises bacteria selected from the group consisting of: *Salmonella enterica* serovars, *E. coli*, Non Typable *Haemophilus influenza, Streptococcus pneumoniae, Helicobacter pylori, Shigella* spp., *Vibrio cholerae, Yersinia* spp., *Neisseria meningitidis, Porphyromonas gingivalis*, and *Legionella pneumophila*. Other bacteria may be bacteria selected from the group consisting of *Streptococcus, pneumoniae, Neisseria meningitidis, Haemophilus somnus, Actinobacillus pleuropneumoniae, Pasteurella multocida*, and *Mannheimia haemolytica*.

Another important aspect of the invention is a method comprising the steps of: administering to a subject capable of generating an immune response a composition comprising a pharmaceutically acceptable excipient an immunogenic dose of altered bacteria with altered DNA adenine methylase (Dam) activity which bacteria are attenuated; and allowing the composition to remain in the subject for a time and under conditions to allow the subject to generate an immune response to the bacteria and produce antibodies specific to the bacteria. In an embodiment the antibodies generated are IgG type antibodies. In a preferred embodiment the IgG antibodies are highly specific for an antigen of the bacteria.

The method of the invention is preferably carried out wherein the bacteria remain in the subject under conditions and for a period of time sufficient to allow for B cells of the subject to undergo isotype switching and further for the B cells to undergo clonal expansion.

In a preferred embodiment the method is carried out wherein an amount of antibodies produced by the subject exceeds 150% of an amount of antibodies which would be produced by the subject administered unaltered bacteria in amount equivalent to the immunogenic dose of altered bacteria. Preferably, the bacteria used are modified germs of pathogenic bacteria selected from the group consisting of *Escherichia, Vibrio, Yersinia* and *Salmonella*.

Another important aspect of the invention is a method of eliciting an immune response in an individual, comprising: administering an immunogenic composition to an individual in an amount sufficient to elicit an immune response wherein the composition comprises a pharmaceutically acceptable carrier and a bacteria comprising a genome characterized by a mutation altering DNA adenine methylase (Dam) activity such that the bacteria is attenuated, allowing the composition to remain in the individual for a time and under conditions to allow the individual to generate an immune response. In a preferred method the bacteria are *Haemophilus*.

Dam Altered Bacteria with Heterologous Antigen(s)

Another important aspect of the invention is an immunogenic composition, comprising: a pharmaceutically acceptable excipient; and live bacteria with DNA adenine methylase (Dam) activity altered relative to wild-type activity of an unaltered pathogenic bacteria, with the alteration being in a manner which renders the bacteria attenuated; and a first heterologous nucleotide sequence operatively inserted in the bacteria which first heterologous sequence expresses a heterologous antigen In one embodiment the Dam activity is altered by an artificially engineered change in the pathogenic bacteria's genome. In another embodiment the Dam activity is altered by a second heterologous nucleotide sequence. Preferably the first heterologous sequence is operatively inserted into a first expression cassette. In another embodiment the second heterologous sequence is operatively inserted into a second expression cassette. Further, the first heterologous sequence maybe operatively inserted into the second expression cassette.

In another aspect of the invention the genetically engineered change is a non-lethal, non-reverting mutation which renders the bacteria attenuated. Further, the heterologous antigen may be any artificial or naturally occurring antigen which causes a subject such as a human to generate an immune response. For example, the heterologous antigen maybe (1) an antigen of a pathogenic virus; (2) an antigen of a pathogenic bacteria; (3) an antigen is a mammalian tumor antigen; and/or (4) an antigen is a mammalian immune disease antigen.

Specifically, the antigen may be any antigen such as an artificial antigen or an antigen of a microorganism which causes an enteric infection such as the antigen of a bacteria selected from the group consisting of Enterotoxigenic *E. coli, Helicobacter pylori, Neisseria meningitis, Salmonella* (non typhoidal), *Salmonella typhi, Shiga* toxin producing *E. coli, Shigella* spp., and *Vibrio cholera*. Alternatively, such an antigen may be an antigen which naturally occurs on a virus selected from the group consisting of Astrovirus, Campylobacter, Coxsackievirus, Echovirus, Norwalk virus, Poliovirus, and Rotavirus.

In yet another embodiment the heterologous antigen is an antigen of a microorganism which causes a respiratory infection such as an antigen of a bacteria selected from the group consisting of Influenza virus, Measles virus, Parainfluenza virus, Paramyxovirus, Respiratory syncytial virus, Rhinovirus, and Rubella virus. Alternatively, such an antigen may be an antigen which naturally occurs on a bacteria selected from the group consisting of *Bordetella pertussis, Chlamydia pneumoniae, Haemophilus influenzae* B, NT *Haemophilus influenzae, Moraxella catarrhalis, Mycobacterium tuberculosis, Mycoplasma pneumoniae, Pseudomonas aeruginosa,* Smallpox, *Staphylococcus aureus,* Streptococci, Group A (GAS), Streptococci, Group B (GBS) and Tetanus.

In still another embodiment the heterologous antigen is an antigen of a microorganism which causes a sexual transmitted disease. For example, the antigen may be present on a mature bacteria selected from the group consisting of *Chlamydia trachomatis, Neisseria gonorrhoeae* and *Treponema pallidum* or on a virus selected from the group consisting, of HIV and Human Papillomavirus.

In a specific embodiment the heterologous antigen is an antigen of a microorganism which causes a herpes virus infection selected from the group consisting of Cytomegalovirus, Epstein-Barr virus, Herpes simplex II, Herpes simplex II and Varicella zoster virus.

In yet another embodiment the heterologous antigen is an antigen of a microorganism which causes a hepatitis virus infection selected from the group consisting of Hepatitis A, Hepatitis B, Hepatitis C, Hepatitis D, Hepatitis E and Hepatitis G.

In still another embodiment the heterologous antigen is an antigen of a microorganism selected from the group consisting of *Leptospira* spp., *Staphylococcus saprophyticus* and Uropathogenic *E. coli*.

In a particular embodiment the heterologous antigen is an antigen of a microorganism which causes a fungal infection which may be an antigen which naturally occurs on a fungi selected from the group consisting of *Aspergillus fumigatus, Blastomyces dermatitidis, Candida* spp., *Coccidioides immitis, Cryptococcus neoformans, Histoplasma capsulatum* and *Paracoccidioides brasiliensis*.

In another embodiment the heterologous antigen is an antigen of a microorganism which causes a parasitic infection which may be an antigen which naturally occurs on a microorganism selected from the group consisting of *Ascaris lumbricoides, Entamoeba histolytica, Enterobius vermicularis, Giardia lamblia, Mycobacterium leprae, Plasmodium* spp., *Schistosoma* spp., *Taenia, Toxoplasma gondii* and *Trichomoniasis vaginalis*.

The invention further includes immunogenic compositions wherein the heterologous antigen is an antigen of a microorganism which causes a vector borne infection which may be created based on an antigen naturally present on a microorganism selected from the group consisting of Arbovirus, *Bacillus anthracis, Borrelia burgdorferi,* Dengue viruses, Japanese encephalitis virus and Rabies virus.

Antibacteria Agents Altering Dam Activity

An important aspect of the invention is a method of reducing bacterial virulence, comprising: contacting bacteria with an agent that alters the bacteria's native level of DNA methyltransferase (Dam) activity thereby altering the bacteria's native level of methylation of adenine in a GATC tetranucleotide of the bacteria, and thereby inhibiting virulence of the bacteria. In accordance with the invention the agent may be designed to reduce the bacteria's native level of DNA methyltransferase activity or to reduce the Dam activity by reducing the bacteria's level of expression of Dam. In specific embodiments the agent reduces the Dam activity by blocking a Dam interaction site, or increases the bacteria's native level of DNA methyltransferase activity. In another embodiment the agent reduces the bacteria's native level of methylated adenine in a GATC tetranucleotide by inhibiting DNA methyltransferase activity, or increases the bacteria's native level of methylated adenine in a GATC tetranucleotide by increasing DNA methyltransferase activity.

The method may be obtained when the agent binds a Dam enzyme, e.g. when the agent binds a native sequence of a bacteria and decreases expression of Dam below a normal level, or when the agent binds a native sequence of a bacteria and increases expression of Dam above a normal level.

In a specific embodiment the agent is designed to alter Dam activity of a pathogenic bacteria selected from the group consisting of *Streptococcus pneumoniae, Neisseria meningitidis, Haemophilus somnus, Actinobacillus pleuropneumoniae, Pasteurella multocida, Mannheimia haemolytica,* NT *Haemophilus influenzae, Helicobacter pylori* and *Shigella* spp. The agent may be designed to alter native Dam activity of a pathogenic bacteria selected from the group consisting of *Escherichia, Vibrio, Yersinia* and *Salmonella*. If the bacteria is salmonella the salmonella bacteria maybe selected from the group consisting of *S. typhimurium, S. enteritidis, S. typhi, S. abortus-ovi, S. abortus-equi, S. dublin, S. gallinarum,* and *S. pullorum*. The agent can reduce virulence of any of *E. coli, V. cholerae, Y. psuedotubercolosis,* or any bacteria selected from the group consisting of *Shigella, Haemophilus, Bordetella, Neisseria, Pasteurella* and *Treponema*.

Another important aspect of the invention is a method of reducing pathogenicity of a pathogenic bacteria, comprising: administering an agent that alters a pathogenic bacteria's native DNA adenine methylase (Dam) activity thereby altering the bacteria's native DNA methylation activity to an extent that the bacteria's pathogenicity is reduced. The method may be carried out by an agent that reduces or increases the Dam activity by reducing or increasing the bacteria's level of expression of Dam, or by an agent that reduces the Dam activity by any means including by blocking a Dam interaction site.

Yet another important aspect of the invention is a method of treating a bacterial infection, comprising the steps of: administering to a subject infected with a pathogenic bacteria a therapeutically effective amount of a composition comprising a pharmaceutically acceptable carrier and an active agent that alters the bacteria's native level of DNA methyltransferase (Dam) activity; and allowing the agent to contact the bacteria for a period of time and under conditions so as to inhibit proliferation of the bacteria. The method may be carried out using an agent that reduces the Dam activity by reducing the bacteria's level of expression of Dam, or by an agent that reduces the Dam activity by blocking a Dam interaction site.

In a preferred embodiment the subject is a mammal, more preferably a human and the agent reduces the level of Dam activity thereby reducing methylation of adenine in a GATC tetranucleotide in the bacteria, thereby inhibiting virulence of the bacteria. Alternatively, the agent increases the level of Dam activity thereby increasing methylation of adenine in a GATC tetranucleotide in the bacteria, thereby inhibiting virulence of the bacteria The administration can be by any route including a route selected from the group consisting of oral, injection, inhalation and topical.

Another important aspect of the invention is a method for treating bacterial infection comprising administering an agent that reduces the level or activity of a DNA methyltransferase thereby reducing methylation of adenine in a GATC tetranucleotide in the bacteria, thereby inhibiting the virulence of the bacteria. The treatment may be carried out wherein the reduction of the level of methylated adenine in a GATC tetranucleotide is effected by inhibiting DNA methyltransferase activity.

Still another aspect of the invention is a composition for controlling bacterial pathogenicity, comprising: a carrier; and a compound that alters native DNA adenine methylase (Dam) activity. Preferably, the carrier is a pharmaceutically acceptable carrier. In an embodiment the agent binds a Dam enzyme. The agent may be an agent which binds a native sequence of a bacteria and decreases expression of Dam below a normal level. Alternatively, the agent may be an agent which binds a native sequence of a bacteria and increases expression of Dam above a normal level.

In a specific embodiment the bacteria is a pathogenic bacteria selected from the group consisting of *Streptococcus pneumoniae, Neisseria meningitidis, Haemophilus somnus, Actinobacillus pleuropneumoniae, Pasteurella multocida, Mannheimia haemolytica*, NT *Haemophilus influenzae, Helicobacter pylori* and *Shigella* spp.

In another specific embodiment the agent alters native Dam activity of a pathogenic bacteria selected from the group consisting of *Escherichia, Vibrio, Yersinia* and *Salmonella*. When the bacteria are salmonella, the salmonella bacteria maybe selected from the group consisting of *S. typhimurium, S. enteritidis, S. typhi, S. abortus-ovi, S. abortus-equi, S. dublin, S. gallinarum*, and *S. pullorum*.

DESCRIPTION OF RESULTS

As described in the Examples, the oral lethal dose of a Dam⁻ mutant (created by an insertion in the Dam gene (Mud-Cm)) in *S. typhimurium* required to kill 50% of the animals ($LD_{50}$) was increased over 10,000-fold and the intraperitoneal (i.p.) $LD_{50}$ was increased-over 1,000 fold compared to wild type (Example 1; Table 1). Further, the highly attenuated Dam⁻ mutants were found to confer a protective immune response in an art-accepted model of murine typhoid fever (Example 2; Table 2). All 17 mice immunized with a *S. typhimurium* Dam⁻ insertion strain survived a wild-type challenge of $10^{+4}$ above the $LD_{50}$, whereas all 12 nonimmunized mice died following challenge. Survival studies comparing Dam⁺ to Dam⁻ *Salmonella* showed that Dam⁻ bacteria were fully proficient in colonization of a mucosal site (Peyer's patches) but showed severe defects in colonization of deeper tissue sites (Example 2; FIG. 6). Without wishing to be bound by theory, the inventors note that one possible explanation of why Dam⁻ elicits protective immune response is because the mutant bacteria grow in intestinal mucosa long enough to elicit an immune response but are unable to invade and/or colonize deeper tissue.

Even more striking, especially in view of the widely held tenet in the art that a vaccine containing one species of *Salmonella* could not elicit an immune response against a second species of *Salmonella*, or at least a significant, lasting immune response against a second strain, especially if the species is attenuated due to mutation in a single gene, our data show such cross-protection. Mice immunized with Dam⁻ *S. typhimurium* (serogroup B) were protected against a heterologous challenge (100 to 1000 $LD_{50}$) with *S. enteritidis* and *S. dublin* (serogroup D) eleven weeks post immunization (Example 3; Table 3B). This protection persisted more than six weeks after the vaccine strain was cleared from the immunized animals (i.e., more than six weeks after the Dam⁻ organisms could not be detected in Peyer's patches, mesenteric lymph nodes, liver and spleen). In contrast to the *Salmonella* cross-protection, no protection was observed against *Yersinia pseudotuberculosis* five weeks post immunization. Similarly, immunization with Dam⁻ *S. enteritidis* conferred cross-protection against *S. typhimurium* and *S. dublin* (Table 3A). Similar results were observed when mice were immunized with Dam overproducing strains of *S. typhimurium* (Table 3C). Although live attenuated *Salmonella* strains have been shown to elicit cross-protection between group B (*typhimurium*) and group D (*enteritidis* and *dublin*) strains (attributed to a shared common LPS antigenic determinant), the cross-protective response is very short-lived, and is virtually eliminated ten to twelve weeks post immunization. Hormaeche et al. (1996) *Vaccine* 251–259.

The ectopic expression in Dam derivatives (i.e., expression of proteins that are normally repressed) as described in Examples 1 and 3 has broad applications to vaccine development. Ectopic expression in Dam derivatives of many pathogens may yield protective and/or cross-protective responses to the parent virulent organisms. *Salmonella* Dam derivatives may have utility as a platform to express passenger bacterial and viral antigens that elicit strong protective immune responses against the cognate pathogen. Since Dam⁻ immunized mice can clear a lethal bacterial load of fully-virulent *Salmonella* organisms, Dam⁻ vaccines may have therapeutic utility to effectively treat a pre-existing infection. Since Dam⁻ derivatives ectopically express multiple proteins, it opens the possibility that vaccines could be constructed in strains that are less harmful to humans, which would exploit the benefits of the high levels of protection elicited by live vaccines while reducing the risk of infection to immunocompromised individuals.

In accordance with the teachings of the specification, the Examples also show that Dam overproducing *Yersinia pseudotuberculosis* and *Vibrio cholerae* are avirulent (Example 8). Even more significantly, Dam overproducing *Yersinia pseudotuberculosis* elicited a protective immune response (Example 9).

The fact that DNA adenine methylase is essential for bacterial pathogenesis, in, for example, *Salmonella* is also of extreme importance, the implications of which are many. First, the Dam gene is highly conserved in pathogenic bacteria, that is, the gene sequence of Dam in one microorganism shares sequence identity with the Dam gene in another microorganism not only within the same species but also across bacterial genera; and second, the Dam gene regulates many genes involved in virulence. Since DNA adenine methylases are highly conserved in many pathogenic bacteria that cause significant morbidity and mortality, such as *Vibrio cholerae* (Bandyopadhyay and Das, *Gene*, 140:67–71 (1994), *Salmonella typhi* (1999-3, Sanger Centre), pathogenic *E. coli* (Blattner, et al., *Science*, 277:1453–1474 (1997), *Yersinia pestis* (1999-3, Sanger Centre), *Haemophilus influenzae* (Fleischmann, et al., *Science*, 269:496–512 (1995), and *Treponema pallidum* (Fraser, et al., *Science*, 281:375–388 (1998)), Dam derivatives of these pathogens may be effective as live attenuated vaccines. Moreover, since Dam is essential for bacterial virulence, Dam inhibitors are likely to have broad antimicrobial action and thus Dam or any gene that alters the expression of Dam is a promising target for antimicrobial drug development.

The implications of this are as follows: (1) it is now possible to rationally develop a class of inhibitors that are natural and/or synthetic molecules having binding specificity for (i) DNA adenine methylases and/or the Dam gene, (ii) Dam activators and/or activating compounds for Dam repressors, and (iii) virulence factors that are regulated by Dam; and (2) it is now possible to produce vaccines having non-reverting genetic mutations in either (i) genes that would alter the expression of DNA adenine methylases and/or (ii) virulence genes that are regulated by DNA adenine methylases. Because Dam is a global regulator of gene expression and many of these regulated genes are conserved in various species and genera, it is highly probable that inhibitors and vaccines based on DNA adenine methylase will give cross-protection. Thus, as discussed above, an inhibitor or a vaccine against one strain, species, serotype and/or group of pathogen would provide protection against a different strain of pathogen.

Compositions described herein may be used for administration to individuals. They may be administered, for example, for experimental purposes, or to obtain a source of anti-bacteria antibody, such as *Salmonella* antibody. They may also be administered to elicit an immune response in an individual as well as to protect an individual from infection or to treat an individual infected with a virulent bacteria, such as *Salmonella*.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, *Molecular Cloning: A Laboratory Manual*, second edition (Sambrook et al., 1989); *Oligonucleotide Synthesis* (M. J. Gait, ed., 1984); *Animal Cell Culture* (R. I. Freshney, ed., 1987); *Methods in Enzymology* (Academic Press, Inc.); *Handbook of Experimental Immunology* (D. M. Wei & C. C. Blackwell, eds.); *Gene Transfer Vectors for Mammalian Cells* (J. M. Miller & M. P. Calos, eds., 1987); *Current Protocols in Molecular Biology* (F. M. Ausubel et al., eds., 1987); *PCR: The Polymerase Chain Reaction* (Mullis et al., eds., 1994); *Current Protocols in Immunology* (J. E. Coligan et al., eds., 1991); *Short Protocols in Molecular Biology* (Wiley & Sons, 1999).

Definitions

"DNA adenine methylase" (Dam) means all and/or any of a group of enzymes which are able to methylate adenine residues in DNA. Dam genes and Dam products encoded by Dam genes are known in the art, and the definition includes Dam enzymes that share significant amino acid similarity to the DNA adenine methylase from *E. coli* (gi 118682) and *Salmonella* (gi 2500157) and that preferentially methylate the sequence "GATC" on DNA, methylating the NT-6 position of adenine. Particular highly conserved DNA sequences encoding a region of Dam are depicted in SEQ ID NOS: 1–4, as described herein. In accordance with art-accepted designations, "Dam" or "Dam gene" indicates a gene encoding a DNA adenine methylase, and "Dam" indicates a DNA adenine methylase (i.e, the polypeptide). For purposes of the present invention a gene is defined as encompassing the coding regions and/or the regulatory regions.

Dam "activity" or "function" means any bio-activity associated with Dam expression or non-expression. Dam activities are described herein. For example, non-expression of Dam leads to repression (or, alternatively, de-repression) of certain genes regulated by Dam; thus, repression (or de-repression) of any of these genes is a Dam activity. As another example, methylation of adenine in DNA (for example, methylation of GATC) is an activity associated with Dam expression and the resultant Dam product; thus, adenine methylation is a Dam activity. Dam "activity" or "function" thus encompasses any one or more bio-activities associated with Dam expression or non-expression. Dam activity may be increased or decreased respectively by enhancing or reducing the level of Dam (i.e. the amount) in a cell.

An "alteration" of Dam activity is any change in any Dam activity, as compared to wild-type Dam function. An "alteration" may or may not be a complete loss of a Dam activity, and includes an increase or decrease of a Dam activity. Bacteria which contain a mutation that alters Dam activity are generally referred to as "Dam derivatives."

"Expression" includes transcription and/or translation, as well as any factor or event which affects expression (such as an upstream event, such as a second gene which affects expression).

A "vaccine" is a pharmaceutical composition for human or animal use, particularly an immunogenic composition which is administered with the intention of conferring the recipient with a degree of specific immunological reactivity against a particular target, or group of targets (i.e., elicit and/or enhance an immune response against a particular target or group of targets). The immunological reactivity, or response, may be antibodies or cells (particularly B cells, plasma cells, T helper cells, and cytotoxic T lymphocytes, and their precursors) that are immunologically reactive against the target, or any combination thereof. For purposes of this invention, the target is primarily a virulent bacteria, such as *Salmonella*. In instances where an attenuated bacteria is used as a carrier, the target may be another antigen as described herein. The immunological reactivity may be desired for experimental purposes, for treatment of a particular condition, for the elimination of a particular substance, and/or for prophylaxis.

"Pathogenic" bacteria are bacteria that are capable of causing disease. "Virulence" is a indicator of the degree of pathogenicity which may be numerically expressed as the ratio of the number of cases of overt infection to total number infected. It is understood that the attenuated bacteria used in the vaccines described herein are modified versions of pathogenic bacteria other than innocuous strains commonly used in laboratories, and the unmodified wild-type pathogenic bacteria are known to and/or are capable of causing disease.

"Attenuated" bacteria used in the compositions described herein are bacteria which exhibit reduced virulence. As is well understood in the art, and described above, virulence is the degree to which bacteria are able to cause disease in a given population. For purposes of the invention, attenuated bacteria have virulence reduced to a suitable and acceptable safety level, as is generally dictated by appropriate government agencies. The degree of attenuation which is acceptable depends on, inter alia, the recipient (i.e., human or non-human) as well as various regulations and standards which are provided by regulatory agencies such as the U.S. Food and Drug Administration (FDA). Most preferably, especially for human use, attenuated bacteria are avirulent, meaning that administration of these organisms cause no disease symptoms. As is well understood in the art, attenuated bacteria are alive, at least at the time of administration.

"Antigen" means a substance that is recognized and bound specifically by an antibody or by a T cell antigen receptor. As is well understood in the art, antigens can include peptides, proteins, glycoproteins, polysaccharides, gangliosides and lipids, as well as portions and/or combinations thereof. Antigens can be those found in nature or can be synthetic.

An "adjuvant" is a chemical or biological agent given an antigen (e.g. given in combination with an attenuated bacteria as described herein) to enhance its immunogenicity. As is known in the art, an "adjuvant" is a substance which, when added to an antigen, nonspecifically enhances or potentiates an immune response to the antigen in the recipient (host).

"Stimulating", "eliciting", or "provoking" an immune response (which can be a B and/or T cell response) means an increase in the response, which can arise from eliciting and/or enhancement of a response.

"Heterologous" means derived from and/or different from an entity to which it is being compared. For example, a "heterologous" antigen with respect to a bacterial strain is an antigen which is not normally or naturally associated with that strain.

An "effective amount" is an amount sufficient to effect a beneficial or desired result including a clinical result, and as such, an "effective amount" depends on the context in which it is being applied. An effective amount can be administered in one or more doses. For purposes of this invention, an effective amount of Dam derivative bacteria (or a composition containing Dam derivative bacteria) is an amount that induces an immune response. In terms of treatment, an effective amount is amount that is sufficient to palliate, ameliorate, stabilize, reverse or slow the progression of a bacterial disease, or otherwise reduce the pathological consequences of the disease. In terms of prevention, an effective amount is an amount sufficient to reduce (or even eliminate) one or more symptoms upon exposure and infection.

"Treatment" is an approach for obtaining beneficial or desired clinical results. Beneficial or desired clinical results include, but are not limited to, alleviation of symptoms, diminishment of extent of disease, stabilized (i.e., not worsening) state of disease, preventing the disease or the spread of disease, delay or slowing of disease progression, amelioration or palliation of the disease state.

"Preventing" disease or infection is part of treating and specifically means a reduction (including, but not limited to, elimination) of one or more symptoms of infection in an individual receiving a composition described herein as compared to otherwise same conditions except for receiving the composition(s). As understood in the art, "prevention" of infection can include milder symptoms and does not necessarily mean elimination of symptoms associated with infection.

An "individual", used interchangeably with "host", is a vertebrate, preferably a mammal, more preferably a human. Mammals include, but are not limited to, farm animals (such as cattle), sport animals, and pets. An "individual" also includes fowl, such as chickens. A "host" may or may not have been infected with a bacteria.

An "agent" means a biological or chemical compound such as a simple or complex organic or inorganic molecule, a polypeptide, a polynucleotide, carbohydrate or lipoprotein. As vast array of compounds can be synthesized, for example oligomers, such as oligopeptides and oligonucleotides, and synthetic organic compounds based on various core structures, and these are also included in the term "agent". In addition, various natural sources can provide compounds for screening, such as plant or animal extracts, and the like. Compounds can be tested singly or in combination with one another.

"Anti-bacterial activity" or "controlling virulence" means that an agent may negatively affect the ability of bacteria to cause disease. For purposes of the invention, an agent which may control virulence is one which alters Dam activity, and may be selected by the screening methods described herein, and further may, upon further study, prove to control bacterial virulence and may even exert therapeutic activity.

"Comprising" and its cognates mean "including".

"A", "an" and "the" include plural references, unless otherwise indicated. For example, "a" Dam means any one or more DNA adenine methylases.

Compositions of the Invention

The compositions described are useful for eliciting an immune response, and/or treating or preventing disease associated with bacterial infection, such as Salmonella, Yersinia, or Vibrio infection. Vaccines prepared from live, pathogenic bacteria are provided for the immunization or for the treatment of a host which is susceptible to disease caused by the corresponding pathogenic bacteria, by a similar pathogenic bacteria of the same strain, species, serotype, and/or group, or by a different bacteria of a different strain, species, serotype, and/or group. The live vaccines produced herein may also serve as carriers for antigens, such as immunogens of other pathogens thereby producing a multiple immunogenic response.

Accordingly, in one embodiment, the invention provides an immunogenic composition comprising live attenuated pathogenic bacteria, such as Salmonella, and a pharmaceutically acceptable excipient, said pathogenic bacteria containing (having) a mutation which alters DNA adenine methylase (Dam) activity such that the pathogenic bacteria are attenuated. In some embodiments, the mutation is in a gene encoding a DNA adenine methylase (Dam), wherein the mutation alters DNA adenine methylase activity. Preferably, as described herein, the mutation is non-reverting. In some embodiments the bacteria comprise a second mutation which results in, or contributes to, attenuation. Preferably the second mutation is independent of the first mutation and is non-reverting.

Dam activity may be increased or decreased, and Dam activity may be altered on any level, including transcription and/or translation. With respect to translation, for example, activity can be altered in any number of ways, including the amount of protein produced and/or that nature (i.e., structure) of the protein produced. For example, a mutation could result in increasing or reducing the amount of Dam produced by the cell (due to affecting transcriptional and/or post-transcriptional events); alternatively, a mutation could give rise to an altered Dam with altered activity. Generating mutations and mutants which alter Dam activity use techniques well known in the art. As an example, Dam production could be lowered by using a promoter which is known to initiate transcription at a lower level. Assays to determine level of transcription from a given transcriptional regulatory element such as a promoter are well known in the art. The native Dam promoter could be replaced with a promoter of lower transcriptional activity; alternatively, a Dam⁻ (in which native Dam gene has been removed) could be used as a basis for integrating a re-engineered Dam gene containing a lower activity promoter to integrate into the genome. Alternatively, a different Dam gene could be used such as a T4 Dam. An example of a Dam over-producer, a pTP166 plasmid that produces *E. coli* Dam at 100-fold wild-type level could be used. Mutations can be within the Dam gene itself (including transcriptional and/or translational regulatory elements) as well as a gene or genes which affect Dam production and/or activity. As is well understood by one skilled in the art, overproduction could be effected using other methods standard in the art such as introduction of a transcriptional regulatory element (such as a promoter) which increases level of transcription (or alteration of the native promoter to effect increased transcription), or introduction of a modification of Dam which increases its half-life. An additional Dam gene may also be introduced, which may or may not be from the same genus or species as the organism in which it is introduced.

Any pathogenic, preferably virulent, strain of bacteria may be used in the immunogenic compositions described herein. In some embodiments, pathogenic bacteria other than *E. coli* are used. In other embodiments, pathogenic *Escherichia* is used, preferably *E. coli*. Because overexpression of Dam can lead to a useful vaccine, Dam gene may or may not be essential, i.e., deletion of Dam may or may not be lethal.

The subject invention is particularly applicable to a wide variety of *Salmonella*, including any of the known groups, species or strains, more preferably groups A, B, or D, which includes most species which are specific pathogens of particular vertebrate hosts. Illustrative of the *Salmonella*-causing disease for which live vaccines can be produced are *S. typhimurium; S. enteritidis, S. typhi; S. abortus-ovi; S. abortus-equi; S. dublin; S. gallinarum; S. pullorum;* as well as others which are known or may be discovered to cause infections in mammals.

Other organisms for which the subject invention may also be employed include *Yersinia* spp., particularly *Y. pestis, Vibrio* spp., particularly *V. cholerae, Shigella* spp., particularly *S. flexneri* and *S. sonnei; Haemophilus* spp., particularly *H. influenzae,* more particularly type b; Bordetella, particularly *B. pertussis;* Neisseria, particularly *N. meningitidis* and *N. gonorrhoeae;* Pasteurella, particularly *P. multocida,* pathogenic *E. coli,* and *Treponema* such as *T. pallidum;* as well as others which are known or may be discovered to cause infections in mammals.

Other pathogenic bacteria are known in the art and include, for example, *Bacillus,* particularly *B. cereus* and *B. anthracis; Clostridium,* particularly *C. tetani, C. botulinum, C. perfringens,* and *C. difficile; Corynebacterium,* particularly *C. diphtheriae; Propionibacterium,* particularly *P. acnes; Listeria,* particularly *L. monocytogenes; Erysipelothrix,* particularly *E. rhusiopathiae; Rothia,* particularly *R. dentocariosa; Kurthia; Oerskovia; Staphylococcus,* particularly *S. aureus, S. epidermidis,* and *S. saprophyticus; Streptococci,* particularly *S. pyogenes, S. agalactiae, S. faecalis, S. faecium, S. bovis, S. equinus,* and *S. pneumoniae; Klebsiella,* particularly *K. pneumoniae; Enterobacter,* particularly *E. aerogenes; Serratia; Proteus,* particularly *P. mirabilis; Morganella,* particularly *M. morganii; Providencia;*

*Pseudomonas,* particularly *P. aeruginosa; Acinetobacter,* particularly *A. calcoaceticus; Achromobacter,* particularly *A. xylosoxidans; Alcaligenes; Capnocytophaga; Cardiobacterium;* particularly *C. hominis; Chromobacterium;* DF-2 Bacteria; *Eikenella,* particularly *E. corrodens; Flavobacterium; Kingella,* particularly *K. kingae; Moraxella; Aeromonas,* particularly *A. hydrophila; Plesiomonas,* particularly *P. shigelloides; Campylobacter,* particularly *C. jejuni, C. fetus* subspecies *fetus, C. coli, C. laridis, C. cinaedi, C. hyointestinalis,* and *C. fennelliae;* Brucella, particularly *B. melitensis, B. suis, B. abortus,* and *B. canis; Francisella,* particularly *F. tularensis; Bacteroides,* particularly *B. fragilis* and *B. melaninogenicus; Fusobacteria; Veillonella; Peptostreptococcus; Actinomyces,* particularly *A. israeli; Lactobacillus; Eubacterium; Bifidobacterium; Arachnia; Legionella,* particularly *L. pneumophila; Gardnerella,* particularly *G. vaginalis; Mobiluncus; Streptobacillus,* particularly *S. moniliformis; Bartonella,* particularly *B. bacilliformis; Calymmatobacterium,* particularly *C. granulomatis; Mycoplasma,* particularly *M. pneumoniae* and *M. hominis; Mycobacterium,* particularly *M. tuberculosis* and *M. leprae; Borrelia,* particularly *B. recurrentis; Leptospira,* particularly *L. interrogans; Spirillum,* particular *S. minor; Rickettsiae,* particularly *R. rickettsii, R. conorii, R. tsutsugamushi,* and *R. akari; Chlamydiae,* particularly *C. psittaci* and *C. trachomatis.*

In another embodiment, the invention provides vaccines used to vaccinate a host comprising a pharmaceutically acceptable excipient and an attenuated form of a pathogenic bacteria, wherein attenuation is attributable to at least one mutation, wherein a first mutation alters either (i) the expression of or the activity of one or more DNA adenine methylases or (ii) the expression of one or more genes regulated by a DNA adenine methylase. The first mutation is preferably non-reverting, and in some embodiments is constructed in a gene whose product activates one or more of said DNA adenine methylases. The first mutation may be constructed in a gene whose product inactivates or decreases the activity of one or more of said DNA adenine methylases. In other embodiments, the first mutation is constructed in a gene whose product represses the expression of said DNA adenine methylases, and the gene product may repress Dam. The vaccine may further comprise a second mutation independent of said first mutation with the second mutation resulting in an attenuated microorganism. The second mutation is preferably non-reverting.

In another embodiment, the invention provides vaccines for provoking an immunological response in a host to be vaccinated comprising a bacterial cell having a mutation, introduced into a gene that disables the ability of said bacterial cell to regulate the expression of a DNA adenine methylase (Dam), which is expressed by the Dam gene.

The ectopic expression of multiple proteins in Dam⁻ vaccines suggests the possibility that killed Dam⁻ organisms may elicit significantly stronger protective immune responses than killed Dam⁺ organisms. Accordingly, in some embodiments, the invention provides immunogenic compositions comprising killed pathogenic bacteria which contain a mutation which alters Dam activity and a pharmaceutically acceptable excipient. Preferably, the mutation is in the Dam gene, and, as described herein, may result in reduction or increase in Dam activity. In some embodiments, the Dam mutation causes death of the bacteria (see Example 7). In other embodiments, the mutation is attenuating, and the bacteria are killed by using methods well known in the art, such as sodium azide treatment and/or exposure to UV. In the instance where the mutation is lethal, the bacteria may further be treated for killing (e.g., using sodium azide and/or UV). Examples of bacteria suitable for these vaccines include, but are not limited to, *Salmonella, Vibrio* (including *V. cholerae*) and *Yersinia* (including *Y. pseudotuberculosis*).

Preferably, the compositions comprise a pharmaceutically acceptable excipient. A pharmaceutically acceptable excipient is a relatively inert substance that facilitates administration of a pharmacologically effective substance. For example, an excipient can give form or consistency to the vaccine composition, or act as a diluent. Suitable excipients include but are not limited to stabilizing agents, wetting and emulsifying agents, salts for varying osmolarity, encapsulating agents, buffers, and skin penetration enhancers. Examples of pharmaceutically acceptable excipients are described in *Remington's Pharmaceutical Sciences* (Alfonso R. Gennaro, ed., 19th edition, 1995).

The invention also comprises immunogenic compositions containing any combination of the mutant strains described herein (whether attenuated or killed), for a given genus, such as *Salmonella*. Since the two different vaccine strains (such as a Dam⁻ and a Dam overproducer) may produce two different repertoires of potentially protective antigens, use of them in combination may elicit a superior immune response.

Pathogenic bacteria, according to this invention, are made attenuated, preferably avirulent, as a result of a non-reverting mutation that is created in at least one gene, which thereby alters a function of a DNA adenine methylase(s). Essentially, the live vaccines provided for, according to the preferred embodiment of the present invention, originate with a pathogenic bacteria. A non-reverting mutation is introduced into a gene of the pathogen, thus altering the expression of DNA adenine methylases. "Non-reverting" mutations generally revert in less than about 1 in $10^8$, preferably less than about 1 in $10^{10}$, or preferably less than about 1 in $10^{15}$, and even more preferably less than 1 in $10^{20}$ cell divisions. Preferably, the mutation is non-leaky; however, regulation of genes by Dam appears to be exquisitely sensitive to Dam concentration. Therefore, over-expression of Dam as well as under expression of Dam results in the attenuation of the pathogen. The mutation is preferably made in the Dam gene itself, however it is contemplated in other embodiments of the present invention, discussed in further detail below, that the vaccines according to the present invention may be produced by mutating a related gene or genes either "upstream" or "downstream" of Dam whose product(s) activate(s) or repress(es) the Dam gene or, in the alternative, a mutation is constructed in at least one virulence gene that is regulated by DNA adenine methylase. The mutation is non-reverting because restoration of normal gene function can occur only by random coincidental occurrence of more than one event, each such event being very infrequent. For example, Dam methylase activity can be down-regulated and/or shut off by introduction of deletions in the promoter or coding region, insertion of transposons or intervening DNA sequences into the promoter or coding regions, use of an antisense oligonucleotide that blocks expression of the Dam gene, or use of a ribozyme that prevents Dam gene expression. Alternatively, the mutation (s) can be an insertion and/or a deletion to an extent sufficient to cause non-reversion.

In the case of a deletion mutation, restoration of genetic information would require many coincidental random nucleotide insertions, in tandem, to restore the lost genetic information. In the case of an insertion plus inversion, restoration of gene function would require coincidence of precise deletion of the inserted sequence and precise re-inversion of the adjacent inverted sequence, each of these events having an exceedingly minute, undetectably low-frequency of occurrence. Thus, each of the two sorts of "non-reverting" mutations has a substantially zero probability of reverting to prototrophy.

Other methods of constructing an insertion in the Dam gene would be well known and obvious to one skilled in the art.

While a single non-reverting mutation provides a high degree of security against possible reversion to virulence, there still remain events which, while unlikely, have a finite probability of occurrence. Opportunities for reversion exist where microorganisms exist in the host which may transfer by conjugation the genetic capability to the non-virulent organism. Alternatively, there may be a cryptic alternative pathway for the production of DNA adenine methylases which by rare mutation or under stress could become operative. Accordingly, in some embodiments, the attenuated bacteria described herein further comprise a second mutation. Live vaccines with two separate and unrelated mutations should be viable and reasonably long lived in the host, provide a strong immune response upon administration to the host, and they may also serve as a carrier for antigens, such as antigens of other pathogens, of other pathogens to provide immune protection from such pathogens.

Examples of *Salmonella typhimurium* attenuating mutations that may serve as secondary mutations for live attenuated vaccine candidates are galE (galactose induced toxicity), pur and aro (aromatic compounds not available in vivo), crp and cya (global changes in gene expression via catabolite control), and phoP (global changes in virulence gene expression) (Hone, et al. (1987), Hormaeche, et al. (1996); Hassan and Curtiss (1997); and Miller, et al. (1990)). Comparative studies between these vaccines have not been rigorously tested and thus the efficacy of these current strains with respect to each other remains unclear. Moreover, toxicity (e.g., symptoms such as diarrhea) of current live bacterial vaccine candidates and the reality that many individuals within the human population are immunocompromised clearly warrants the search for additional vaccines that offer better protection, are longer lasting, and have less toxicity.

In addition to the mutations discussed above, it is desirable that the bacteria for use as a live vaccine have one or more genetic "marker characters" making it easily distinguishable from other bacteria of the same species, either wild strains or other live vaccine strains. Accordingly, one chooses a strain of the pathogen which desirably has a marker for distinguishing the Dam⁻ mutant to be produced from other members of the strain. Alternatively, such a marker can be introduced into the vaccine strain. Various markers can be employed, as discussed previously. The marker(s) used should not affect the immunogenic character of the bacteria, nor should it interfere with the processing of the bacteria to produce the live vaccine. The marker will only alter the phenotype, to allow for recognition of the subject bacteria. For example, Dam mutants are sensitive to the base analog 2-amino purine (Miller, "Experiments in Molecular Genetics" CSHL 1972). Since the Dam gene is genetically linked to cysG, one can use a pool of transposon insertions to transduce a cysG⁻ recipient to cysG⁺. These prototrophs are screened for 2-amino purine sensitivity. To ensure that the insertion is in the Dam gene, the insertion is cloned and the flanking region is sequenced. The marker may be some other nutritional requirements also. Such markers are useful in distinguishing the vaccine strain from wild type strains.

The subject bacteria are then processed to provide one or more non-reverting mutations. The first mutation will alter a Dam function, such as expression, preferably, but not necessarily, by mutating the Dam gene. If a second mutation is desired, a gene, the loss of which is known to result in attenuation, is further mutated. The mutations may be deletions, insertions, or inversions, or combinations thereof. Various techniques can be employed for introducing deletions or insertion inversions, so as to achieve a bacteria having the desired "non-leaky" non-reverting mutation resulting in an altered expression of Dam. The presence of two completely independent mutations, each of which has an extremely low probability of reversion, provides almost absolute assurance that the vaccine strain cannot become virulent.

There are a number of well known techniques which can be employed for disabling or mutating genes, such as the employment of PCR techniques, translocatable elements, mutagenic agents, transducing phages, and DNA-mediated transformation, and/or conjugation. Other methods also known to one with ordinary skill in the art such as recombinant DNA technology may also be employed to successively introduce one or more mutated genes into a single host strain to be used as the vaccine.

After manipulating the bacteria so as to introduce one or more non-reverting mutations into some members of the population, the bacteria are grown under conditions facilitating isolation of the desired mutants, either under conditions under which such mutants have a selective advantage over parental bacteria or under conditions allowing their easy recognition from unaltered bacteria or mutants of other types. The isolated autotrophic mutants are then cloned, screened for virulence, their inability to revert, and their ability to protect the host from a virulent pathogenic strain.

The vaccines can be used with a wide variety of domestic animals, as well as humans. Included among domestic animals which are treated by vaccines today or could be treated, if susceptible to bacterial diseases, are chickens, cows, pigs, horses, goats, and sheep, to name the more important domestic animals.

In accordance with the subject invention, the vaccines are produced by introducing a non-reverting mutation in at least one gene, where each mutation is of a sufficient number of bases in tandem to insure a substantially zero probability of reversion. Preferably, the mutation(s) give rise to non-expression of each mutated gene, in the sense of its total inability to determine production of an active protein, although, as described herein, Dam overproducers may also be made. In addition, the gene chosen will be involved in the expression of a DNA adenine methylase and preferably the gene will be Dam.

The resulting strain will be an avirulent live vaccine having the desired immunogenicity, in that the mutation does not affect the production of the antigens which trigger the natural immune response of the host. Typically, when a wild type pathogen reaches a specific tissue within the host a specific virulence factor or set of virulence factors are expressed as a result of the specific environment to which the pathogen is exposed. It is believed that Dam⁻ mutants constitutively express many virulence factors all at the same time and not within specific tissues. Since the physiological effect of many virulence factors is tissue specific, the virulence factors that are constitutively expressed in the wrong tissues do not initiate the physiological changes inherent in the disease process. These virulence factors do, however, elicit an immune response from the host. The immune system thus encounters these factors in an environment where the factors are not able to initiate the necessary physiological changes in the host to cause disease and the host is able to mount an immune response.

In another embodiment of the present invention, the vaccines are produced by introducing non-reverting mutations in at least two genes, where each mutation is large enough to insure a substantially zero probability of reversion and assurance of the non-expression of each mutated gene. The first gene chosen will be either directly or indirectly involved in the expression of a DNA adenine methylase. The second gene or genes chosen will also result in attenuation regardless of the attenuating effect of the first gene mutation; however, the second mutation can not affect the protective effects of the first mutation. The mutations in the first and second gene may be accomplished as discussed previously.

Accordingly, the invention provides a vaccine for provoking (eliciting) an immunological response in a host to be vaccinated comprising: a bacteria having a first mutation in a first gene that alters the expression of a DNA adenine methylase; and a second mutation in said bacteria which renders said microorganism attenuated independently of said first mutation.

In another embodiment, the invention provides live vaccines which may be used as vectors or carriers for an antigen. The antigen may be any antigen, including an antigen of a bacteria genus or species other than the bacteria used in the non-virulent pathogenic vaccine. The antigen may be added as an admixture, attached or associated with the bacteria, or one or more structural genes coding for the desired antigen(s) may be introduced into the non-virulent pathogenic vaccine as an expression cassette. Accordingly, any of the mutant bacteria described for use in the vaccines described herein may further comprise an expression cassette having one or more structural genes coding for a desired antigen. The expression cassette comprises the structural gene or genes of interest under the regulatory control of the transcriptional and translational initiation and termination regions which naturally border the structural gene of interest or which are heterologous with respect to the structural gene. Where bacterial or bacteriophage structural genes are involved, the natural or wild-type regulatory regions will usually, but not always, suffice. It may be necessary to join regulatory regions recognized by the non-virulent pathogen to structural genes for antigens isolated from eukaryotes and occasionally prokaryotes. Antigens include, but are not limited to, Fragment C of tetanus toxin, the B subunit of cholera toxin, the hepatitis B surface antigen, *Vibrio cholerae* LPS, HIV antigens and/or *Shigella soneii* LPS.

The expression cassette may be a recombinant construct or may be, or form part of, a naturally occurring plasmid. If the expression cassette is a recombinant construct, it may be joined to a replication system for episomal maintenance or it may be introduced into the non-virulent pathogenic bacteria under conditions for recombination and integration into the non-virulent pathogen's chromosomal DNA. Structural genes for antigens of interest may encode bacterial proteins such as toxin subunits, viral proteins such as capsids, or enzyme pathways such as those involved in synthesis of carbohydrate antigens such as lipopolysaccharide (LPS). For example, among the antigens expressed in other live attenuated *Salmonella* vaccines are Fragment C of tetanus toxin, the B subunit of cholera toxin, the hepatitis B surface antigen, and *Vibrio cholerae* LPS. Additionally, the HIV antigens GP120 and GAG have been expressed in attenuated *Mycobacterium bovis* BCG and *Shigella soneii* LPS has been expressed in attenuated *Vibrio cholerae*. The construct or vector may be introduced into the host strain through a number of well known methods such as, transduction, conjugation, transformation, electroporation, transfection, etc.

In another embodiment, live vaccines prepared in accordance with the present invention are prepared having non-reverting mutations in genes that are regulated by an DNA adenine methylase(s), preferably by DNA adenine methylase (Dam). These non-reverting mutations may be prepared as described previously.

In another embodiment, a vaccine is provided for, wherein the bacteria have a mutation which results in the overproduction of Dam, preferably by overproducing DNA adenine methylase (Dam). Methods of producing overproducing bacterial genes are described herein and are known in the art and include, but are not limited to, addition of a plasmid (which may or may not integrate) which carries an additional Dam gene; alteration of a promoter which controls transcription of Dam; alteration in the Dam gene which results in lowered responsiveness to feedback inhibition.

With respect to overproduction, as is well understood by one skilled in the art, alteration of elements(s) could be performed such that reversion to wildtype would be of acceptably low probability. For example, if a plasmid were being used to effect overproduction, stability of that plasmid (such as, for example, by integration) should be assured. If overproduction were effected by insertion of a more active promoter, non-reversion could be assured by, for example, deleting the native promoter. As another example, if Dam is essential for viability, a Dam-producing plasmid may be used in a background in which the native Dam gene has been eliminated. If the plasmid is lost, the organism dies.

The immunogenic compositions described herein may be used with an adjuvant which enhances the immune response against the pathogenic bacteria such as, but not limited to, *Salmonella, Yersinia* and *Vibrio. Adjuvants are especially suitable for killed vaccines, but need not be limited to this use. Suitable adjuvants are known in the art and include aluminum hydroxide, alum, QS*-21 (U.S. Pat. No. 5,057, 540), DHEA (U.S. Pat. Nos. 5,407,684 and 5,077,284) and its derivatives and precursors, e.g., DHEA-S, beta-2 microglobulin (WO 91/16924), muramyl dipeptides, muramyl tripeptides (U.S. Pat. No. 5,171,568) and monophosphoryl lipid A (U.S. Pat. No. 4,436,728; WO 92/16231) and its derivatives, e.g., DETOX™, and BCG (U.S. Pat. No. 4,726, 947). Other suitable adjuvants include, but are not limited to, aluminum salts, squalene mixtures (SAF-1), muramyl peptide, saponin derivatives, mycobacterium wall preparations, mycolic acid derivatives, nonionic block copolymer surfactants, Quil A, cholera toxin B subunit, polyphosphazene and derivatives, and immunostimulating complexes (ISCOMs) such as those described by Takahashi et al. (1990) *Nature* 344:873–875. For veterinary use and for production of antibodies in animals, mitogenic components of Freund's adjuvant can be used. The choice of an adjuvant will depend in part on the stability of the vaccine in the presence of the adjuvant, the route of administration, and the regulatory acceptability of the adjuvant, particularly when intended for human use. For instance, alum is approved by the United States Food and Drug Administration (FDA) for use as an adjuvant in humans.

In some embodiments, the immunogenic composition may also comprise a carrier molecule (with or without an adjuvant). Carriers are known in the art. Pltokin, *Vaccines* 3$^{rd}$ Ed. Philadelphia, W B Suanders Co. (1999). Bacterial carriers (i.e., carriers derived from bacteria) include, but are not limited to, cholera toxin B subunit (CTB); diphtheria toxin mutant (CRM197); diphtheria toxoid; group B streptococcus alpha C protein; meningococcal outer membrane protein (OMPC); tetanus toxoid; outer membrane protein of nontypeable Haemophilus influenzae (such as P6); recombinant class 3 porin (rPorBP of group *B meningococci*, heat-killed *Burcella abortus;* heat-killed *Listeria monocytogeneis;* and *Pseudomonas aeruginosa* recombinant exoprotein A. Another carrier is keyhole limpet hemocyanin (KLH).

The vaccines of the present invention are suitable for systemic administration to individuals in unit dosage forms, sterile parenteral solutions or suspensions, sterile non-parenteral solutions or oral solutions or suspensions, oil in water or water in oil emulsions and the like. Formulations or parenteral and nonparental drug delivery are known in the art and are set forth in *Remington's Pharmaceutical Sciences,* 19th Edition, Mack Publishing (1995). The vaccines may be administered parenterally, by injection for example, either subcutaneously, intramuscularly, intraperitoneally or intradermally. Administration can also be oral, intranasal, intrapulmonary (i.e., by aerosol), and intravenous. Additional formulations which are suitable for other modes of administration include suppositories and, in some cases, oral formulations. The route of administration will depend upon the condition of the individual and the desired clinical effect. For administration to farm animals, such as chickens, cattle and pigs, preferred administration is oral formulations. The formulations for the live vaccines may be varied widely, desirably the formulation providing an enhanced immunogenic response.

The subject vaccines and antimicrobial drugs may be used in a wide variety of vertebrates. The subject vaccines and antimicrobial drugs will find particular use with mammals, such as man, and domestic animals. Domestic animals include bovine, ovine, porcine, equine, caprine, domestic fowl, Leporidate e.g., rabbits, or other animals which may be held in captivity or may be a vector for a disease affecting a domestic vertebrate. Suitable individuals for administration include those who are, or suspected of being, at risk or exposure to bacteria, such as *Salmonella* (*S*. spp.), *Yersinia* and *Vibrio,* as well as those who have been exposed and/or infected. The manner of application of the vaccine or antimicrobial drug may be varied widely, any of the conventional methods for administering being applicable. These include oral application, on a solid physiologically acceptable base or in a physiologically acceptable dispersion, parenterally, by injection, or the like. The dosage of the vaccine or antimicrobial drug will depend inter aha on route of administration and will vary according to the species to be protected. One or more additional administrations may be provided as booster doses, usually at convenient intervals, such as two to three weeks. Since DNA adenine methylases are not present in vertebrates, it is likely that inhibitors of DNA adenine methylases when administered to a vertebrate will display zero or low toxicity. Furthermore, since DNA adenine methylases are enzymes, they will be present in low concentrations within the cell; thus, requiring the administration of lower levels of inhibitors and increasing the likelihood that all the DNA adenine methylases will be inhibited.

Kits and Strains

The invention also provides attenuated strains as described herein. Preferred strains are *Salmonella* strains, *Yersinia* strains, and *Vibrio* strains which contain one or more mutations which alter Dam activity. Similar strains are described herein. Accordingly, in one embodiment, the invention provides attenuated strains of pathogenic bacteria, said bacteria containing a mutation which alters Dam activity such that the bacteria are attenuated. The mutation can be any of those described herein. Preferably, the strain is a *Salmonella* strain. In other embodiments, the strain is a *Vibrio* or *Yersinia*.

The present invention also encompasses kits containing any one or more of the strains and/or vaccine formulations described herein in suitable packaging. The kit may optionally provide instructions, such as for administration to effect any one or more of the following: eliciting an immune response; treatment of infection; prevention of infection; amelioration of one or more symptoms of infection. In some embodiments, the instructions are for administration to a non-human, such as chicken, cattle, pigs, or other farm animal. In other embodiments, the instruction are for administration to a human.

Methods of the invention

The invention also provides methods using the immunogenic compositions described herein, screening methods to identify potentially useful agents which alter Dam activity, as well as methods of preparing the immunogenic compositions described herein.

With respect to any methods involving administration of any of the compositions described herein, it is understood that any one or more of the compositions can be administered, i.e., the compositions can be administered alone or in combination with each other. Further, the compositions can be used alone or in conjunction with other modalities (i.e., clinical intervention), for the purpose of prevention and/or treatment.

Use of immunogenic Compositions for Eliciting an Immune Response, Prevention of and Treating Disease In some embodiments, the invention provides methods using the immunogenic compositions described herein to elicit an immune response in an individual. Generally, these methods comprise administering any one or more of the immunogenic compositions described herein to an individual in an amount sufficient to elicit an immune response. The immune response may be against the particular species and/or strain of bacteria in the composition, or, in other embodiments, may be against a second species and/or strain.

The immune response may be a B cell and/or T cell response. Preferably, the response is antigen-specific, i.e., the response is against the bacteria used in the immunogenic composition (i.e., a response against an antigen associated with the bacteria used is detected). Preferably, the immune response persists in the absence of the vaccine components. Accordingly, in some embodiments, the immune response persists for about any of the following after administration of an immunogenic composition described herein (if given as multiple administrations, preferably after the most recent administration): four weeks, six weeks, eight weeks, three months, four months, six months, one year. In some embodiments, the immune response persists after the pathogenic bacteria used in the immunogenic composition is cleared from the individual. Methods of detection for the presence of the pathogenic bacteria are known in the art.

In order to determine the effect of administration of an immunogenic composition described herein, the individual may be monitored for either an antibody (humoral) or cellular immune response against the bacteria, or a combination thereof, using standard techniques in the art. Alternatively, if an immunogenic composition is already proven to elicit such a response, such monitoring may not be necessary.

For the purpose of raising an immune response, the immunogenic compositions described herein may be administered in an unmodified form. It may sometimes be preferable to modify the bacteria to improve immunogenicity. As used herein, and as well known in the art, "immunogenicity" refers to a capability to elicit a specific antibody (B cell) or cellular (T cell) immune response, or both. Methods of improving immunogenicity include, inter alia, crosslinking with agents such as glutaraldehyde or bifunctional couplers, or attachment to a polyvalent platform molecule. Immunogenicity may also be improved by coupling to a protein carrier, particularly one that comprises T and/or B cell epitopes.

Suitable individuals for receiving the compositions have been described above and likewise apply to these methods. Generally, such individuals are susceptible to exposure to, have been exposed to, and/or display a symptom and/or disease state associated with infection. The individual may or may not have been exposed to, for example, *Salmonella* at the time of administration, and accordingly may or may not have been infected by, for example, *Salmonella* at the time of administration. Preferably, the individual has not been exposed to, for example, *Salmonella*. These principles likewise apply to any of the pathogenic bacteria described herein, including, for example, *Vibrio* and *Yersinia*.

In some embodiments, the invention provides methods of eliciting an immune response to a second species, strain, serotype, and/or group of *Salmonella*, in an individual, comprising administering to the individual any of the immunogenic compositions described herein in an amount sufficient to elicit an immune response to the second species, strain, serotype, and/or group of *Salmonella*. The individual may or may not have been previously exposed to the second species, strain, serotype, and/or group of *Salmonella*. In some embodiments, the second *Salmonella* against which an immune response is elicited is from a second group, such as Group A, B, or D (as compared to the first serotype administered). In other embodiments, the second *Salmonella* against which an immune response is elicited is from a second serotype (as compared to the first serotype administered).

A first and second species may be any species of *Salmonella*, some of which have been described above. In some embodiments, the first species is *S. typhimurium* and the second species is *S. enteritidis*. In some embodiments, the first species is *S. typhimurium* and the second species is *S. dublin*. In other embodiments, the first species is *S. enteritidis* and the second species is *S. typhimurium*. In yet other embodiments, the first species is *S. enteritidis* and the second species is *S. dublin*. Similarly, the first group may be any of the known groups of *Salmonella*, such as Group A, B, or D. The second group may be any known, such as Group A, B, or D (provided that the second group is different from the first group). In other embodiments, the first serotype is different than the second serotype. Serotypes of *Salmonella* are known in the art.

It is understood that an immune response may be elicited against one or more additional antigens (i.e., one or more additional *Salmonella* strains, groups, serotypes, and/or species). Thus, the invention encompasses methods by which an immune response is elicited against a third, fourth, fifth, etc. *Salmonella* strain, group, serotype, and/or species.

The invention also encompasses methods of eliciting an immune response to a second species, strain, serotype and/or group of a pathogenic bacteria in an individual comprising administering to the individual an immunogenic composition comprising an attenuated bacteria which is a Dam derivative amount sufficient to elicit an immune response to a second species, strain, serotype and/or group of the pathogenic bacteria. The pathogenic bacteria may be any pathogenic bacteria, including any described herein (including, but not limited to, *Yersinia* and *Vibrio*).

With respect to the above-described methods of eliciting cross protection, preferably, the immune response persists in the absence of the vaccine components. Accordingly, in some embodiments, the immune response persists for about any of the following after administration of an immunogenic composition described herein (if given as multiple administrations, preferably after the most recent administration): four weeks, six weeks, eight weeks, three months, four months, six months, one year. In some embodiments, the immune response persists after the pathogenic bacteria used in the immunogenic composition is cleared from the individual. Methods of detection for the presence of the pathogenic bacteria are known in the art.

The invention also provides methods of treating a bacterial, preferentially, such as *Salmonella*, infection in an individual. In some embodiments, the invention provides methods of suppressing a disease symptom associated with infection of a virulent bacteria, such as *Salmonella, Vibrio* or *Yersinia*, but may be any pathogenic bacteria, including those described herein. The methods comprise administering any one or more of the compositions described herein in an amount sufficient to suppress a disease symptom associated with infection. Preferentially, the infection is due to *Salmonella*. In other embodiments, the infection is due to *Escherichia*, preferably *E. coli*. In other embodiments, these methods comprise administering any one or more of the compositions described herein in an amount to reduce the amount of pathogenic bacteria, such as *Salmonella*, in an individual (as compared to non-administration).

The vaccines are administered in a manner compatible with the dosage formulation, and in such amount as will be therapeutically effective. The quantity to be administered depends on the individual to be treated, the capacity of the individual's immune system to synthesize antibodies, the route of administration, and the degree of protection desired. Precise amounts of active ingredient required to be administered may depend on the judgment of the practitioner in charge of treatment and may be peculiar to the individual.

In one embodiment, the invention provides methods of treating an individual infected with a pathogenic bacteria, comprising administering to the individual a composition comprising an agent which alters Dam activity. In other embodiments, the invention provides methods of treating a host infected with a pathogenic microorganism (bacteria) comprising (a) administering a compound to the host, wherein said compound alters the expression of or activity of one or more DNA adenine methylases. The compound(s) may (a) bind to one or more DNA adenine methylases thereby altering the activity of said DNA adenine methylases; (b) bind to one or more genes that express a DNA adenine methylase, thereby altering the expression of said DNA adenine methylase(s). The expression of said DNA adenine methylase(s) is/are overactive. Alternatively the expression of said DNA adenine methylase(s) is/are repressed. In some embodiments, the compound is an antisense oligonucleotide having a sequence complementary to one or more DNA adenine methylase gene sequences.

The invention also provides methods of treating a host infected with a pathogenic microorganism (bacteria) comprising administering a compound to the host, wherein said compound binds one or more virulence factors that are regulated by DNA adenine methylases.

In some embodiments, the invention provides methods of preventing bacterial infection, such as *Salmonella, Vibrio* or *Yersinia* infection. In these embodiments, an immune response elicited by the immunogenic composition(s) is protective in the sense that a recipient of the immunogenic composition displays one or more lessened symptoms of infection when compared to an individual not receiving the composition. In other embodiments, a protection is conferred by reducing amount of bacteria, such as *Salmonella, Vibrio* or *Yersinia*, in the individual receiving the composition as compared to not receiving the composition.

In some embodiments, the invention provides methods of suppressing a symptom associated with bacterial infection in an individual (or, alternatively, methods of treating a bacteria infection) comprising administering to the individual a composition comprising an agent which alters Dam activity. A bacteria may be any of those described herein, such as *Salmonella, Vibrio,* or *Yersinia*.

In another embodiment, an antimicrobial drug in accordance with the present invention is prepared which inhibits a DNA adenine methylase(s), preferably DNA adenine methylase (Dam). While the following discussion focuses specifically on the Dam gene and its product, Dam, it is to be understood that this specificity is only for the purpose of simplicity and clarity. It is contemplated that the methods and compositions discussed below are applicable towards (i) any gene that expresses a DNA adenine methylase, (ii) any gene or gene product that regulates a DNA adenine methylase gene, (iii) any gene that is regulated by a DNA adenine methylase, and/or (iv) DNA methylases. Consequently, while a specific gene and gene product, that is Dam and Dam, are discussed below, it is contemplated that other DNA adenine methylase genes and DNA adenine methylases are equivalents of Dam and Dam, respectively, and are thus interchangeable with respect to the discussion which follow.

Inhibition of Dam could be carried out by a number of approaches including use of antisense oligonucleotides to inhibit Dam gene translation, direct inhibitors of Dam enzymatic activity, reduction of Dam levels by isolation of inhibitory compounds for Dam activators and/or activating compounds for Dam repressors, and targeting of virulence factors that are regulated by Dam. The antisense approach has been used previously to inhibit the cytosine methyltransferase (MeTase) from mammalian cells (MacLeod, A. R. and Szyf, M., *J. Biol. Chem.,* 7:8037–8043 (1995)). Transfection of an antisense nucleic acid into adrenocortical cells resulted in DNA demethylation and reduced tumorigenicity associated with MeTase activity.

In another embodiment, the anti-microbial drug activates Dam. Such a compound could effect such activation by, for example, stimulating the Dam promoter, inactivating repressors, and/or extend half-life of Dam.

Screening Assays

The present invention also encompasses methods of identifying agents that may have anti-bacterial activity (and thus may control virulence) based on their ability to alter Dam activity. These methods may be practiced in a variety of embodiments. We have observed that loss or even increase of Dam function results in significantly lower infectivity of *Salmonella* in an art-accepted mouse model. This suggests that modulation of Dam function may result in control of the pathogenesis of various bacteria, including, but not limited to, *Salmonella*, while not affecting host cells. This is especially true since humans do not have a homolog to Dam genes. Further, we have found that Dam is an essential gene in *Vibrio cholerae* and *Yersinia pseudotuberculosis* (Example 7), which indicates that Dam is an excellent drug target in these pathogenic organisms. We have also found, in accordance with the teachings of the specification, that increase in Dam function in *Vibrio cholerae* and *Yersinia pseudotuberculosis* results in significantly lower infectivity of these organisms in an art-accepted mouse model (Example 8). Thus, an agent identified by the methods of the present invention may be useful in the treatment of bacterial infection, especially *Escherichia, Salmonella, Vibrio,* and/or *Yersinia* infection.

The methods described herein are in vitro and cell-based screening assays. In the in vitro embodiments, an agent is tested for its ability to modulate function of Dam. In the cell-based embodiments, living cells having Dam function are used for testing agents. For purposes of this invention, an agent may be identified on the basis of any alteration of Dam function, although characteristics associated with total loss of Dam function may be preferable.

In all of these methods, alteration of Dam function may occur at any level that affects Dam function, whether positively or negatively. An agent may alter Dam function by reducing or preventing transcription of Dam. An example of such an agent is one that binds to the upstream controlling region, including a polynucleotide sequence or polypeptide. An agent may alter Dam function by increasing transcription of Dam RNA. An agent may alter Dam function by reducing or preventing translation of Dam RNA. An example of such an agent is one that binds to the RNA, such as an anti-sense polynucleotide, or an agent which selectively degrades the RNA. Anti-sense approaches to inhibiting Dam have been described above. An agent may alter Dam function by increasing translation of Dam RNA. An agent may compromise Dam function by binding to Dam. An example of such an agent is a polypeptide or a chelator. An agent may compromise Dam function by affecting gene expression of a gene that is regulated by Dam. An example of such an agent is one that alters expression of a Dam-regulated gene on any of the levels discussed above.

The screening methods described as applicable to any pathogenic bacteria having a Dam gene.

In vitro Screening Methods

In in vitro screening assays of this invention, an agent is screened in an in vitro system, which may be any of the following: (1) an assay that determines whether an agent is inhibiting or increasing transcription of Dam; (2) an assay for an agent which interferes with translation of Dam RNA or a polynucleotide encoding Dam, or alternatively, an agent which specifically increases translation of Dam; (3) an assay for an agent that binds to Dam.

For an assay that determines whether an agent inhibits or increases transcription of Dam, an in vitro transcription or transcription/translation system may be used. These systems are available commercially, and generally contain a coding sequence as a positive, preferably internal, control. A polynucleotide encoding Dam is introduced and transcription is allowed to occur. Comparison of transcription products between an in vitro expression system that does not contain any agent (negative control) with an in vitro expression system that does contain agent indicates whether an agent is affecting Dam transcription. Comparison of transcription products between control and Dam indicates whether the agent, if acting on this level, is selectively affecting transcription of Dam (as opposed to affecting transcription in a general, non-selective or specific fashion).

For an assay that determines whether an agent inhibits or increases translation of Dam RNA or a polynucleotide encoding Dam, an in vitro transcription/translation assay as described above may be used, except the translation products are compared. Comparison of translation products between an in vitro expression system that does not contain any agent (negative control) with an in vitro expression system that does contain agent indicates whether an agent is affecting Dam translation. Comparison of translation products between control and Dam indicates whether the agent, if acting on this level, is selectively affecting translation of Dam (as opposed to affecting translation in a general, non-selective or specific fashion).

For an assay for an agent that binds to Dam, Dam is first recombinantly expressed in a prokaryotic or eukaryotic expression system as a native or as a fusion protein in which Dam is conjugated with a well-characterized epitope or protein. Recombinant Dam is then purified by, for instance, immunoprecipitation using anti-Dam antibodies or anti-epitope antibodies or by binding to immobilized ligand of the conjugate. An affinity column made of Dam or Dam fusion protein is then used to screen a mixture of compounds which have been appropriately labeled. Suitable labels include, but are not limited to, fluorchromes, radioisotopes, enzymes and chemiluminescent compounds. The unbound and bound compounds can be separated by washes using various conditions (e.g. high salt, detergent) that are routinely employed by those skilled in the art. Non-specific binding to the affinity column can be minimized by pre-clearing the compound mixture using an affinity column containing merely the conjugate or the epitope. A similar method can be used for screening for agents that competes for binding to Dam. In addition to affinity chromatography, there are other techniques such as measuring the change of melting temperature or the fluorescence anisotropy of a protein which will change upon binding another molecule. For example, a BIAcore assay using a sensor chip (supplied by Pharmacia Biosensor, Stitt et al. (1995) *Cell* 80: 661–670) that is covalently coupled to native Dam or Dam-fusion proteins, may be performed to determine the Dam binding activity of different agents.

With respect to binding Dam, it is understood that suitable fragments of Dam could also be used. For example, if it is known that a particular region of Dam is important for binding to DNA, then this fragment containing or even consisting of this region could be used.

In another embodiment, an in vitro screening assay detects agents that compete with another substance (most likely a polynucleotide) that binds Dam. For instance, it is known that Dam binds a certain DNA motif, namely GATC, which is a Dam target site. An assay could be conducted such that an agent is tested for its ability to compete with binding to this motif(s). Competitive binding assays are known in the art and need not be described in detail herein. Briefly, such an assay entails measuring the amount of Dam complex formed in the presence of increasing amounts of the putative competitor. For these assays, one of the reactants is labeled using, for example, $^{32}P$. One such assay, also encompassed by this invention, is described in more detail below.

Isolation of inhibitors or activators of Dam could be carried out, for example, by screening chemical (Neustadt, et al., *Bioorg. Med. Chem. Lett.,* 8:2395–2398 (1998)) or peptide libraries (Lam, K. S., *Anticancer Drug. Res.,* 12:145–167 (1997)) using a rapid, high throughput assay for Dam. Such inhibitor libraries have already been shown to be effective in blocking the activity of several enzymes (Carroll, C. D., *Bioorg. Med. Chem. Lett.,* 8:3203–3206 (1998)). This Dam assay consists of a double stranded oligonucleotide containing Dam target sites (GATC sequences) with a tethering group on one end (e.g. biotin) and a signal at the other end. This signal could be a radioactive compound such as phosphorous-32, an fluorescent molecule such as fluorescein, or an antigen. The nonmethylated oligonucleotide containing Dam target sites is tethered to a solid surface such as a 96-well microtiter plates containing avidin. Dam enzyme (predetermined to contain just sufficient activity to methylate all of the GATC sites of the target oligonucleotide) is preincubated with inhibitor libraries and then added to each well in the presence of S-adenosylmethionine (SAM). Following an incubation period, sample wells are rinsed in buffer and restriction enzyme MboI is added to digest all nonmethylated GATC sites within the oligonucleotide, thus releasing the signal end of the molecule. Plate wells are then counted (radioactive signal), scanned for fluorescence (fluorescent signal), or incubated with secondary antibody conjugated to an enzyme such as horse radish peroxidase, followed by a non-radioactive substrate of the enzyme. Inhibition of Dam would be detected as a reduction in signal within a sample well due to release of nonmethylated GATC sites. This assay could be used to rapidly screen chemical and peptide libraries for inhibitory activity. The feasibility of such studies has been shown by the isolation of sinefungin, an inhibitor of MeTase activity. Sinefungin is an analog of S-adenosyl-L-methionine (SAM), and acts as a competitive inhibitor of DNA methylation. However, because sinefungin would block all DNA methylases including the mammalian cytosine methylase that require SAM as methyl donor, this drug would not be useful as a chemotherapeutic agent against bacteria.

To isolate activators of Dam, Dam (predetermined to contain sufficient activity to methylate a low percentage of target sites, such as GATC sites, of the target oligonucleotide, for example, 20%) is preincubated with one or more agents (including activator libraries) and then added to each well in the presence of SAM. Activation of Dam would be detected as an increase in signal within the sample well due to methylation of the target sites (such as GATC) and thus prevention of MboI restriction reaction.

Accordingly, in some embodiments, the invention provides methods of identifying an agent which alters or modulates (i.e., an agent which alters Dam function, preferably inhibits Dam function), comprising the steps of (a) tethering a nonmethylated oligonucleotide containing a DNA adenine methylase target site to a solid surface wherein said nonmethylated oligonucleotide has a tethering group on a first end and a signal on a second end; (b) incubating a DNA adenine methylase having sufficient activity to methylate said target sites, preferably all of said target sites, on said nonmethylated oligonucleotide with an agent; inhibitor libraries; (c) adding said incubated DNA adenine methylase to said tethered nonmethylated oligonucleotide in the presence of S-adenosylmethionine; (d) digesting all nonmethylated target sites, thereby releasing said tethered nonmethylated oligonucleotides; and (e) detecting inhibition of DNA adenine methylase as an increase in said signal due to digestion of said nonmethylated target sites. Preferably, the target site is a GATC sequence. The tethering group may be any suitable moiety known in the art, such as biotin. The signal may be due to fluorescence, radioactivity, or an antigen. In some embodiments, the solid surface is a microtiter plate containing avidin. A restriction enzyme, such as MboI, may be used to digest said nonmethylated target sites. If an inhibitor library is used as a source of agents to be tested, the library may comprise biomolecules, such as peptides, or may comprise organic compounds or inorganic compounds.

It is also understood that the in vitro screening methods of this invention include structural, or rational, drug design, in which the amino acid sequence, three-dimensional atomic structure or other property (or properties) of Dam provides a basis for designing an agent which is expected to bind to Dam. Generally, the design and/or choice of agents in this context is governed by several parameters, such as the perceived function of the Dam target (here, binding DNA is one such function), its three-dimensional structure (if known or surmised), and other aspects of rational drug design. Techniques of combinatorial chemistry can also be used to generate numerous permutations of candidate agents. For purposes of this invention, an agent designed and/or obtained by rational drug designed may also be tested in the cell-based assays described below.

Cell-based Screening Methods

In cell-based screening assays, a living cell, preferably a bacterium containing a functioning Dam gene, or a living cell, preferably a bacterium containing a polynucleotide construct comprising a Dam encoding sequence, are exposed to an agent. In contrast, conventional in vitro drug screening assays (as described above) have typically measured the effect of a test agent on an isolated component, such as an enzyme or other functional protein.

The cell-based screening assays described herein have several advantages over conventional drug screening assays: 1) if an agent must enter a cell to achieve a desired therapeutic effect, a cell-based assay can give an indication as to whether the agent can enter a cell; 2) a cell-based screening assay can identify agents that, in the state in which they are added to the assay system are ineffective to alter Dam function, but that are modified by cellular components once inside a cell in such a way that they become effective agents; 3) most importantly, a cell-based assay system allows identification of agents affecting any component of a pathway that ultimately results in characteristics that are associated with alteration of Dam function.

In one embodiment, an agent is identified by its ability to elicit a characteristic associated with an alteration of Dam function in a suitable host cell. A suitable host cell in this context is any host cell in which a Dam function may be observed. Preferably, the host cell is a bacterial cell. Suitable host cells include, but are not limited to, *Salmonella*, *Escherichia*, *Vibrio*, *Yersinia*, and any other bacteria genus and species that contains a Dam gene. One example of an assay uses the pili operon system in *E. coli*, in which level of expression of a reporter is determined. Any bacterial operon system which is responsive to methylation would be suitable for bacterial-based assays, using any of a number of reporter systems known in the art. Levels of transcription and/or translation from such systems in the presence of agent(s) would indicate whether an agent was affecting Dam activity.

In one embodiment, the invention provides methods for identifying an agent that may control virulence comprising the following steps: (a) contacting at least one agent to be tested with a suitable host cell that has Dam function; and (b) analyzing at least one characteristic which is associated with alteration of Dam function (which can be increase, decrease, or loss of Dam function) in said host cell, wherein an agent is identified by its ability to elicit at least one such characteristic. For these methods, the host cell may be any cell in which Dam function has been demonstrated.

For genes that are de-repressed upon loss of Dam function, loss of Dam function may be measured using a reporter system, in which a reporter gene sequence is operatively linked to the Dam-repressed gene of interest. Such repressed genes are described herein, including the examples. As used herein, the term "reporter gene" means a gene that encodes a gene product that can be identified (i.e., a reporter protein). Reporter genes include, but are not limited to, alkaline phosphatase, chloramphenicol acetyl transferase, β-galactosidase, luciferase and green fluorescence protein. Identification methods for the products of reporter genes include, but are not limited to, enzymatic assays and fluorometric assays. Reporter genes and assays to detect their products are well known in the art and are described, for example in Current Protocols in Molecular Biology, eds. Ausubel et al., Greene Publishing and Wiley-Interscience: New York (1987) and periodic updates, as well as Short Protocols in Molecular Biology (Wiley and Sons, 1999). Reporter genes, reporter gene assays and reagent kits are also readily available from commercial sources (Strategene, Invitrogen and etc.) As one skilled in the art would understand, reporter systems may also be used in instances where increase of Dam function results in increase or decrease of expression of another gene(s). The level of reporter with or without agent could indicate alteration of Dam function.

In another embodiment, these methods comprise the following steps: (a) introducing a polynucleotide encoding Dam (or a functional fragment thereof) into a suitable host cell that otherwise lacks Dam function, wherein Dam function is restored in said host cell; (b) contacting said cell of step (a) with at least one agent to be tested; (c) analyzing at least one characteristic which is associated with loss of Dam function, wherein an agent is identified by its ability to elicit at least one said characteristic.

The host cell used for these methods initially lacks Dam function (i.e., lacks Dam function before introduction of polynucleotide encoding Dam). Lacking Dam function may be partial to total. Devising host cells that lack Dam function may be achieved in a variety of ways, including, but not limited to, genetic manipulation such as deletion mutagenesis, recombinant substitution of a functional portion of the gene, frameshift mutations, conventional or classical genetic techniques pertaining to mutant isolation, or alterations of the regulatory domains. For cells in which loss of Dam (or its homolog) function is lethal, a plasmid containing a wild type copy of the Dam is in the cell during the disruption, or mutagenesis, process. If the cells cannot survive without the plasmid containing the wild-type gene, then it is assumed that the loss of Dam function is lethal. Example 7 describes an assay for determining whether a Dam gene is essential.

Introduction of polynucleotides encoding Dam or a functional fragment thereof depend on the particular host cell used and may be by any of the many methods known in the art, such as spheroplasting, electroporation, $CaCl_2$ precipitation, lithium acetate treatment, and lipofectamine treatment.

Polynucleotides introduced into a suitable host cell(s) are polynucleotide constructs comprising a polynucleotide encoding Dam or a functional fragment thereof. These constructs contain elements (i.e., functional sequences) which, upon introduction of the construct, allow expression (i.e., transcription, translation, and post-translational modifications, if any) of Dam amino acid sequence in the host cell. The composition of these elements, such as appropriate selectable markers, will depend upon the host cell being used.

Restoring Dam (or its homolog) function in the host cell(s) may be determined by analyzing the host cell(s) for detectable parameters associated with Dam function (i.e., wild type). These parameters depend upon the particular host cell used. For *Salmonella*, Dam function is associated with any of the following: (a) repression of Dam-regulated genes; (b) virulence; (c) regulation of paf pili expression; (d) lack of sensitivity of certain amino acids. Genes known to be repressed in the presence of Dam in *Salmonella* have been described above. Given methods well known in the art for making reporter constructs (see above), any of these genes could be altered to accommodate a reporter system. Examples of suitable reporter systems have been discussed above.

In some embodiments, a polynucleotide encoding Dam is operatively linked to an inducible promoter. Use of an inducible promoter provides a means to determine whether the agent is acting via a Dam pathway. If an agent causes a characteristic indicative of loss of Dam function to appear in a cell in which the inducible promoter is activated, an observation that the agent fails to elicit the same result in a cell in which the inducible promoter is not activated indicates that the agent is affecting at least one step or aspect of Dam function. Conversely, if the characteristic indicating loss of Dam function is also observed in a cell in which the inducible promoter is not activated, then it can be assumed that the agent is not necessarily acting solely via the Dam functional pathway.

Cell-based screening assays of the present invention can be designed, e.g., by constructing cell lines in which the expression of a reporter protein, i.e., an easily assayable protein, such as β-galactosidase, chloramphenicol acetyltransferase (CAT), green fluorescent protein (GFP) or luciferase, is dependent on Dam function. For example, a gene under Dam control may have reporter sequences inserted within the coding region as described in Example 1. The cell is exposed to a test agent, and, after a time sufficient to effect β-galactosidase expression and sufficient to allow for depletion of previously expressed β-galactosidase, the cells are assayed for the production of β-galactosidase under standard assaying conditions.

Assay methods generally require comparison to a control sample to which no agent is added. Additionally, it may be desirable to use a cell partially or completely lacking Dam function as a control. For instance, if an agent were acting along a Dam pathway, one might expect to see the same phenotype as Dam⁻ cells treated with agents. If an agent were not acting along a Dam pathway, one may expect to see other characteristics that occur in the Dam⁻ cells when treated with the agent.

The screening methods described above represent primary screens, designed to detect any agent that may exhibit anti-bacterial activity. The skilled artisan will recognize that secondary tests will likely be necessary in order to evaluate an agent further. For example, a secondary screen may comprise testing the agent(s) in bacteria of interest if the initial screen has been performed in a host cell other than those bacteria. A further screen is to perform an infectivity assay using the cells that have been treated with the agent(s). An infectivity assay using mice is described in Example 1, and other animal models (such as rat) are known in the art. In addition, a cytotoxicity assay would be performed as a further corroboration that an agent which tested positive in a primary screen would be suitable for use in living organisms. Any assay for cytotoxicity would be suitable for this purpose, including, for example the MTT assay (Promega).

Preparation of Vaccines and Attenuated Bacteria

The invention also provides methods of preparing, or making, the vaccines described herein as well as methods of making the mutant strains (i.e., Dam derivatives) described herein. Any pathogenic bacteria (such as those described herein) may be used. Preparation of vaccines has been discussed above and as such, these methods are included in the invention. It is understood that any of the mutations described herein (including those which increase, decrease, or eliminate Dam activity, including Dam expression) may be used in the methods of preparation of the invention, and are generally not repeated in this section.

In one embodiment, the invention provides methods for preparing an immunogenic composition comprising attenuated bacteria with altered Dam function, comprising combining any of the mutants and/or mutant strains described herein (i.e., Dam derivatives) with a pharmaceutically acceptable excipient. Preferred embodiments include *Salmonella* strains such as those described herein. Particularly preferred are *Salmonella* strains which have mutations which have eliminated Dam activity, such as those deletion mutants described herein. In some embodiments, the bacteria are *Yersinia* or *Vibrio* and the mutation is such that Dam is overproduced.

In one embodiment, the invention provides methods for preparing an attenuated pathogenic bacteria, preferably *Salmonella*, capable of eliciting an immunological response by a individual susceptible to disease caused by the corresponding or similar pathogenic bacteria comprising constructing at least one mutation in said pathogenic bacteria wherein a first mutation results in alteration of Dam function, preferably the altered expression of a Dam. Preferably, the first mutation is introduced into a first gene that expresses Dam. In some embodiments, said first mutation is introduced into a first gene, the expression of which represses or over activates expression of a gene that expresses a DNA adenine methylase enzyme. In some embodiments, said first mutation is introduced into a first gene the expression of which is regulated by a DNA adenine methylase. In other embodiments, a second mutation is created in a gene that is independent of said first mutation, said second mutation causing attenuation of the bacteria. In some embodiments, the pathogenic bacteria are *Vibrio* or *Yersinia*.

In another embodiment, the invention provides methods for preparing an attenuated bacteria capable of eliciting an immunological response by a host susceptible to disease caused by the corresponding virulent bacteria comprising (a) constructing at least one mutation in the Dam gene of a virulent strain of the pathogenic bacteria. In some embodiments, a second mutation is introduced into a second gene which results in attenuation of said bacteria independently of said first mutation.

In another embodiment, the invention provides methods for preparing an attenuated bacteria capable of eliciting an immunological response by a host susceptible to disease caused by the corresponding or similar pathogenic bacteria comprising (a) constructing a first non-reverting mutation in said pathogenic bacteria wherein said first non-reverting mutation alters the expression of or the activity of one or more DNA adenine methylases, and (b) constructing a second non-reverting mutation in said pathogenic bacteria wherein said second non-reverting mutation is independent of said first non-reverting mutation and is attenuating. In some embodiments, the first non-reverting mutation is constructed in a gene whose product activates one or more of said DNA adenine methylases. In some embodiments, the gene product activates DNA adenine methylase. In some embodiments, the first non-reverting mutation is constructed in a gene whose product represses the expression of said DNA adenine methylases. In some embodiments, said gene product represses DNA adenine methylase. In other embodiments, the first non-reverting mutation is constructed in a gene whose product inactivates or decreases the activity of one or more of said DNA adenine methylases by binding directly to one or more of said DNA adenine methylases. In some embodiments, one of said DNA adenine methylases is DNA adenine methylase. In some embodiments, the pathogenic bacteria is a strain of Salmonella, preferably *Salmonella* is *S. typhimurium, S. enteritidis, S. typhi, S. bortus-ovi, S. abortus-equi, S. dublin, S. gallinarum, S. pullorum*. In other embodiments, the pathogenic bacteria are any one of the following: *Yersinia, Vibrio, Shigella, Haemophilus, Bordetella, Neisseria, Pasteurella*, pathogenic *Escherichia, Treponema*. The host may be a vertebrate, such as a mammal, preferably human or a domestic animal. In some embodiments, the vertebrate is a chicken.

In some embodiments, the preparation methods comprise addition of an antigen. For example, the antigen can be added simply to the bacteria in the vaccine, or, alternatively, expression cassette comprising one or more structural genes coding for a desired antigen may be inserted into the attenuated bacteria.

Antigens include, but are not limited to, Fragment C of tetanus toxin, the B subunit of cholera toxin, the hepatitis B surface antigen, *Vibrio cholerae* LPS, HIV antigens and/or *Shigella soneii* LPS.

In another embodiment, the invention provides methods for preparing an attenuated microorganism capable of eliciting an immunological response by a host susceptible to disease caused by the corresponding or similar pathogenic microorganism comprising the steps of (a) constructing a first non-reverting mutation in said pathogenic microorganism wherein said first non-reverting mutation alters the expression of or activity of one or more genes that are regulated by DNA methylases; and (b) constructing a second non-reverting mutation in said pathogenic microorganism wherein said second non-reverting mutation is independent of said first non-reverting and is attenuating.

The above disclosure generally describes the present invention. A more complete understanding can be obtained by reference to the following specific examples which are provided herein for purposes of illustration only and are not intended to be limiting.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Dam *Salmonella* Derivatives are Avirulent

Strain Construction

All *Salmonella typhimurium* strains used were isogenic with American Tissue Culture Collection (ATCC) strain 14028, a smooth virulent strain of *S. typhimurium* referred to as "wild type". Previously, all reported Dam mutations from other laboratories used *Salmonella* strain LT2 which is at least 1000-fold less virulent than the wild type when delivered i.p. See the data in Table 1.

All restriction enzymes and pBR322 were, and can be, purchased from commercial sources, such as Stratagene, 11099 North Torrey Pines Rd., La Jolla, Calif. 92037. Electroporation was carried out with a BioRad Gene Pulser apparatus Model No. 1652098. *S. typhimurium* cells were prepared as per the manufacturer's instructions. Aliquots of competent cells were mixed with an aliquot of the desired plasmid and placed on ice for 1 minute. The mixture was transferred into a cuvette-electrode (0.2 cm) and pulsed once at a field strength of 2.5 KV/cm as per the manufacturer's instructions.

1. Construction of Nonpolar Dam mutant

For construction of a nonpolar Dam mutant, *S. typhimurium* genomic DNA was used as template for the PCR using Pfu polymerase (Stratagene). A 350-bp DNA fragment containing the first 100 codons of Dam was amplified by PCR using the following oligonucleotide pair: 5'-GATTTCTA-GAGTAGTCTGCGGAGCTTTC-3' (SEQ ID NO. 1) (containing an XbaI site at the 5' end) and 5'-GATTCTC-GAGGGTGTTGAACTCCTCGCG-3' (SEQ ID NO. 2) (containing an XhoI site at the 5' end). PCR was carried out in a buffer containing 2.0 mM $Mg^{2+}$ for 30 cycles of 45 seconds at 92° C., 1 minute at 42° C. and 1 minute 30 seconds at 72° C. This procedure was carried out in a DNA Thermal Cycler #N801–0150 (Perkin-Elmer Cetus). The PCR product was then double-digested with XbaI and XhoI. In a second PCR amplification, a 300-bp DNA fragment containing the last 79 codons of Dam was synthesized using the following oligonucleotide pair: 5'-GATTCTCGAGTT-TAGCCTGACGCAACAAG-3' (SEQ ID NO. 3) (containing an XhoI site at the 5' end) and 5'-GATTGCATGCTC-CTTCACCCAGGCGAG-3' (SEQ ID NO. 4) (containing an SphI site at the 5' end). This PCR product was then double digested with XhoI and SphI. The suicide vector pCVD442 (Donnenberg, M. S., et al., *Infect. Immun.*, 59:4310–4317 (1991)), was double digested with XbaI and SphI, band purified, and ligated in a single reaction with the two custom-cut PCR products. An in-frame deletion of 100 internal amino acids of Dam was created, leaving a unique XhoI site at the deletion join point. *E. coli* DH5alpha lambda pir was then transformed selecting ampicillin resistance. DNA from the appropriate ampicillin resistant construct (confirmed by restriction digest) was then used to transform *S. typhimurium* 14028. The integrated pCVD442-containing construct was then segregated on LB 5% sucrose/no salt plates. Segregants were confirmed ampicillin sensitive by printing and Dam⁻ by streaking on LB plates containing 2-aminopurine (0.6 mg/ml) (Dam mutants are 2-AP sensitive). Additionally, PCR was used to confirm the deletion by size in comparison to wild-type sequences. Lastly, the deleted region was cloned into pGP704 and sequence near and at the deletion join point (including the XhoI site) was obtained to confirm that the deletion in fact was in-frame.

The mutation caused by the Dam102 insertion (Dam102::Mud-Cm discussed above) was moved by P22-mediated transduction into virulent Salmonella strain, 14028 to construct strain 2.

2. Mouse Virulent Assays

Virulent properties of all the various *S. typhimurium* strains constructed, as described above, were tested by intraperitoneal or oral inoculations of female BALB/c mice and the results are presented in Table 1 below.

Female BALB/c mice were purchased from Charles River Breeding Laboratories, Inc., (Wilmington, Mass.) and were 6 to 8 weeks of age at initial challenge. *S. typhimurium* strains were grown overnight at 37° C. to stationary phase in Luria Broth (LB). Bacteria were washed once with PBS, then diluted in PBS to the approximate appropriate dilution (samples were plated for colony forming units (CFUs) on LB to give an accurate bacterial count). Mice were challenged with 200 μl of the appropriate bacterial dilutions either intraperitoneally or perorally. For peroral inoculations bacteria were washed and concentrated by centrifugation, the bacteria were then resuspended in 0.2M $Na_2HPO_4$ at pH 8.0, to neutralize stomach acid, and administered as a 0.2 ml bolus to animals under ether anesthesia. For all $LD_{50}$ determinations, 5 mice each were inoculated per dilution. Control mice received PBS only.

All bacterial strains used in this study were derivatives of *S. typhimurium* 14028 (strain 1). Mutant strains were isogenic to wild type and were obtained or constructed as described (Dam102::Mud-Cm and mutS121::Tn10 alleles are in LT2 (strain 7), a highly attenuated (virtually non-pathogenic) strain as shown in Table 2, were obtained from Dr. John Roth (University of Utah) and Dr. Tom Cebula (The Food and Drug Administration), respectively; these alleles (and additional alleles below) were transduced into virulent strain, 14028, constructing strains 2 and 5, respectively. DamΔ232 (strain 3) was constructed using internal oligonucleotides that serve as PCR primers designed to construct an in-frame 300 bp deletion of defined Dam sequence. dcm1::Km was constructed according to (Julio, S. M., et al., *Molec. Gen. Genet.*, 258:178–181(1998)); the Km resistance determinant is associated with an internal deletion of >600 bp of dcm sequence. The lrp31::Km is a null insertion in the lrp gene (strain 6). The Dam overproducing strain (strain 4) contains *E. coli* Dam on a recombinant plasmid (pTP166) in a wild-type background (Marinus, et al., *Gene*, 28:123–125 (1984).

For in vivo competition studies, bacteria were treated as discussed above, then mutant cells were mixed with wild-type cells at a 1:1 ratio (approximate input bacteria was 500 mutant+500 wild type). Actual ratios were determined by first plating input bacteria on LB, then scoring one hundred colonies for resistance to appropriate antibiotic(s). Bacteria were injected intraperitoneally into at least five BALB/C mice (with a one-to-one ratio of mutant to wild type as described (Conner, C. P., et al., *Proc. Natl. Acad. Sci. USA*, 14:4641–4645 (1998)), then after 4–5 days, when mice appeared moribund, they were sacrificed and their spleens isolated, homogenized, diluted and plated. Again, the ratio of mutant to wild-type was determined by scoring one hundred colonies for the mutant phenotype. The competitive index is the ratio of mutant to wild-type bacteria recovered and essentially reflects how fit the mutant strain is compared to the wild-type strain. Thus, those strains that display a competitive index of less than 0.0001 reflect the fact that no mutant strains were recovered from the spleens. Consequently, the mice died as a result of the wild-type strains.

The advantage of the $LD_{50}$ assay is that it quantitates large virulence defects. The disadvantage is that it lacks sensitivity and thus subtle but important virulence contributions are often missed. The competitive index is the ratio of mutant to wildtype bacteria recovered from infected tissues after co-inoculation. The competitive index is very sensitive allowing subtle virulence contributions to be detected. However, because of its sensitivity, quantitation of the differences in virulence between two mutants that confer large defects is problematic. Thus the use of the $LD_{50}$ and competitive index assays in concert are an effective means to quantitate both large and subtle virulence defects. The competitive index is an additional indicator of how fit the mutant strains are compared to wild type, but does not necessarily directly correlate with full virulence.

The results are shown in Table 1. $LD_{50}$ is the dose required to kill 50% of infected animals ($LD_{50}$) assay for each of these strains was compared to that of wild type (strain 1; (ND, Not determined)). The peroral $LD_{50}$ via gastrointubation for all derivatives was determined by infecting at least twelve BALB/c mice; the intraperitoneal (i.p.) $LD_{50}$ was determined by infecting at least six mice.

TABLE 1

| Strain* | Genotype | Oral $LD_{50}$ | I.P. $LD_{50}$[#] | Competitive Index (I.P.)[a] |
|---|---|---|---|---|
| 1 | "wild type" | $>10^{+5}$ | $<10$ | — |
| 2 | dam102::Mud-Cm | $>10^{+9}$ | $>10^{+4}$ | $<10^{-4}$ |
| 3 | DamΔ232 (non-polar deletion) | $>10^{+9}$ | $>10^{+4}$ | $<10^{-4}$ |
| 4 | wild type, (pTP166) (Dam overproducer) | $10^{+8}$ | $>10^{+4}$ | $<10^{-4}$ |
| 5 | mutS121::Tn10 | $10^{+5}$ | ND | 0.9 |
| 6 | lrp31::Km | $10^{+5}$ | ND | 10.0 |
| 7 | LT2 | ND | $2 \times 10^{+4}$ | ND |

Since the Dam insertion could decrease the expression of downstream genes (polar effects), an in-frame, nonpolar Dam deletion was constructed, and was shown to have the same reduced virulence as the Dam insertion. Thus, the attenuation was specifically due to the lack of Dam. Furthermore, intraperitoneal inoculation of mice with equal numbers of Dam$^+$ and Dam$^-$ Salmonella showed that Dam$^-$ mutants were completely eliminated during growth in the mouse (competitive index assay). Similar results were obtained with strain 4 (Table 1) that overproduces Dam from a recombinant plasmid, suggesting that precise levels of the Dam methylase are required for full virulence. These results show for the first time that the Dam methylase is essential for bacterial pathogenesis.

Dam could affect Salmonella virulence via an increase in mutation rate caused by abrogation of methyl-directed mismatch repair (MDMR). Since MutS plays an essential role in MDMR, it was determined whether mutS Salmonella were attenuated for virulence. The data in Table 1, above, show that in both the oral $LD_{50}$ and the competitive index virulence assays, mutS Salmonella were identical to wild type, indicating that Dam does not affect pathogenesis via the MDMR pathway. Since MutS$^-$ strains show higher levels of DNA exchange between species than MutS$^+$ strains, they more readily acquire new virulence determinants (Marinus, *E. coli and Salmonella: Cellular and Molecular Biology*, 2nd ed., 782–791 (1996)). The fact that MutS$^-$ strains are fully virulent could explain the high frequency at which mutS *E. coli* and *Salmonella* mutants are found amongst clinical isolates (LeClerc, et al., *Science*, 274:1208–1211 (1996)).

Dam and Lrp directly regulate the expression of Pap pili, which are essential for virulence of uropathogenic *E. coli* (O'Hanley et al., *J. Clin. Invest.*, 75:347–360 (1985); and Roberts, et al., *J. Urol.*, 133:1068–1075 (1985)). To determine if Dam affects *Salmonella* virulence through an Lrp-mediated pathway, Lrp$^-$ *Salmonella* were analyzed (Table 1). *Salmonella* lacking Lrp were fully virulent based on the $LD_{50}$ and competitive index assays. These data show that *Salmonella* Lrp is not a virulence factor in mice.

The results discussed above show that adenine methylation is critical for *Salmonella* pathogenesis. DNA methylation of cytosine residues appears to be important for the regulation of biological processes in both plants and animals. Although *Salmonella* contain a DNA cytosine methylase (Dcm), the role of cytosine methylation in this organism is unclear. The dcm$^-$ mutant (dcm1::Km) was virulent in the $LD_{50}$ and competitive index assays, data not shown. These results demonstrate that methylation of adenine but not cytosine residues is required for *Salmonella* pathogenesis.

Figure 1:
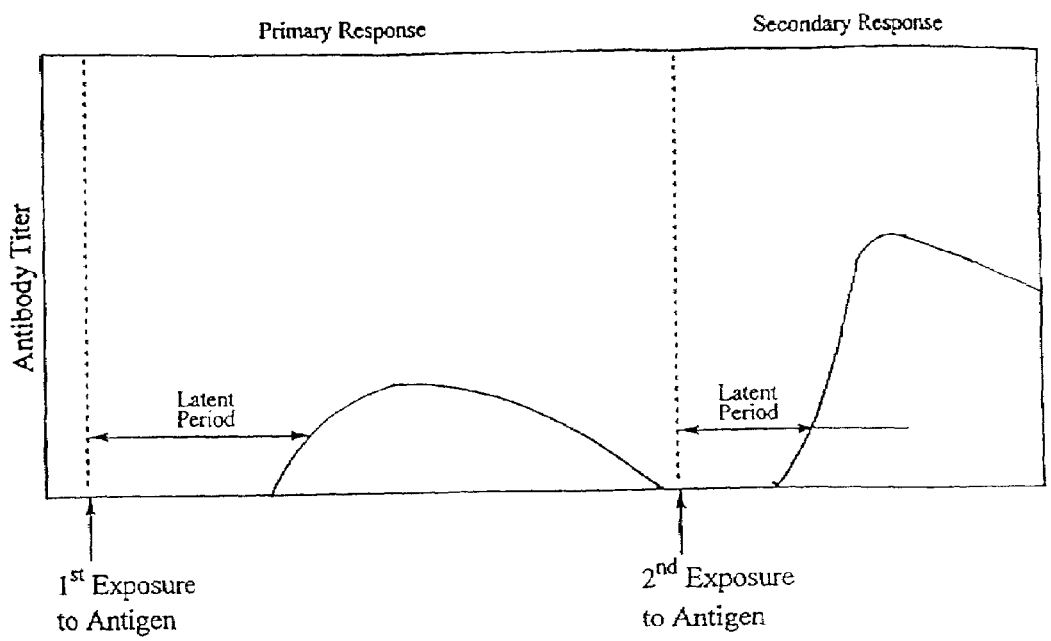
FIG. 1 is a graphic representation of the levels of antibody present following the primary and secondary immune responses.
Figure 2:
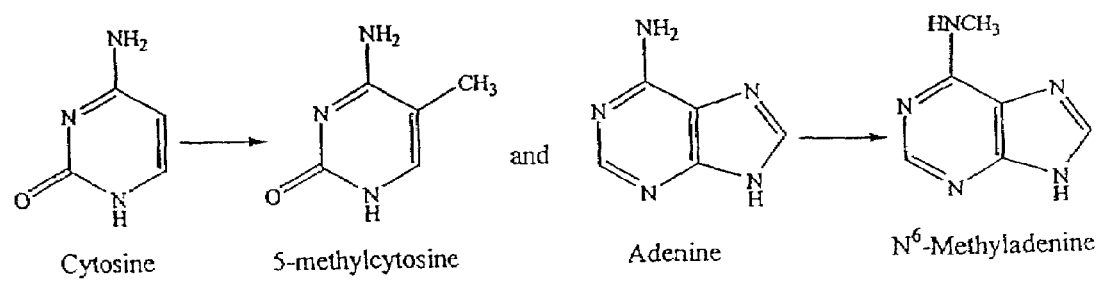
FIG. 2 is a schematic representation of the sites of methylation that occur on cytosine and adenine.
Figure 3:
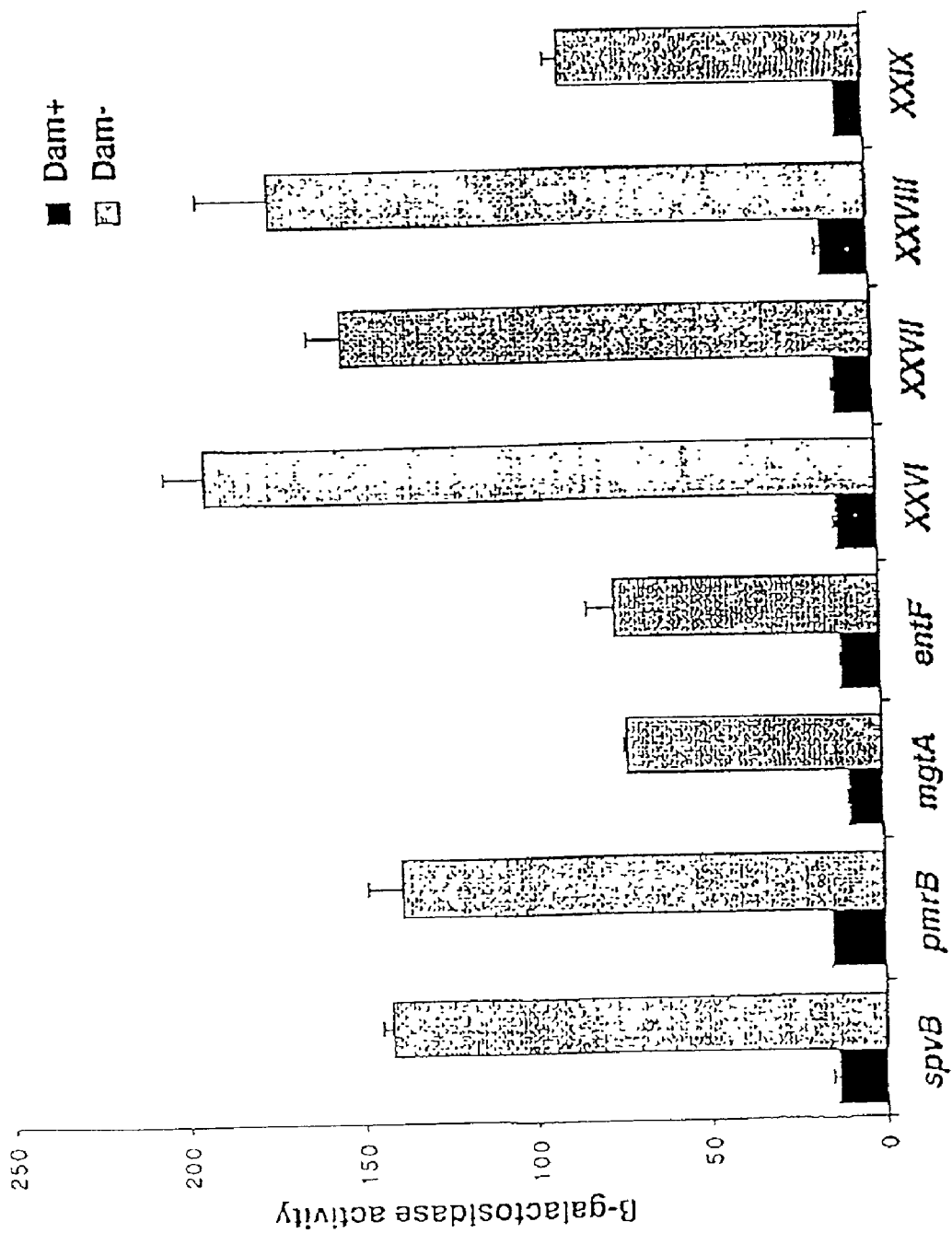
FIG. 3 is a graphic representation illustrating that Dam regulates in vivo induced genes. β-galactosidase expression form S. typhimurium ivi fusions in Dam$^+$ and Dam$^-$ strains grown in LB. The vertical axis shows β-galactosidase activities (μ-moles of o-nitrophenol (ONP) formed per minute per $A_{600}$ unit per milliliter of cell suspension×$10^3$).

DNA adenine methylation has been shown to directly control virulence gene expression in *E. coli* (Braaten, et al., *Cell*, 76:577–588 (1994)). Therefore, it was determined whether Dam regulates *Salmonella* genes that are preferentially expressed in the mouse, designated as in vivo induced (ivi) genes. See, Conner, C. P., et al., *Proc. Natl. Acad. Sci. USA*, 14:4641–4645 (1998); Heithoff, D. M., et al., *Proc. Natl. Acad. Sci. USA.*, 94:934–939 (1997); Mahan, M. J., et al., *Science*, 259:666–668 (1993); Mahan, M. J., et al., *Proc. Natl. Acad. Sci. USA*, 92:669–673 (1995); and U.S. Pat. No. 5,434,065, all of which are incorporated herein by reference. Dam significantly repressed the expression of over 20 ivi genes (2 to 18 fold) when grown in rich medium, eight of which are displayed in FIG. 3. Four of the eight fusions are in known genes, all of which have been shown to be involved, or implicated, in virulence: spvB resides on the *Salmonella* virulence plasmid and functions to facilitate growth at systemic sites of infection (Gulig, et al., *Mol. Microbiol.*, 7:825–830 (1993); pmrB is involved in resistance to antibacterial peptides termed defensins (Roland, et al., *J. Bacteriol.*, 75:4154–4164 (1993); mgtA and entF are involved in the transport of magnesium and iron, respectively (Earhart, *Escherichia coli and Salmonella Cellular and Molecular Biology*, 2nd edition, 1075–1090 (1996); and Vescovi, G., et al., *Cell*, 84:165–174 (1996)). Additional ivi genes of unknown function were also Dam-regulated. These results indicate that Dam is a global regulator of *Salmonella* gene expression.

*Salmonella* pathogenesis is known to be controlled by PhoP, a DNA binding protein that acts as both an inducer and repressor of specific virulence genes (reviewed in Groisman and Heffron *Two-component signal transduction*, 319–332 (1995)). To determine whether the Dam and PhoP regulatory pathways share common genes, the effect of Dam was tested on seven PhoP-activated ivi genes, including spvB, pmrB, and mgtA. FIG. 4 shows that Dam repressed the expression of these three genes by 2 to 19 fold, and this repression was not dependent on the PhoP protein. Dam did not significantly affect the expression of the remaining four PhoP$^-$ activated genes (data not shown). These results indicate that Dam and PhoP constitute an overlapping global regulatory network controlling *Salmonella* virulence.

Binding of regulatory proteins to DNA can form DNA methylation patterns by blocking methylation of specific Dam target sites (GATC sequences (van der Woude, et al., *J. Bacteriol.*, 180:5913–5920 (1998)). Therefore, further investigation of the interactions between Dam and PhoP were carried out by determining if binding of PhoP (or a PhoP-regulated protein) to specific DNA sites blocks methylation of these sites by Dam, resulting in an alteration in the DNA methylation pattern. Analysis of PhoP⁺ and PhoP⁻ Salmonella showed distinct differences in DNA methylation patterns. Digestion of genomic DNA from PhoP⁻ bacteria with MboI (which cleaves only at nonmethylated GATC sites) resulted in the appearance of DNA fragments that were not present in DNA from PhoP⁺ bacteria (FIG. 5, see arrows). These results indicate that the PhoP protein (or a PhoP-regulated gene product) blocks Dam methylation at specific GATC-containing sites in the Salmonella genome. Alternatively, PhoP⁺ and PhoP⁻ strains may have different levels of Dam activity which, in turn, may affect DNA methylation patterns. However, this regulation does not occur at the transcriptional level since Dam does not alter PhoP expression, nor does PhoP alter Dam expression (D. M. Heithoff and M. J. Mahan, unpublished material). Further analysis will determine whether these PhoP-protected sites are within regulatory regions of virulence genes, and if DNA methylation directly affects the PhoP regulon by altering DNA-PhoP interactions.

Example 2A

Protective Efficacy of Dam⁻ Salmonella Attenuated Strains

Strains which demonstrated attenuation as a result of intraperitoneal or oral challenge of BALB/c mice were further tested for protective immunity against subsequent challenge by the wild-type strain at $10^5$ I.P. or $10^9$ orally. BALB/c mice were perorally immunized via gastrointubation with a dose of $10^{+9}$ Dam⁻ S. typhimurium. Five weeks later, the immunized mice were challenged perorally with $10^{+9}$ wild-type S. typhimurium as described. After five weeks, surviving mice were challenged with the wild-type 14028 strain as noted in Table 2 below. Survival for four weeks post challenge was deemed full protection. These data demonstrate the potential use of the present invention in developing vaccine strains.

Since Dam⁻ mutants were highly attenuated, it was determined whether Dam⁻ Salmonella could serve as a live attenuated vaccine. Table 2 shows that all (17/17) mice immunized with a S. typhimurium Dam⁻ insertion strain survived a wild-type challenge of $10^{+4}$ above the $LD_{50}$, whereas all nonimmunized mice (12/12) died following challenge.

TABLE 2

| Immunization with Dam⁻ S. typhimurium | Challenge with $10^{+9}$ wild-type S. typhimurium |
|---|---|
| None | 12/12 dead |
| Dam102::Mud-Cm | 17/17 alive |
| DamΔ232 (nonpolar deletion) | 8/8 alive |

Virtually no visible effects of typhoid fever were observed subsequent to immunization with Dam⁻ Salmonella, nor were there visible effects after the wild type challenge. Moreover, because all (8/8) mice immunized with Salmonella containing the nonpolar Dam deletion (strain ) survived challenge, these data indicate that protection was specifically due to the absence of Dam methylase. The virulence attenuation and effectiveness of Dam⁻ mutants as a vaccine (Tables 1 and 2) could be due to the ectopic expression of virulence determinants (FIGS. 3 and 4) which would likely be deleterious to the growth and/or survival of Salmonella during infection. Thus, ectopic expression provides an explanation as to why the Dam mutant is totally attenuated yet still provides full protection as a live attenuated vaccine.

Colonization Studies

The survival of Dam⁺ and Dam⁻ Salmonella in mouse tissues was compared. As shown in FIG. 6, Dam⁻ bacteria were fully proficient in colonization of a mucosal site (Peyer's patches) but showed severe defects in colonization of deeper tissue sites. Five days after infection, we observed a reduction of three orders of magnitude in numbers of Dam⁻ Salmonella in the mesenteric lymph nodes (relative to numbers of Dam⁺ bacteria) and a reduction of eight orders of magnitude in numbers of Dam⁻ Salmonella in the liver and spleen. These data show that Dam⁻ Salmonella survive in Peyer's patches of the mouse small intestine for at least 5 days, providing an opportunity for elicitation of a host immune response. Dam⁻ Salmonella, however, were unable to cause disease; they either were unable to invade systemic tissues or were able to invade but could not survive.

Example 2B

Protective Efficacy of Killed Dam Derivatives

Determination of whether living Dam⁻ or Dam overproducing bacteria are required to elicit a fully protective response. The ectopic expression of multiple proteins in Dam⁻ vaccines (see above and below) suggests the possibility that killed Dam⁻ organisms may elicit significantly stronger protective immune responses than killed Dam⁺ organisms and thus be used as mucosal vaccine. In vitro grown S. typhimurium Dam⁻ bacteria are killed by exposure to sodium azide (0.02%) and/or UV light, after which the antimicrobial is either washed or dialyzed away from the killed organisms. The efficacy of the whole cell killed vaccine preparation is tested with and without the use of mucosal adjuvants such as cholera toxin, E. coli labile toxin, or vitamin D3 ($1,25(OH)_2D_3$). Accordingly, vaccine preparations containing $10^{10}$ killed Dam⁻ Salmonella, alone and in combination with mucosal adjuvants, are used to orally immunize BALB/c mice (as described in the Examples). As a dosing regimen, mice are immunized by gastrointubation once a week for three weeks. Killed wild-type S. typhimurium serves as a negative control. The immunized mice are orally challenged with virulent S. typhimurium 2 weeks after the last immunization to determine if an effective immune response is generated. If so, mice immunized with the killed vaccine preparation are also challenged with other pathogenic Salmonella serotypes (e.g., enteritidis, choleraesuis, dublin) to determine if the immunity elicited is cross-protective against related strains as is the case for oral administration of Dam⁻ Salmonella live vaccines. If mice immunized with the dead vaccine preparation are protected two weeks after the final immunization (of three), whether the immunity elicited is long-lasting is determined by challenging immunized mice 7 weeks after the last immunization.

Since Dam overproduction may result in the ectopic expression of a new repertoire of potential protective antigens that are not expressed in either the wild-type (Dam⁺) or Dam⁻ vaccine strains, the killed vaccine experiments are performed with Dam overproducing strains, alone and in combination with killed Dam⁻ organisms. Since the two different vaccine strains may produce two different repertoires of potentially protective antigens, use of them in combination may elicit a superior immune response.

Example 3

Cross-protection Elicited by a Dam⁻ and Dam Overproducing Salmonella

Immunization with Dam⁻ and Dam overproducing *Salmonella* elicits a cross-protective response to heterologous serotypes. As shown in FIG. 8 and discussed below, Dam⁻ and Dam overproducing mutants ectopically express multiple genes and proteins that are normally only expressed during infection. Such ectopic expression of multiple antigens may result in cross-protective immune responses against heterologous serotypes. BALB/c mice were immunized with $1 \times 10^9$ Dam⁻ or Dam overproducing *Salmonella* administered orally (via gastrointubation). Mice were challenged with the virulent *Salmonella* serotype eleven weeks post-immunization, which was six weeks after the vaccine strains were cleared from murine tissues, including Peyer's patches, mesenteric lymph nodes, liver, and spleen. *S. typhimurium* strains used in this study were derived from strain ATCC 14028 (CDC 6516-60). Strains used in infection studies were grown overnight in LB at 37° C. with shaking. The Dam::102::Mud-Cm allele was transduced into virulent *S. typhimurium* strain 14028 and *S. enteritidis* 01,9,12; CDC SSU7998, obtained from the Salmonella Genetic Stock Center, SARB, #16 (Boyd, E. F., et al., *J. Gen. Microbiol.*, 139:1125–1132 (1993); Sanderson, K. E., et al., in *Escherichia coli and Salmonella Cellular and Molecular Biology*, F. C. Neidhardt, Ed. (ASM, Washinton DC, ed. 2, 1996), pp. 2496–2503), resulting in Dam⁻ strains, MT2116 (Heithoff, D. M., et al., *Science*, 284:967–970 (1999)), and MT2223, respectively. *S. dublin* Lane was constructed as described (Chikami, G. K., et al., *Infect. Immun.*, 50:420–424 (1985)). The construction of *S. typhimurium* DamΔ232 (MT2188) and Dam102:Mud-Cm (MT2116) was described previously (Heithoff, D. M., et al., *Science*, 284:967–970 (1999)). The Dam overproducing strain in *S. typhimurium* (MT2257) contained *E. coli* Dam on recombinant plasmid pTP166 in a DamΔ232 background (Heithoff, D. M., et al, *Science*, 284:967–970 (1999); Marinus, M. G., et al., *Gene*, 28:123–125 (1984)). The oral $LD_{50}$ of challenge strains were: *S. typhimurium* $10^5$ organisms (Heithoff, D. M., et al., *Science*, 284:967–970 (1999)) and *S. enteritidis* $10^5$ organisms, *S. dublin* $5 \times 10^4$ organisms (Chikami, G. K., et al., *Infect. Immun.*, 50:420–424 (1985)).

The data in Table 3 show the mice were protected against a heterologous challenge eleven weeks post immunization. Immunization with Dam-*S. enteritidis* (Dam102::Mud-Cm, following an experimental protocol described above) confers cross-protection against challenge with $10^9$ *S. typhimurium* and $10^9$ *S. dublin* after five weeks and may confer cross-protection for even longer periods. Table 3A shows that approximately one third of mice vaccinated with a single oral dose of Dam⁻ *S. enteritidis* (Dam102::Mud-Cm) survived a virulent heterologous challenge eleven weeks post-immunization of $10^4$ above the lethal dose required to kill 50% of the animals ($LD_{50}$) against *S. dublin* and *S. typhimurium*, comparable to the level of survival observed upon homologous challenge.

Similarly, mice immunized with Dam⁻ *S. typhimurium* showed significant cross-protection against *S. dublin* and *S. enteritidis* (Table 3B). Importantly, the cross-protective immunity was not attributed to the persistence of the vaccine strain in murine tissues, since mice were protected against heterologous challenge greater than six weeks after the vaccine strain was cleared from immunized animals (i.e., after Dam⁻ organisms could not be detected in Peyer's patches, mesenteric lymph nodes, liver and spleen). The cross-protection elicited is specific to *Salmonella* strainsas no protection was elicited against the systemic pathogen *Yersinia pseudotuberculosis* five weeks post-immunization.

To test whether Dam overproducing strains elicit protective immune responses to homologous and heterologous *Salmonella* serotypes similar to Dam⁻ strains, mice were immunized with Dam overproducing *S. typhimurium*. Seventy-five percent of immunized mice survived a challenge dose of 1000-fold above the $LD_{50}$ of *S. dublin* and *S. typhimurium* (Table 3C). Taken together, these studies indicate that Salmonella strains that under- or over-produce Dam are highly attenuated and serve as protective live vaccines against homologous and at least some heterologous serotypes.

TABLE 3

Oral immunization with Salmonella Dam-based vaccines elicits cross-protective immune responses against heterologous serotypes.

A. Immunization with Dam⁻ *S. enteritidis* confers cross-protective immunity.

| Oral immunization | Oral challenge with $10^9$ wild-type *S. dublin* | Oral challenge with $10^9$ wild-type *S. typhimurium* | Oral challenge with $10^9$ wild-type *S. enteritidis* |
|---|---|---|---|
| No bacteria | 20/20 dead | 19/19 dead | 19/19 dead |
| *S. enteritidis* Dam102::Mud-Cm | 9/26 alive | 7/25 alive | 5/26 alive |

B. Immunization with Dam⁻ *S. typhimurium* confers cross-protective immunity.

| Oral immunization | Oral challenge with $10^8$ wild-type *S. enteritidis* | Oral challenge with $10^9$ wild-type *S. dublin* | Oral challenge with $10^8$ wild-type *S. dublin* | Oral challenge with $10^9$ Wild-type *S. typhimurium* |
|---|---|---|---|---|
| No bacteria | 17/17 dead | 25/25 dead | 11/11 dead | 10/10 dead |
| *S. typhimurium* DamΔ232 | 4/18 alive | 4/19 alive | 10/19 alive | 11/11 alive |

C. Immunization with *S. typhimurium* Dam overproducing strain confers cross-protective immunity.

| Oral immunization | Oral challenge with $10^8$ wild-type *S. dublin* | Oral challenge with $10^8$ wild-type *S. typhimurium* |
|---|---|---|
| No bacteria | 10/10 dead | 10/10 dead |
| *S. typhimurium* (pTP166) (Dam overproducer) | 6/8 alive | 6/8 alive |

Dam⁻ and Dam overproducing derivatives ectopically express multiple proteins in vitro. Ectopic expression of multiple proteins in Dam⁻ strains may contribute to the cross-protection elicited against heterologous serotypes that share common epitopes. To this end, we have shown that Dam-strains ectopically express of a number of Salmonella genes that are normally repressed in vitro.

Two-dimensional protein gel electrophoresis was performed by the method of O'Farrell ((1975) *J. Biol. Chem.* 250: 4007–4021) on whole-cell protein extracts of log-phase *S. typhimurium* grown in Luria broth. Isoelectric focusing using pH 5–7 ampholines (BioRad Laboratories, Hercules, Calif.) was carried out at 800 V for 17 h. The second dimension consisted of 12.5% polyacrylamide slab gels which were run for 5.5 h at 175 V. Proteins were visualized by silver staining (Merril et al. (1984) *Methods Enzymol.* 104:441–447.). The results are shown in FIG. 8. The results show that two-dimensional gel electrophoresis analysis (2-D protein analysis) of Dam⁻, Dam⁺ (wild type) and Dam overproducer (OP) strains grown in vitro resulted in the detection of several proteins (FIG. 8, see arrows) that were expressed under the Dam⁻ condition that were not detected under either the Dam⁺ (wild type) or Dam OP (expressing about 100-fold higher Dam than normal) conditions. These data indicate that Dam⁻ *Salmonella* ectopically express multiple proteins in vitro (and presumably in vivo), suggesting that dysregulation of protein expression could provide multiple novel protein targets to be processed and presented to the immune system.

Further analysis of protein expression was carried out using immune sera from mice vaccinated with Dam⁻ *Salmonella* to probe the two-dimensional gels. Proteins from whole-cell protein extracts of *S. typhimurium* Dam⁻ and Dam⁺ strains were separated by two-dimensional electrophoresis, transferred to a PVDF membrane (Pierce, Rockford, Ill.), and probed with pooled antisera obtained from BALB/c mice immunized with Dam⁻ *S. typhimurium*. Peroxidase-conjugated sheep anti-mouse IgG (Amersham Life Sciences, Arlington Heights, Ill.) was used as secondary antibody. Blots were detected using Supersignal West Femto Maximum Sensitivity Substrate (Pierce, Rockford, Ill.). We identified specific proteins expressed by in-vitro grown Dam⁻ but not Dam⁺ *Salmonella* that elicited a humoral response in mice. This class of antigens may contribute to the protective immunity elicited by Dam⁻ vaccine strains.

2-D protein analysis indicates that Dam overproducing strains of *Salmonella* (*S. typhimurium* ATCC 14028 with plasmid pTP166 that overproduces *E. coli* Dam at about 100-fold the wildtype level) express a number of gene products that are not expressed by Dam⁺ (wild type) or Dam⁻ *Salmonella* under laboratory growth conditions. In addition, at least one protein was preferentially expressed in wild-type *Salmonella* compared to the two Dam mutant strains (FIG. 8B, see arrow). This latter expression pattern is similar to that of the Dam-regulated uropathogenic *E. coli* pyelonephritis associated pili (pap) operon, in which under- and over-expression of Dam blocks Pap pili production (Blyn, L. B., et al., *EMBO J*, 9:4045–4054 (1990)). Taken together with our observation that Dam overproducing strains are attenuated and elicit protective immunity, these results suggest that Dam overproduction may result in the expression of a different repertoire of antigens than what is produced in Dam⁻ strains. Thus, vaccines consisting of Dam overproducing strains in combination with the Dam⁻ strains may be highly cross-protective due to the ectopic expression of two different repertoires of potentially protective antigens.

Immunity elicited by Dam⁻ strains is greater than immunity elicited after a wild-type infection. One of the most effective virulence properties of a pathogen is the ability to evade host immune responses. Such a "stealth" strategy is achieved by tightly regulating many of its functions to avoid host immune recognition. Thus, as a bacterial protective mechanism, it is likely that many antigens produced by virulent organisms are not produced in sufficient quantities and/or for a sufficient amount of time to elicit a host immune response. However, Dam⁻ bacteria may ectopically express multiple antigens that are processed and presented to the immune system, and thus, animals immunized with Dam⁻ vaccines may elicit stronger immune responses than animals that survive a natural infection.

The immunity elicited by the Dam⁻ vaccine was compared to the immunity elicited after a natural infection with the wild-type strain. BALB/c mice were orally immunized at the $LD_{50}$ of the virulent strain *S. typhimurium* ($10^{+5}$ organisms) (i.e., one half the mice survived the wild-type immunization) or $10^{+5}$ Dam⁻ organisms. Five weeks post-immunization, the immunized mice were challenged with lethal doses of the virulent strain. Table 5 shows that the immunity elicited by the Dam⁻ vaccine was at least 100-fold greater (3 of 10 mice survived a $10^{+9}$ challenge) than the immunity elicited in mice that survived an immunization with the wild-type strain (1 of 10 survived a $10^{+7}$ challenge).

TABLE 4

Mice immunized with Dam⁻ vaccines elicit greater protection than mice that survive a wild-type infection.

| Oral immunization $10+^5$ *S. typhimurium* | Oral challenge with $10^7$ wild-type *S. typhimurium* | Oral challenge with $10^8$ wild-type *S. typhimurium* | Oral challenge with $10^9$ *S. typhimurium* |
|---|---|---|---|
| None | 10/10 dead | 10/10 dead | 10/10 dead |
| Dam⁺(at $LD_{50}$) | 1/10 alive | 10/10 dead | 10/10 dead |
| DamΔ232 | 5/10 alive | 4/10 alive | 3/10 alive |

Additionally, immunization with Dam organisms showed relatively similar levels of protection over a wide range of challenge doses ($10^{+7}$ to $10^{+9}$). This suggests that an immunizing dose of $10^{+5}$ Dam⁻ bacteria is below the minimum threshold of organisms required to ensure a productive immune response in all immunized animals. It is possible that the enhanced immunity elicited by Dam⁻ strains may be attributed, in part, to the ectopic expression of Dam repressed-antigens, which may not be produced in sufficient quantities and/or duration during a wild-type infection.

Figure 7:
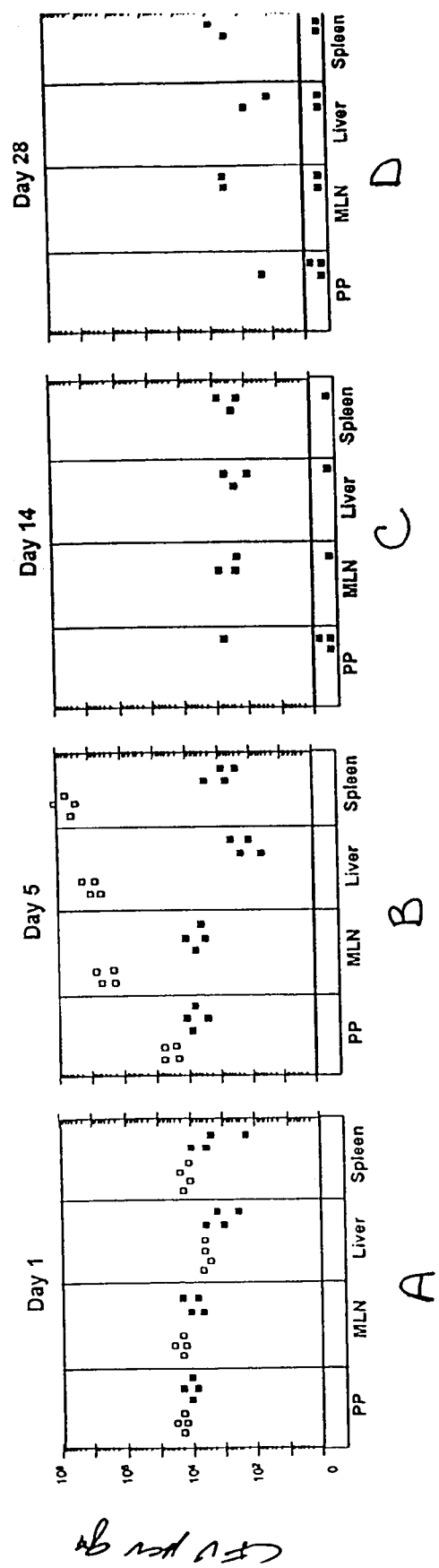

Immunized animals hinder growth of virulent bacteria in systemic tissues. Dam⁻ *Salmonella* were found to be fully proficient in colonization of Peyer's patches of the mouse small intestine but were severely deficient in colonization of deeper tissue sites (liver and spleen) (Example 1). Dam⁻ mutants of *S. typhimurium* are also less cytotoxic to M cells, are deficient in epithelial invasion, and display defects in protein secretion. Pucciarelli et al. (1999) *Proc. Natl. Acad. Sci. USA* 96:11578–11583. Taken together, these data provide a possible explanation as to why Dam⁻ mutants are unable to cause disease but are able to elicit a full-protective immune response. Since mice immunized with Dam⁻ *Salmonella* showed virtually no overt symptoms of disease after challenge with virulent organisms, the fate of wild-type Salmonella was compared within immunized vs. non-immunized mice. Following a challenge dose of 10,000-fold above the $LD_{50}$, nonvaccinated mice showed a rapid increase in bacterial number in the Peyer's patches, mesenteric lymph nodes, liver, and spleen, succumbing to the infection on Day 5 (FIG. 7). The data in FIG. 7 show that Dam⁻ immunized mice carry high loads ($10^4$) of virulent bacteria for at least five days in both mucosal and systemic tissues after wild-type challenge of $10^9$ organisms. However, the immunized mice have the ability not only to inhibit the growth of these virulent organisms, they are capable of clearing them from both mucosal and systemic tissues (2 out of 4 mice have cleared all virulent organisms from the Peyer's patches, mesenteric lymph nodes, liver and spleen 28 days post challenge). This ability to clear $10^4$ virulent organisms from the liver and spleen is significant in light of the fact that the i.p. $LD_{50}$ is less than 10 organisms. Thus, immunization with Dam⁻ *Salmonella* hinders the proliferation of wild-type organisms in all tissues tested. The ability to clear a lethal load of virulent bacterium from systemic suggests the possibility that Dam⁻ vaccines may have therapeutic application to the treatment of a pre-existing microbial infections.

Example 4

Vaccination of Chicken Against *S. enteritidis*

A thorough understanding of the dynamics of *S. enteritidis* infection in poultry is essential to the formulation of an effective strategy to interrupt the eggborne transmission of *S. enteritidis* from laying hens to human consumers. *Salmonellae* cause disease by colonizing and invading the intestinal epithelium. In some cases, *Salmonella* penetration through the intestinal mucosa to the bloodstream is followed by widespread dissemination and systemic disease. *S. enteritidis* is an invasive serotype in chicks but has not exhibited a level of pathogenicity for chicks that is markedly different from that of other paratyphoid *Salmonella* serotypes. Popiel and Turnbull (1985) *Infect. Immun.* 47(3):786–792. Chicks can be readily infected, involving both intestinal colonization and invasion to reach internal issues such as the liver, with *S. enteritidis* from contaminated feed. Hinton et al. (1989) *Vet. Rec.* 124:223.

Experimental infections of adult hens with some *S. enteritidis* strains have led to intestinal colonization that persisted for several months, although in studies with other *S. enteritidis* strains the duration of fecal shedding has been considerably shorter. (Gast and Beard, 1990), Gast and Beard (1990) *Avian Dis.* 34:991–993; Shivaprasad et al. (1990) *Avian Dis.* 34:548–557. In one study, intravenously infected birds shed *S. enteritidis* for a longer period than did orally infected birds. Shivaprasad et al. (1990).

The effectiveness of various methods of destroying *S. enteritidis* in eggs and egg products has become a topic of increasing importance to public health authorities and the egg industry. Such information is vitally needed in order to provide instructions to consumers and commercial or institutional users of eggs regarding safe preparation of egg-containing foods. Shivaprasad et al. (1990) observed that the time/temperature requirements for destroying *S. enteritidis* in eggs by various cooking methods did not differ significantly from similar requirements previously determined for *S. typhimurium*. Baker et al. (1983) *Poult. Sci.* 72:1211–1216. Humphrey et al. found that strains of phage type 4 *S. enteritidis, S. typhimurium*, and *S. senftenberg*, when inoculated into egg yolk, could survive forms of cooking in which some of the yolk remained liquid. Humphrey et al. (1989) *epidemiol. Infect.* 103:35–45. Moreover, when eggs were stored at room temperature for 2 days after inoculation, the *S. enteritidis* population grew to such a high level in the yolk that no standard cooking method completely eliminated the *Salmonella*. Storage of *S. enteritidis* cultures at refrigerator temperatures, on the other hand, has been found to increase their sensitivity to heat. Humphrey (1990) *J. Appl. Bacteriol.* 69:493–497. In another study, *S. enteritidis* phage type 4 in homogenized whole egg was determined to be more heat resistant than phage types 8 or 13a and *S. typhimurium*, but less than the highly heat-resistant *S. senftenberg* strain 775W. All *Salmonella* strains tested were more heat resistant in yolk than in whole egg or albumin. Humphrey et al. (1990) *Epidemiol. Infect.* 104: 237–241.

The vaccines of the present invention, specifically Strain 3, may be effective at eliminating *S. enteritidis* in eggs and egg products. A Dam⁻ *S. typhimurium* vaccine is prepared as described previously. The vaccine is introduced into the chicken by way of oral administration, that is, mixed with the chickens feed and/or water. Once the vaccine has been administered the virulence factors typically repressed by Dam will be expressed and the chicken will elicit an immune response. Since some of these Dam-regulated genes are homologs to those shared by *S. enteritidis*, the Dam⁻ *S. typhimurium* may elicit cross-protection against *S. enteritidis*, as the data in Example 3 indicate.

The above description also applies to immunization of chickens against *Salmonella* (including eliciting cross-protection).

Example 5

Administration of Dam Derivative Salmonella Vaccines to Cattle

*Salmonella* is the most commonly isolated infectious enteric bacterial pathogen of dairy cattle and the most common zoonotic disease associated with human consumption of beef and dairy products. In recent years there has been a rise in the incidence and severity of human cases of salmonellosis, in part due to the emergence of the antimicrobial resistant *S. typhimurium* DT104 in cattle populations. Prevalence studies indicate 16 to 73% of U.S. dairy farms are infected with *Salmonella* and up to 50% of cull dairy cows are contaminated with *Salmonella* at slaughter. On-farm *Salmonella* control is important to reduce production losses and human food borne disease.

On large commercial dairy farms it is very common for cattle to be exposed to multiple *Salmonella* serotypes and for calves to become infected shortly after birth. Under these conditions it would be very desirable to have a *Salmonella* vaccine capable of stimulating immunity to heterologous *Salmonella* serotypes.

A. Requirement of Dam for *Salmonella* infection of cattle, and effectiveness of Dam⁻ derivatives as live bovine vaccines Holstein bull calves 1–3 days of age would be used for all of the experiments. Measurement of total plasma protein is used to assess passive immunity of calves. Only calves with a total plasma protein greater than or equal to 5.5 are used. The Salmonella infection status of the source dairies is determined prior to purchasing the calves by culturing fecal and environmental samples for salmonellae. The *Salmonella* negative status of calves will be confirmed after purchase by daily fecal *Salmonella* cultures.

The calves are housed and raised in Animal Biosafety 2 level facilities. Calves are fed 2 quarts of 20:20 milk replaced twice a day and have access to fresh calf grain and fresh water 24 hours a day. Each day at feeding time all calves are given an appetite and attitude score. The appetite score is on a scale of 1 to 4 (1=consumed 2 quarts of milk, 2=consumed<2 but>1 quart of milk, 3=consumed<1 quart of milk, and 4=consumed no milk). The attitude score is also on a scale of 1–4 (1=standing, 2=stands with encouragement, 3=stands with assistance, 4=unable to stand). Following all of the challenge experiments calves are checked 3 times a day and vital parameters recorded twice a day. Any calf that is unable to stand is considered terminal and is euthanized. No antimicrobial or anti-inflammatory treatments are administered to calves following *Salmonella* challenge to avoid confounding of the experimental results.

Determination of the safety of live Dam⁻ *Salmonella* vaccines in Holstein bull calves. The safety of Dam⁻ *S. typhimurium* in 1–3 day old calves is determined as follows.

Eighteen 1–3 day old calves are divided into 3 groups of 6. The first group of 6 calves is challenged orally with $10^9$ Dam⁻ *Salmonella*, the second group with $10^{10}$ and the third with $10^{11}$. For the 3 weeks following challenge each calf in the study is evaluated twice a day to measure pulse and respiratory rate, rectal temperature, appetite, and attitude. Fecal samples are collected from each calf daily for *Salmonella* culture. At 3 weeks post challenge the calves are euthanized and organs (liver, bile, spleen, mesenteric lymph nodes, ileum mucosa, small intestinal contents, cecum mucosa and cecal contents) cultured for salmonellae.

Determination of whether *Salmonella* Dam based vaccines can colonize mucosal and/or systemic tissues. The kinetics of colonization of bovine tissues is determined for both Dam⁺ and Dam⁻ *S. typhimurium* after oral administration. The "bacterial load" in the small intestinal contents, ileum mucosa, Peyer's patches, cecum mucosa, cecal contents, mesenteric lymph nodes, liver, and spleen, is determined in calves, as a function of time post infection. Twenty four holstein bull calves are challenged orally with $10^9$ Dam⁻ *S. typhimurium*. Six calves are randomly assigned to 4 groups to be euthanized at 24 hours and 5, 14, and 28 days post challenge. Tissues are collected from each calf at necropsy for quantitative *Salmonella* culture. Twenty four holstein bull calves challenged orally with $10^9$ Dam⁺ *S. typhimurium* are processed identically and serve as a positive control for these experiments.

For Dam⁻ *Salmonella* to be ideal bovine vaccines, they should colonize the Peyer's patches, replicate and persist within the M cells, and present antigens to the underlying immune cells (e.g., macrophages, B cells and T cells) that comprise the Peyer's patch lymphoid follicle. As importantly, they should not colonize deeper tissue such as the liver and spleen, and should eventually be cleared from the Peyer's patches. If these criteria are met, it is more likely that *Salmonella* Dam⁻ mutants would serve as the basis for a safe, effective bovine vaccine.

Protective efficacy of Dam⁻ *S. typhimurium* vaccination against homologous wild-type challenge. Twenty calves 1–3 days of age are randomly divided into 2 groups of 10 calves. The first group is vaccinated per os with Dam⁻ *S. typhimurium* at 1–3 days of age. The remaining 10 unvaccinated calves \serve as controls. All calves are challenged per os with $10^{11}$ virulent *S. typhimurium* at 5 weeks of age. For the 3 weeks following challenge each calf is evaluated three times a day and pulse, respiratory rate, rectal temperature, appetite score, and attitude score recorded twice a day. Fecal samples are collected from each calf daily for *Salmonella* culture. All calves that die following challenge are necropsied and organs (liver, bile, spleen, mesenteric lymph nodes, ileum mucosa, small intestinal contents, cecum mucosa and cecal contents) cultured for salmonellae. Calves surviving virulent *Salmonella* challenge are euthanized 3 weeks post challenge, necropsied, and organs cultured for salmonellae (liver, bile, spleen, mesenteric lymph nodes, ileum mucosa, small intestinal contents, cecum mucosa and cecal contents).

Minimum dose regimen required for efficacy in calves and reduced vaccine persistence in bovine tissues. Three important features of any vaccine regimen are i) the dose of the vaccine, ii) the age of the animal, iii) and the persistence of the vaccine in the immunized animal. Minimum dose required to elicit full protection (at 10,000 times the $LD_{50}$) and reduced persistence in murine tissues such as the Peyer's patches, mesenteric lymph nodes, liver, and spleen is determined.

B. Dam⁻ Derivatives Elicit Cross-protection Against Related (Heterologous *Salmonella* Serotypes) Pathogenic Strains Protective efficacy of Dam⁻ *S. typhimurium* vaccination against heterologous wild-type challenge. Three similar virulent *Salmonella* challenge experiments are performed using 3 different challenge organisms. Each experiment involves oral immunization of calves with Dam⁻ *S. typhimurium* at 1–3 days of age and challenge with virulent *Salmonella* at 5 weeks of age. In the first experiment *S. Montevideo* (serogroup C1) is used as the challenge organism, *S. dublin* (serogroup D) in the second, *S. anatum* (Serogroup E1) in the last. Different calves are used for each experiment. For each of these 3 experiments twenty calves 1–3 days of age are randomly divided into 2 groups of 10 calves. The first group is vaccinated per os with Dam⁻ *S. typhimurium* at 1–3 days of age. The remaining 10 unvaccinated calves serve as controls. All calves are challenged per os with $10^{11}$ virulent *Salmonella* at 5 weeks of age.

For the 3 weeks following challenge each calf is evaluated three times a day and pulse, respiratory rate, rectal temperature, appetite score, and attitude score recorded twice a day. Fecal samples are collected from each calf daily for *Salmonella* culture. All calves that die following challenge are necropsied and organs (liver, bile, spleen, mesenteric lymph nodes, ileum mucosa, small intestinal contents, cecum mucosa and cecal contents) cultured for salmonellae. Calves surviving virulent *Salmonella* challenge are euthanized 3 weeks post challenge, necropsied, and organs (liver, bile, spleen, mesenteric lymph nodes, ileum mucosa, small intestinal contents, cecum mucosa and cecal contents) cultured for salmonellae. Comparison of cross-protective immunity elicited in Dam overproducing strains, alone and in combination with Dam⁻ mutants, is also performed.

C. Killed Dam⁻ Derivatives of *Salmonella*

In vitro grown *S. typhimurium* Dam⁻ bacteria are killed by exposure to sodium azide (0.02%) and/or UV light, after which the antimicrobial is either washed or dialyzed away from the killed organisms. The efficacy of the whole cell killed vaccine is tested administered per os (oral) and parenterally. For the parenteral vaccine group $10^6$ killed Dam⁻ *Salmonella* is mixed with aluminum hydroxide and quill A adjuvants and administered to calves via intramuscular injection. For the per os vaccination group $10^{10}$ killed Dam⁻ *Salmonella* is administered per os with Vitamin D3 as a mucosal adjuvant. As a dosing regimen, neonatal calves are immunized once a week for three weeks. Killed wild-type *S. typhimurium* administered by the same route and with the same adjuvants serve as a negative control. The immunized calves are challenged with virulent *S. typhimurium* 2 weeks after the last immunization using the same protocol as described above to determine if an effective immune response is generated. If so, calves immunized with the killed vaccine preparation are also be challenged with other pathogenic *Salmonella* serotypes (e.g. *montevideo, S. dublin,* and *S. anatum*) to determine if the immunity elicited is cross-protective against related strains. The experiment is repeated using Dam overproducing strains, alone or in combination with killed Dam⁻ organisms.

Since Dam overproduction may result in the ectopic expression of a new repertoire of potential protective antigens that are not expressed in either the wild-type (Dam⁺) or Dam⁻ vaccine strains the killed vaccine experiments are repeated with Dam overproducing strains, alone and in combination with killed Dam⁻ organisms.

Construction of Dam⁻ Mutants in *Vibrio cholerae*

A. Construction of *V. cholerae* Dam mutations

*V. cholerae* Dam mutations are not currently available. Known *V. cholerae* Dam sequence is used to design primers to PCR amplify the Dam gene, which is used as a probe to hybridize against an *V. cholerae* lambda clone bank to recover the wild-type *V. cholerae* Dam clone. The DNA ends of hybridizing clones are sequenced to determine whether they contain the *V. cholerae* Dam region. Subcloning and further sequencing off the vector ends of these subclones identifies the smallest DNA restriction fragment containing the entire *V. cholerae* Dam sequence. Non-revertible Dam deletion mutations associated with an antibiotic resistance marker are constructed according to methods recently developed (Julio, S. M., et al., *Molec. Gen. Genet.*, 258:178–181 (1998).

The role(s) of Dam mutants in *V. cholerae* pathogenesis are tested in two different virulence assays for murine cholera (suckling mouse models), the $LD_{50}$ and the competitive index, which have been described in Example 1.

B. Determination of the Protective Capacity of Dam Mutants Toward the Goal of Constructing Human Live Attenuated Vaccines Against *V. cholerae*

As discussed in detail above, *Salmonella* Dam⁻ mutants serve as live attenuated vaccines in a mouse model for typhoid fever. The goal of this experiment is to discern whether these desired effects are specific to *Salmonella* DNA adenine methylation or whether Dam mutants also afford protection against *V. cholerae*, and thus may provide a foundation for a new generation of live attenuated vaccines.

Human live attenuated vaccines must be designed to limit the risk of reversion to wild type and to ensure that these strains will not serve as a reservoir for the spread of antibiotic resistance to emerging pathogens. Thus, the next step in this analysis will be to construct an appropriate non-reverting, antibiotic sensitive derivative. Non-polar deletions (no effect on downstream genes in the operon) in Dam are constructed by removing internal sequences of these genes by standard PCR-based approaches, ligation into a suicide vector, and recovery of the resultant in-frame deletion strains. Deletions of each gene are introduced individually using standard positive-selection suicide vector strategies (Donnenberg, M. S., et al., *Infect Immun.*, 59:4310–4317 (1991)), resulting in the desired non-reverting, attenuated, antibiotic sensitive vaccine strain. The efficacy of this vaccine is retested as described above. Strains constructed such that Dam is modified (i.e., not completely deleted and/or disabled) are tested, as are Dam overproducing strains.

Example 7

Essentiality of Dam Gene in *Vibrio cholerae* and *Yersinia pseudotuberculosis*

Merodiploid analysis has revealed that, in contrast to *E. coli* and *Salmonella* spp., Dam was essential for viability in *V. cholerae* and *Y. pseudotuberculosis*. A duplication of Dam was constructed by integrating a recombinant plasmid containing a Dam mutation into the wild type Dam locus. The resulting duplication contained two copies of Dam: a mutant copy and a wild type copy. Normally, the recombinant plasmid segregates at a given frequency, and there is a roughly equal chance that the recombinants (segregants) contain either the mutant or the wildtype gene. If a gene is essential, all segregants of the duplication (which recombines out of the plasmid) are wild type; the recombinants having the mutant gene die. If a recombinant plasmid containing the gene is present, the duplication can segregate either to the mutant or wild type. For *Vibrio cholerae* and *Yersinia pseudotuberculosis*, duplication of the Dam gene to contain both a wild type and a mutant cannot segregate to the mutant unless a recombinant plasmid providing a wild type Dam gene is present.

Dam⁻ segregants of *Y. pseudotuberculosis* and *V. cholerae* were only obtained in the presence of a wild-type copy of Dam provided in trans, indicating that Dam is essential for viability in both organisms. The *Y. pseudotuberculosis* and *V. cholerae* Dam genes were identified by complementation of 2-amino purine sensitivity of *S. typhimurium* Dam mutants. These complementing plasmid clones were introduced into Dam⁻ *E. coli*. Recovered plasmids were found to be resistant to the methylation-sensitive restriction enzyme, MboI, indicating that the complementing clones encode the Dam methylase. The *Y. pseudotuberculosis* and *V. cholerae* Dam genes identified encode putative proteins that are 70% and 63% identical over the entire *E. coli* Dam protein, respectively, using the Fasta sequence comparison program of Genetics Computer Group (GCG). Note the *V. cholerae* Dam gene described in these studies differs from a previously published putative Dam sequence, which has 60% identity at the nucleotide level over 250 bp of the 837 bp *E. coli* Dam gene (Bandyopadhyay, R., et al., *Gene*, 140:67–71 (1994)). The Dam nucleotide sequences in this study have been deposited in GenBank: accession numbers for *Y. pseudotuberculosis* (AF274318) and *V. cholerae* (AF274317).

Example 8

Dam Overproducing *Yersinia pseudotuberculosis* and *Vibrio cholerae* are Avirulent Bacterial strains were derivatives of *Y. pseudotuberculosis* strain, YPIIIpYV, and *V. cholerae* strain O395. Dam overproducing strains of *Y. pseudotuberculosis* (MT2294) and *V. cholerae* (MT2284) contained *E. coli* Dam on chloramphenicol and tetracycline resistant derivatives of recombinant plasmids, pTP166 (Marinus, M. G., et al., *Gene*, 28:123–125 (1984)) and pWKS30 (Wang, R., et al., *Gene*, 100:195–199 (1991)) respectively, in Dam⁻ (ΔDam::Km) genetic backgrounds (Julio, S. M., et al., *Molec. Gen. Genet.*, 258:178–181 (1998)). Since Dam is essential for viability in *Y. pseudotuberculosis* and *V. cholerae*, loss of the Dam overproducing plasmids in Dam⁻ backgrounds is lethal for both pathogens.

Virulent properties of the Dam overproducing *Y. pseudotuberculosis* and *V. cholerae* were tested by oral inoculations of BALB/c mice. The results are presented in Table 5. The Oral $LD_{50}$ Ratio (the $LD_{50}$ of the Dam Overproducer divided by the $LD_{50}$ of wild-type bacteria) was determined by infecting twenty BALB/c mice with $7.6 \times 10^9$ of *Y. pseudotuberculosis* Dam overproducing strain (MT2294) as described (Heithoff, D. M., et al., *Science*, 284:967–970 (1999)). Eighteen of 20 mice survived this challenge dose. The peroral $LD_{50}$ of wild-type *Y. pseudotuberculosis* ($2.5 \times 10^7$) was determined by Monack et al. (Monack, D. M., et al., *J. Exp. Med.* 188:2127–2137 (1998)). ND represents not determined.

The competitive index is the ratio of mutant to wild-type bacteria recovered and essentially reflects how fit the mutant strain is compared to the wild-type strain. For *Y. pseudotuberculosis* infection, six BALB/c mice were gastrointubated with a one-to-one ratio of mutant to wild type as described (Conner, C. P., et al., *Proc. Natl. Acad. Sci. USA*, 14:4641–4645 (1998)). Five days post infection, the bacterial cells were recovered from the spleen. For *V. cholerae* infection, six CD1 mice were gastrointubated with a one-to-one ratio of mutant to wild type; 24 hrs post-infection, mice were sacrificed and bacterial numbers were isolated from the intestine as described (Correa, N. E., et al., *Mol. Microbiol.*, 35:743–755 (2000)).

Dam overproduction attenuated the virulence of *Y. pseudotuberculosis* by over 300-fold in a murine bacteremia infection model and attenuated *V. cholerae* colonization 5-fold in a suckling mouse model (Table 5). The attenuation in both organisms was not due to a general growth defect since the Dam overproducing strains showed similar growth rates in vitro compared to wild type. Relevant to these findings, Dam overproduction was recently shown to attenuate the intracellular replication of *Brucella abortus* in murine macrophages (Robertson, G. T., et al., *J. Bacteriol.*, 182:3482–3489 (2000)).

TABLE 5

Dam overproduction confers a virulence defect in *Y. pseudotuberculosis* and *V. cholerae*.

| Relevant genotype | Oral $LD_{50}$ Ratio (mutant/wild type) | Competitive Index |
|---|---|---|
| Dam Overproducer *Y. pseudotuberculosis* | >300 | <$10^{-4}$ |
| Dam Overproducer *V. cholerae* | ND | 0.218 |

Example 9

Protective Efficacy of Dam Overproducing *Yersinia pseudotuberculosis*

Because Dam overproducer mutant was attenuated for virulence in *Y. pseudotuberculosis*, we determined whether a Dam overproducing strain of *Y. pseudotuberculosis* could serve as a live attenuated vaccine against murine bacteremia. BALB/c mice were perorally immunized via gastrointubation with a dose of $7.6 \times 10^9$ cells of *Y. pseudotuberculosis* Dam overproducing strain, MT2294, as described in Example 8. Eight weeks later, the immunized mice were challenged perorally with $3.2 \times 10^9$ wild-type *Y. psuedotuberculosis*. The results are shown in Table 6. All mice (9/9) immunized with a Dam overproducing strain of *Y. pseudotuberculosis* survived a wild-type challenge of greater than 125-fold above the $LD_{50}$ (Table 6), showing no visible effects of infection, whereas all (10/10) nonimmunized mice died after challenge.

TABLE 6

Dam overproducing isolates of *Y. pseudotuberculosis* serve as effective live attenuated vaccines.

| Immunization | Challenge with wild-type *Y. pseudotuberculosis* |
|---|---|
| None | 10/10 dead |
| *Y. pseudotuberculosis* Dam overproducer | 9/9 alive |

Moreover, wild-type *Yersinia* colonized Peyer's patches in immunized mice but were prevented from colonizing systemic tissue sites. Virulent *Y. pseudotuberculosis* ($3.2 \times 10^9$ cells) were perorally administered to nonvaccinated mice (open boxes) or to mice perorally vaccinated (closed boxes) with *Y. pseudotuberculosis* Dam overproducing strain ($7.6 \times 10^9$ cells). Vaccinated mice were challenged eight weeks post-immunization. Five days post-challenge, mice were sacrificed and bacteria were recovered from the host tissues indicated. Five days post-infection, we observed a 100-fold reduction in numbers of $Dam^+$ bacteria in mesenteric lymph nodes and a 10,000-fold reduction in numbers of $Dam^+$ bacteria in the spleen in vaccinated mice (FIG. 9). Taken together, these data indicate that immunization of mice with a Dam overproducing *Y. pseudotuberculosis* strain elicited high levels of protection against *Yersinia* infection.

The foregoing description is considered as illustrative only of the principles of the invention. Furthermore, since numerous modifications and changes will readily occur to those skilled in the art, it is not desired to limit the invention to the exact construction and processes shown as described above. Accordingly, all suitable modifications and equivalents may be restored to falling within the scope of the invention as defined by the claims which follow.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A method of preparing a composition having reduced bacterial virulence of a pathogenic bacteria, comprising:
   growing in culture medium a virulent bacteria having a DNA methyltransferase (Dam) activity;
   contacting the bacteria with an agent that prevents the bacteria's dam gene expression thereby altering the bacteria's native level of methylation of adenine in a GATC tetranucleotide of the bacteria, and thereby reducing virulence of the bacteria; and
   separating the bacteria from said culture medium and adding to the separated bacteria a pharmaceutically acceptable excipient, wherein the bacteria are selected from the group consisting of:
   Bordetella,
   Haemophilus.
   Neisseria,
   Pasteurella,
   Shigella,
   Treponema, and
   Yersinia.

2. The method of claim 1, wherein the agent causes a deletion within the bacteria's dam gene.

3. The method of claim 1, wherein the agent causes an insertion within the dam gene.

4. The method of claim 1, wherein the agent binds a native dam nucleic acid sequence of the bacteria and prevents expression of a Dam gene.

5. The method of claim 1, wherein the agent alters Dam activity of a pathogenic bacteria selected from the group consisting of Neisseria meningitidis, Pasteurella multocida, and Shigella spp.

6. The method of claim 1, wherein the bacteria are Y. pseudotuberculosis.

7. The method of claim 1, wherein the agent alters native Dam activity of a pathogenic bacteria selected from the group consisting of Shigella, Haemophilus, Bordetella, Neisseria, Pasteurella and Treponema.

8. The method of claim 1, wherein the bacteria are Haemophilus.

9. A composition comprising a pharmaceutically acceptable excipient together with an attenuated, pathogenic bacteria having reduced bacterial virulence, wherein the bacteria is altered by an agent that prevents the bacteria's dam gene expression thereby altering the bacteria's native level of methylation of adenine in a GATC tetranucleotide of the bacteria,
   wherein the alteration is selected from the group consisting of: a deletion within a dam gene of the bacteria, an insertion within a dam gene of the bacteria, and an agent bound to a native dam nucleic acid sequence of the bacteria and preventing expression of a dam gene, and
   the bacteria is selected from the group consisting of: Bordetella, Haemophilus, Neisseria, Pasteurella, Shigella, Treponema, and Yersinia.

10. The composition of claim 9 wherein the alteration is a deletion within a dam gene of the bacteria.

11. The composition of claim 9 wherein the alteration is an insertion within a dam gene of the bacteria.

12. The composition of claim 9 wherein the alteration is an agent bound to a native dam nucleic acid sequence of the bacteria and preventing expression of a dam gene.

* * * * *

SEQUENCE LISTING

<160> NUMBER OF SEQ ID NOS: 4

<210> SEQ ID NO 1
<211> LENGTH: 28
<212> TYPE: DNA
<213> ORGANISM: Artificial Sequence
<220> FEATURE:
<223> OTHER INFORMATION: Synthetic construct

<400> SEQUENCE: 1
gatttctaga gtagtctgcg gagctttc                28

```
<210> SEQ ID NO 2
<211> LENGTH: 28
<212> TYPE: DNA
<213> ORGANISM: Artificial Sequence
<220> FEATURE:
<223> OTHER INFORMATION: Synthetic construct

<400> SEQUENCE: 2
gattctcgag ggtgttgaac tcctcgcg                                    28

<210> SEQ ID NO 3
<211> LENGTH: 29
<212> TYPE: DNA
<213> ORGANISM: Artificial Sequence
<220> FEATURE:
<223> OTHER INFORMATION: Synthetic construct

<400> SEQUENCE: 3
gattctcgag tttagcctga cgcaacaag                                   29

<210> SEQ ID NO 4
<211> LENGTH: 27
<212> TYPE: DNA
<213> ORGANISM: Artificial Sequence
<220> FEATURE:
<223> OTHER INFORMATION: Synthetic construct

<400> SEQUENCE: 4
gattgcatgc tccttcaccc aggcgag                                     27
```